United States Patent
Hamilton et al.

(10) Patent No.: US 6,667,424 B1
(45) Date of Patent: Dec. 23, 2003

(54) ABSORBENT ARTICLES WITH NITS AND FREE-FLOWING PARTICLES

(75) Inventors: Wendy L. Hamilton, Neenah, WI (US); Heather A. Sorebo, Appleton, WI (US); William G. Reeves, Appleton, WI (US); Patsy A. Hansen, Omro, WI (US); Emmanuelle C. Damay, Neenah, WI (US); Robert J. Makolin, Neenah, WI (US); Joseph DiPalma, Neenah, WI (US); Fung-Jou Chen, Appleton, WI (US); Jeffrey D. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/547,203

(22) Filed: Apr. 12, 2000

Related U.S. Application Data

(63) Continuation-in-part of application No. 09/165,875, filed on Oct. 2, 1998.
(60) Provisional application No. 60/129,752, filed on Apr. 16, 1999, and provisional application No. 60/129,746, filed on Apr. 16, 1999.

(51) Int. Cl.[7] ............................................... A61F 13/15
(52) U.S. Cl. ........................ 604/375; 604/360; 604/378
(58) Field of Search ................................. 604/365–375, 604/385.01, 378, 359–360

(56) References Cited

U.S. PATENT DOCUMENTS

| 1,843,037 A | 1/1932 | Mathey |
|---|---|---|
| 2,064,431 A | 12/1936 | Jurgensen |
| 2,331,355 A | 10/1943 | Strongson |
| 2,747,575 A | 5/1956 | Mercer |
| 2,787,271 A | 4/1957 | Clark |
| 2,952,260 A | 9/1960 | Burgeni |
| 3,029,817 A | 4/1962 | Harwood et al. |
| 3,036,573 A | 5/1962 | Voigtman et al. |

(List continued on next page.)

FOREIGN PATENT DOCUMENTS

| AU | 650912 | 4/1992 |
|---|---|---|
| CA | 803531 | 1/1969 |

(List continued on next page.)

OTHER PUBLICATIONS

US 5,674,210, 10/1997, Coles et al. (withdrawn)
American Society for Testing Materials (ASTM) Designation: D 1921–89, "Standard Test Methods for Particle Size (Sieve Analysis) of Plastic Materials[1]," published Aug. 1989.

(List continued on next page.)

*Primary Examiner*—Weilun Lo
*Assistant Examiner*—C. Lynne Anderson
(74) *Attorney, Agent, or Firm*—Pauley Petersen Kinne & Ericson

(57) ABSTRACT

Absorbent articles comprising fibrous nits and other free-flowing particles are provided. In one embodiment, an absorbent article includes free-flowing particles in a central portion which, in conjunction with other absorbent members, provides excellent body fit and good fluid handling performance. In another embodiment, good leakage control is provided by the combined effect of good intake and fluid handling performance of fibrous nits coupled with a wicking barrier between the nits and the longitudinal sides of the articles. An optional central rising member can further enhance the topography of the article when compressed by urging the portion comprising nits to deflect vertically upward. Also provided are methods of preparing cellulosic nits and incorporating them into absorbent articles.

56 Claims, 15 Drawing Sheets

U.S. PATENT DOCUMENTS

| | | |
|---|---|---|
| 3,143,113 A | 8/1964 | Mills |
| 3,211,147 A | 10/1965 | Pherson et al. |
| 3,230,955 A | 1/1966 | Joa et al. |
| 3,343,543 A | 9/1967 | Glassman |
| 3,395,201 A | 7/1968 | Kalwaites |
| 3,395,708 A | 8/1968 | Hervey et al. |
| 3,411,504 A | 11/1968 | Glassman |
| 3,430,630 A | 3/1969 | Megison et al. |
| 3,468,311 A | 9/1969 | Gallagher |
| 3,554,862 A | 1/1971 | Hervey et al. |
| 3,556,932 A | 1/1971 | Coscia et al. |
| 3,556,933 A | 1/1971 | Williams et al. |
| 3,559,650 A | 2/1971 | Larson |
| 3,575,174 A | 4/1971 | Mogor |
| 3,585,104 A | 6/1971 | Kleinert |
| 3,592,194 A | 7/1971 | Duncan |
| 3,595,235 A | 7/1971 | Jespersen |
| 3,599,388 A | 8/1971 | Feingold |
| 3,612,054 A | 10/1971 | Matsuda |
| 3,677,886 A | 7/1972 | Forsshlad et al. |
| 3,700,623 A | 10/1972 | Keim |
| 3,736,931 A | 6/1973 | Glassman |
| 3,772,076 A | 11/1973 | Keim |
| 3,836,336 A | 9/1974 | Yasui et al. |
| 3,885,158 A | 5/1975 | Flutie et al. |
| 3,886,941 A | 6/1975 | Duane et al. |
| 3,889,679 A | 6/1975 | Taylor |
| 3,899,388 A | 8/1975 | Petrovich et al. |
| 3,901,236 A | 8/1975 | Assarsson et al. |
| 3,903,890 A | 9/1975 | Mesek et al. |
| 3,954,107 A | 5/1976 | Chesky et al. |
| 3,972,855 A | 8/1976 | Martinsson et al. |
| 4,015,604 A | 4/1977 | Csillag |
| 4,029,101 A | 6/1977 | Chesky et al. |
| 4,059,114 A | 11/1977 | Richards |
| 4,062,362 A | 12/1977 | Schaar |
| 4,069,822 A | 1/1978 | Buell |
| 4,100,324 A | 7/1978 | Anderson et al. |
| 4,129,528 A | 12/1978 | Petrovich et al. |
| 4,144,122 A | 3/1979 | Emanuelsson et al. |
| 4,147,586 A | 4/1979 | Petrovich et al. |
| 4,190,563 A * | 2/1980 | Bosley et al. ............... 260/17.4 |
| 4,200,103 A | 4/1980 | Black et al. |
| 4,222,921 A | 9/1980 | Van Eenam |
| 4,247,362 A | 1/1981 | Williams |
| 4,282,874 A | 8/1981 | Mesek |
| 4,303,471 A | 12/1981 | Laursen |
| 4,324,246 A | 4/1982 | Mullane et al. |
| 4,327,728 A | 5/1982 | Elias |
| 4,340,058 A | 7/1982 | Pierce et al. |
| 4,342,314 A | 8/1982 | Radel et al. |
| 4,351,699 A | 9/1982 | Osborn, III |
| 4,397,644 A | 8/1983 | Matthews et al. |
| 4,405,326 A | 9/1983 | Lenaghan |
| 4,410,324 A | 10/1983 | Sabee |
| 4,432,833 A | 2/1984 | Breese |
| 4,460,642 A | 7/1984 | Errede et al. |
| 4,463,045 A | 7/1984 | Ahr et al. |
| 4,476,180 A | 10/1984 | Wnuk |
| 4,476,323 A | 10/1984 | Hellsten et al. |
| 4,482,429 A | 11/1984 | Klowak |
| 4,482,833 A | 11/1984 | Weinert et al. |
| 4,490,147 A | 12/1984 | Pierce et al. |
| 4,522,967 A | 6/1985 | Sheldon et al. |
| 4,524,474 A | 6/1985 | Svensson |
| 4,556,146 A | 12/1985 | Swanson et al. |
| 4,568,341 A | 2/1986 | Mitchell et al. |
| 4,573,986 A | 3/1986 | Minetola et al. |
| 4,578,070 A | 3/1986 | Holtman |
| 4,578,071 A | 3/1986 | Buell |
| 4,589,876 A | 5/1986 | Van Tilburg |
| 4,594,130 A | 6/1986 | Chang et al. |
| 4,627,848 A | 12/1986 | Lassen et al. |
| 4,636,209 A | 1/1987 | Lassen |
| 4,643,726 A | 2/1987 | Gegelys |
| 4,650,481 A | 3/1987 | O'Connor et al. |
| 4,654,161 A | 3/1987 | Kollmeier et al. |
| 4,655,759 A | 4/1987 | Romans-Hess et al. |
| 4,657,538 A | 4/1987 | Becker et al. |
| 4,675,394 A | 6/1987 | Solarek et al. |
| 4,676,784 A | 6/1987 | Erdman et al. |
| 4,676,786 A | 6/1987 | Nishino |
| 4,678,464 A | 7/1987 | Holtman |
| 4,681,793 A | 7/1987 | Linman et al. |
| 4,687,478 A | 8/1987 | Van Tilburg |
| 4,717,498 A | 1/1988 | Maxon |
| 4,723,953 A | 2/1988 | Rosenbaum et al. |
| 4,753,644 A | 6/1988 | Cottenden et al. |
| 4,758,240 A | 7/1988 | Glassman |
| 4,773,905 A | 9/1988 | Molee et al. |
| 4,781,711 A | 11/1988 | Houghton et al. |
| 4,787,896 A | 11/1988 | Houghton et al. |
| 4,793,898 A | 12/1988 | Laamanen et al. |
| 4,795,452 A | 1/1989 | Blaney et al. |
| 4,804,380 A | 2/1989 | Lassen et al. |
| 4,865,597 A | 9/1989 | Mason, Jr. et al. |
| 4,879,170 A | 11/1989 | Radwanski et al. |
| 4,886,513 A | 12/1989 | Mason, Jr. et al. |
| 4,900,318 A | 2/1990 | Toth |
| 4,936,839 A | 6/1990 | Molee et al. |
| 4,950,264 A | 8/1990 | Osborn, III |
| 4,960,845 A | 10/1990 | O'Lenick, Jr. |
| 4,963,139 A | 10/1990 | Dabroski |
| 4,973,325 A | 11/1990 | Sherrod et al. |
| 4,981,557 A | 1/1991 | Bjorkquist |
| 4,988,344 A | 1/1991 | Reising et al. |
| 5,007,906 A | 4/1991 | Osborn, III et al. |
| 5,008,344 A | 4/1991 | Bjorkquist |
| 5,009,650 A * | 4/1991 | Bernardin ................... 604/368 |
| 5,009,653 A | 4/1991 | Osborn, III |
| 5,030,229 A | 7/1991 | Yang |
| 5,030,314 A | 7/1991 | Lang |
| 5,048,589 A | 9/1991 | Cook et al. |
| 5,070,168 A | 12/1991 | O'Lenick, Jr. |
| 5,070,171 A | 12/1991 | O'Lenick, Jr. |
| 5,073,619 A | 12/1991 | O'Lenick, Jr. |
| 5,085,736 A | 2/1992 | Bjorkquist |
| 5,098,979 A | 3/1992 | O'Lenick, Jr. |
| 5,104,396 A | 4/1992 | Oatley et al. |
| 5,120,812 A | 6/1992 | O'Lenick, Jr. et al. |
| 5,135,294 A | 8/1992 | Ohshima et al. |
| 5,147,343 A | 9/1992 | Kellenberger |
| 5,149,765 A | 9/1992 | O'Lenick, Jr. |
| 5,151,091 A | 9/1992 | Glaug et al. |
| 5,167,654 A | 12/1992 | Yang |
| 5,171,302 A | 12/1992 | Buell |
| 5,188,625 A | 2/1993 | Van Iten et al. |
| 5,190,563 A | 3/1993 | Herron et al. |
| 5,196,499 A | 3/1993 | O'Lenick, Jr. |
| 5,197,959 A | 3/1993 | Buell |
| 5,225,047 A | 7/1993 | Graef et al. |
| 5,237,035 A | 8/1993 | O'Lenick, Jr. et al. |
| 5,242,435 A | 9/1993 | Murji et al. |
| 5,267,992 A | 12/1993 | Van Tilburg |
| 5,275,591 A | 1/1994 | Mavinkurve |
| 5,280,099 A | 1/1994 | Imperante et al. |
| 5,281,208 A | 1/1994 | Thompson et al. |
| 5,296,434 A | 3/1994 | Karl et al. |
| 5,300,055 A | 4/1994 | Buell |
| 5,300,358 A | 4/1994 | Evers |
| 5,300,666 A | 4/1994 | Imperante et al. |

| | | | | | | |
|---|---|---|---|---|---|---|
| 5,324,278 A | | 6/1994 | Visscher et al. | 5,800,417 A | 9/1998 | Goerg-Wood et al. |
| 5,342,337 A | | 8/1994 | Runeman et al. | 5,807,365 A | 9/1998 | Luceri |
| 5,348,547 A | | 9/1994 | Payne et al. | 5,807,367 A | 9/1998 | Dilnik et al. |
| 5,348,620 A | | 9/1994 | Hermans et al. | 5,810,798 A | 9/1998 | Finch et al. |
| 5,350,624 A | | 9/1994 | Georger et al. | 5,817,079 A | 10/1998 | Bergquist et al. |
| 5,356,405 A | | 10/1994 | Thompson et al. | 5,824,004 A | 10/1998 | Osborn, III et al. |
| 5,360,422 A | | 11/1994 | Brownlee et al. | 5,837,184 A | 11/1998 | Firgo et al. |
| 5,399,175 A | | 3/1995 | Glaug et al. | 5,843,852 A | 12/1998 | Dutkiewicz et al. |
| 5,399,412 A | | 3/1995 | Sudall et al. | 5,851,648 A | 12/1998 | Stone et al. |
| 5,401,267 A | | 3/1995 | Couture-Dorshner et al. | 5,855,572 A | 1/1999 | Schmidt |
| 5,405,342 A | | 4/1995 | Roessler et al. | 5,858,011 A | 1/1999 | Brown et al. |
| 5,423,786 A | | 6/1995 | Fung et al. | 5,858,021 A | 1/1999 | Sun et al. |
| 5,429,629 A | | 7/1995 | Latimer et al. | 5,865,824 A | 2/1999 | Chen et al. |
| 5,429,686 A | | 7/1995 | Chiu et al. | 5,866,242 A | 2/1999 | Tan et al. |
| 5,460,623 A | | 10/1995 | Emenaker et al. | 5,883,231 A | 3/1999 | Achter et al. |
| H1511 H | | 12/1995 | Chappell et al. | 5,885,263 A * | 3/1999 | Gancet et al. ............... 604/359 |
| 5,484,430 A | | 1/1996 | Osborn, III | 5,888,345 A | 3/1999 | Knapick et al. |
| 5,489,469 A | | 2/1996 | Kobayashi et al. | 5,914,125 A | 6/1999 | Andrews et al. |
| 5,490,846 A | | 2/1996 | Ellis et al. | 5,935,383 A | 8/1999 | Sun et al. |
| 5,509,913 A | | 4/1996 | Yeo | 5,990,377 A | 11/1999 | Chen et al. |
| 5,509,914 A | | 4/1996 | Osborn, III | 6,015,648 A | 1/2000 | Mitsumura et al. |
| 5,514,104 A | | 5/1996 | Cole et al. | 6,020,055 A | 2/2000 | Pearce |
| 5,522,809 A | | 6/1996 | Larsonneur | 6,020,536 A | 2/2000 | Österdahl et al. |
| 5,527,300 A | | 6/1996 | Sauer | 6,025,186 A * | 2/2000 | Kirk et al. ................. 424/94.4 |
| 5,533,991 A | | 7/1996 | Kirby et al. | 6,103,953 A | 8/2000 | Cree et al. |
| H1585 H | | 8/1996 | Ahr | 6,156,020 A * | 12/2000 | Roe et al. .................... 604/359 |
| 5,545,156 A | | 8/1996 | DiPalma et al. | 6,165,306 A | 12/2000 | Rajala |
| 5,558,656 A | | 9/1996 | Bergman | 6,172,276 B1 | 1/2001 | Hetzler et al. |
| 5,562,645 A | | 10/1996 | Tanzer et al. | 6,198,019 B1 | 3/2001 | Hansson et al. |
| 5,562,650 A | | 10/1996 | Everett et al. | | | |
| H1614 H | | 11/1996 | Mayer et al. | | FOREIGN PATENT DOCUMENTS | |
| 5,575,786 A | | 11/1996 | Osborn, III | CA | 884608 | 11/1971 |
| 5,578,025 A | | 11/1996 | May | DE | 32 05 931 A1 | 9/1983 |
| 5,591,148 A | | 1/1997 | McFall et al. | EP | 0 124 365 A1 | 11/1984 |
| 5,591,150 A | | 1/1997 | Olsen et al. | EP | 0 136 524 A1 | 4/1985 |
| 5,595,623 A | | 1/1997 | Gordon et al. | EP | 0 225 940 A1 | 6/1987 |
| 5,597,873 A * | | 1/1997 | Chambers et al. ........ 525/330.1 | EP | 0 360 285 A2 | 3/1990 |
| 5,599,334 A * | | 2/1997 | Johnston et al. ............ 604/359 | EP | 0 366 079 A2 | 5/1990 |
| 5,599,337 A | | 2/1997 | Mccoy | EP | 0 374 910 B1 | 6/1990 |
| 5,603,707 A | | 2/1997 | Trombetta et al. | EP | 0 391 727 A2 | 10/1990 |
| 5,607,551 A | | 3/1997 | Farrington, Jr. et al. | EP | 0 395 223 A2 | 10/1990 |
| 5,611,790 A | | 3/1997 | Osborn, III et al. | EP | 0 441 064 A1 | 8/1991 |
| 5,624,423 A | | 4/1997 | Anjur et al. | EP | 0 483 592 A1 | 5/1992 |
| 5,643,238 A | | 7/1997 | Baker | EP | 0 549 784 B1 | 7/1993 |
| 5,643,588 A * | | 7/1997 | Roe et al. .................... 424/402 | EP | 0 552 345 B1 | 9/1993 |
| 5,643,653 A | | 7/1997 | Griesbach, III et al. | EP | 0 597 273 A1 | 5/1994 |
| 5,647,863 A | | 7/1997 | Hammons et al. | EP | 0 682 927 A1 | 11/1995 |
| 5,649,915 A * | | 7/1997 | Chauvette et al. .......... 604/367 | EP | 0 687 453 A1 | 12/1995 |
| 5,649,916 A | | 7/1997 | DiPalma et al. | EP | 0 768 070 A1 | 4/1997 |
| 5,662,633 A | | 9/1997 | Doak et al. | EP | 0 768 072 A1 | 4/1997 |
| 5,672,248 A | | 9/1997 | Wendt et al. | EP | 0 781 537 A1 | 7/1997 |
| 5,681,303 A | | 10/1997 | Mills et al. | EP | 0 804 913 A1 | 11/1997 |
| 5,688,259 A | | 11/1997 | Osborn, III et al. | EP | 0 875 224 A1 | 11/1998 |
| 5,692,939 A | | 12/1997 | DesMarais | EP | 0 893 517 A2 | 1/1999 |
| 5,695,487 A | | 12/1997 | Cohen et al. | EP | 0 904 755 A2 | 3/1999 |
| 5,702,378 A | | 12/1997 | Widlund et al. | FR | 1358269 | 12/1964 |
| 5,711,970 A | | 1/1998 | Lau et al. | FR | 1554951 | 1/1969 |
| 5,725,821 A | | 3/1998 | Gannon et al. | GB | 2 233 235 A | 1/1991 |
| 5,741,241 A | | 4/1998 | Guidotti et al. | GB | 2 296 437 B | 7/1996 |
| 5,746,732 A | | 5/1998 | Olsson et al. | WO | WO 83/03051 A1 | 9/1983 |
| 5,752,947 A | | 5/1998 | Awolin | WO | WO 92/07535 A1 | 5/1992 |
| 5,755,710 A | | 5/1998 | Menard | WO | WO 96/17573 A3 | 6/1996 |
| 5,762,641 A * | | 6/1998 | Bewick-Sonntag et al. . 604/368 | WO | WO 96/38232 A1 | 12/1996 |
| 5,766,213 A | | 6/1998 | Hackman et al. | WO | WO 97/14389 A1 | 4/1997 |
| 5,769,835 A | | 6/1998 | Fell et al. | WO | WO 97/21453 A1 | 6/1997 |
| 5,772,845 A | | 6/1998 | Farrington, Jr. et al. | WO | WO 97/34558 A1 | 9/1997 |
| 5,779,860 A | | 7/1998 | Hollenberg et al. | WO | WO 97/34559 A1 | 9/1997 |
| 5,792,129 A | | 8/1998 | Johansson et al. | WO | WO 98/00081 A1 | 1/1998 |
| 5,792,130 A | | 8/1998 | Widlund et al. | WO | WO 98/00082 A1 | 1/1998 |
| 5,795,377 A | | 8/1998 | Tanner et al. | WO | WO 98/01684 A1 | 1/1998 |
| 5,795,921 A | | 8/1998 | Dyer et al. | WO | WO 98/24389 A1 | 6/1998 |

| | | |
|---|---|---|
| WO | WO 98/31318 A1 | 7/1998 |
| WO | WO 98/36720 A1 | 8/1998 |
| WO | WO 98/43684 A1 | 10/1998 |
| WO | WO 00/62730 A1 | 10/2000 |
| WO | WO 00/63487 A1 | 10/2000 |

OTHER PUBLICATIONS

American Society for Testing Materials (ASTM) Designation: D 3574–91, "Standard Test Methods for Flexible Cellular Materials—Slab, Bonded, and Molded Urethane Foams," Procedures C and H, published Mar. 1992.

American Society for Testing Materials (ASTM) Designation: D 4032–82, "Standard Test Method for Stiffness of Fabric by the Circular Bend Procedure," pp. 702–706, published Aug. 1982.

American Society for Testing Materials (ASTM) Designation: D6128–97, "Standard Shear Testing Method for Bulk Solids Using the Jenike Shear Cell[1]," published Oct. 1998.

Austin, L.G. et al., "Size Reduction of Solids: Crushing and Grinding Equipment," Chapter 12 in *Handbook of Powder Science and Technology*, 2nd edition, Chapman & Hall, New York, 1997, pp. 586–634.

Chatterjee, P.K., Editor, Absorbency, published by Elsevier, 1985, pp. 42–44.

Disapio, Alfred J. et al., "Microporous Macrobeads Provide New Opportunities in Skin Care," *Soap & Cosmetics*, vol. 75, No. 2, Feb. 1999, pp. 42–44,46–47.

Dullien, F.A.L., Porous Media: Fluid Transport and Pore Structure, Academic Press, New York, 1979, pp. 78–83.

Hostetter, David W., "Comparing Kneading and Disk Dispersion," *PaperAge*, Nov. 1995, p. 16.

Kallmes, O.J. et al., "The Gravimetric Absorbency Testing System (GATS)," Tappi Symposium—1985 Nonwovens Symposium, pp. 231–235.

Kaye, Brian H., "Mixing of Powders," Chapter 11 in *Handbook of Powder Science & Technology*, 2nd edition, Chapman & Hall, New York, 1997, pp. 568–585.

Main, Steve et al., "Retention Aids for High–Speed Paper Machines," *Tappi Journal*, vol. 82, No. 4, Apr. 1999, pp. 78–84.

O'Lenick Jr., Anthony J. et al., "Silicone Compounds: Not Just Oil Phases Anymore," *Soap/Cosmetics/Chemical Specialties*, Jun. 1998, pp. 55–57.

Rahn, K. et al., "New Cellulosic Polymers By Subsuquent Modification of 2,3–Dialdehyd Cellulose," *Cellulose Chemistry and Technology*, vol. 32, 1998, pp. 173–183.

Shinohara, Kunio, "Fundamental and Rheological Properties of Powders," Chapter 4 in *Handbook of Powder Science & Technology*, 2nd edition, Chapman & Hall, New York, 1997, pp. 96–145.

Federal Specification UU–T–595b, "Towel, Wiping, Paper: Industrial And Institutional," Apr. 4, 1967, 8 pages.

Federal Specification UU–T–595C, "Towel, Wiping, Paper: Industrial And Institutional," Jul. 27, 1976, 8 pages.

McCauley, N., "Vibrating and Gyratory Screeners: Proper Installation Yields Top Performance", *Powder and Bulk Engineering*, vol. 13, No. 12, Dec. 1999, pp. 35–39.

* cited by examiner

ABSORBENT ARTICLES WITH NITS AND FREE-FLOWING PARTICLES

This application is a continuation-in-part of application Ser. No. 09/165,875 entitle"Absorbent Article with Center Fill Performance" and filed in the U.S. Patent and Trademark Office on Oct. 2, 1998, application Ser. No. 09/165,871 entitled "Absorbent Article Having Good Body Fit Under Dynamic Conditions" and filed in the U.S. Patent and Trademark Office on Oct. 2, 1998, provisional application Ser. No. 60/129,752 entitled "Method of Making an Absorbent Article Containing Eucalyptus Nits" and filed in the U.S. Patent and Trademark Office on Apr. 16, 1999, and provisional application Ser. No. 60/129,746 entitled "Absorbent Article with Nits and Free-Flowing Particles" and filed in the U.S. Patent and Trademark Office on Apr. 16, 1999. The entirety of application Ser. Nos. 09/165,875, 09/165,871, 60/129,752, and 60/129,746 are hereby incorporated by reference.

BACKGROUND OF THE INVENTION

Absorbent articles for collecting body exudates typically comprise bulky fibrous absorbent webs as the main absorbent material for collecting body fluids. These webs often collapse when wetted, resulting in decreased void volume and degraded body-fit after the article is wetted. They also often lack the ability to conform well to the body of a wearer. What is needed are improved absorbent articles or absorbent materials capable of overcoming various limitations of past approaches. More specifically, improved materials and articles are needed that are capable of providing at least one of improved body fit, conformability, maintenance of void volume when wet or absorbency.

DEFINITIONS AND TEST METHODS

Figure 1:
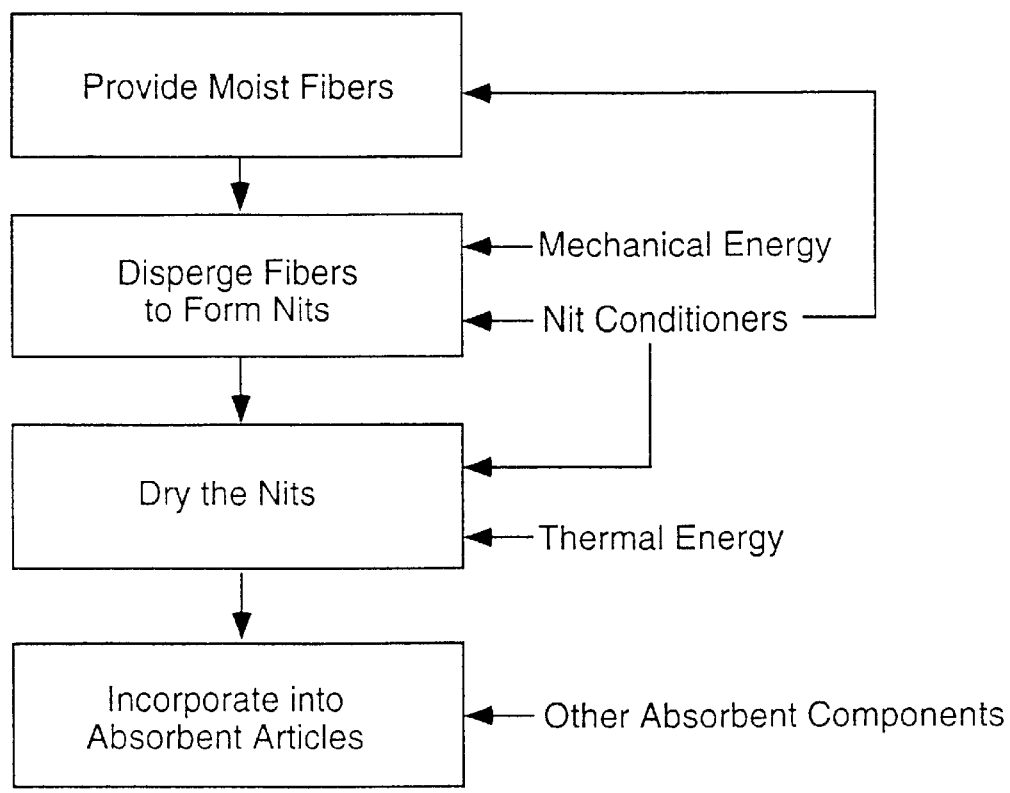
FIG. 1 is a flowchart depicting one choice of process steps for preparing free-flowing particles for use in absorbent articles.

As used herein, the term "absorbent article" refers to devices which absorb and contain liquids such as body exudates, and, more specifically, refers to devices which are placed against or in proximity to the body of the wearer to absorb and contain the various exudates discharged from the body.

As used herein, "biodegradable" refers to the ability of a compound to ultimately be degraded completely into carbon dioxide and water or biomass by microorganisms and/or natural environmental factors. In one embodiment, the free-flowing particles are substantially biodegradable. In another embodiment, the entire absorbent article is substantially biodegradable.

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, bacterial cellulose, and the like.

As used herein, "debonders" are chemicals which can be used to interfere with the normal hydrogen bonding that occurs between cellulosic fibers as they dry. Debonders generally comprise molecules with fatty portions or alkyl chains or other moieties that hinder hydrogen bonding. In many cases, debonders are cationic, often comprising a quaternary amine group. However, it is within the scope of the invention to use a debonding agent which may be either cationic, nonionic or anionic in nature. Without wishing to be limited by theory, it is believed that in addition to interfering with hydrogen bonding, debonders can also interfere with ionic and covalent bonding between fibers and other chemicals present in the web.

As used herein, the term "diaper" refers to an absorbent article generally worn by infants and incontinent persons that is worn about the lower torso of the wearer.

The term "disposable" is used herein to describe absorbent articles which are not intended to be laundered or otherwise restored or reused as an absorbent article (i.e., they are intended to be discarded after a single use and optionally to be recycled, composted or otherwise disposed of in an environmentally compatible manner).

As used herein, the term "dispersing" refers to mechanical processing of moist fibers at elevated consistency (e.g., greater than 8% and typically greater than 10% consistency, such as from about 12% to about 25% or from about 18% to about 42%) to cause the fibers to rub against each other without excessive damage to the fibers. Devices commonly known as kneaders or dispergers can be used, though both terms are encompassed by the term "disperger" as used herein. In this process, the fibers frequently become kinked or curled. Disperging is sometimes called "dispersion" in the papermaking arts, where it has been applied to modify fiber properties and enhance ink removal in recycling operations. Below, methods are presented for adapting disperging operations for the deliberate generation of fibrous nits—typically held to be undesirable prior to the present invention.

As used herein, a "dispersant" is a chemical compound that helps maintain fine solid particles in a state of suspension and inhibits their agglomeration or settling in a fluid medium. The term "dispersant" is not to be confused with the aforementioned terms "disperging" and "dispersion" which, as used herein, refer to mechanical processing of fibers. A variety of exemplary dispersants are disclosed in U.S. Pat. No. 5,795,377, issued Aug. 18, 1998 to Tanner et al., herein incorporated by reference. With the help of mechanical agitation, dispersants can also promote the breaking up of agglomerates of particles to form particle suspensions. Overall, dispersants known in the art are useful in preventing settling, deposition, precipitation, agglomeration, flocculation, coagulation, adherence or caking of solid particles in a fluid medium. Suitable dispersants include: organic polyelectrolytes including polycarboxylates, polysulfonates, polysulfates and polyphosphates; inorganic sulfonates, polyphosphates and silicates; and polymers containing polar groups such as polyacrylamides and polyols. Exemplary of synthetic polymer dispersants are the co-polymers of ethylenically unsaturated monomers with mono-ethylenically unsaturated carboxylic acids or their partially neutralized salts. Examples of useful monounsaturated carboxylic acids include acrylic acid, methacrylic acid, maleic acid, maleic anhydride, itaconic acid, itaconic anhydride, fumaric acid, half esters or half amides of maleic, fumaric and itaconic acid, crotonic acids, alkyl acrylates and methacrylates containing 1–18 carbon alkyl groups, vinyl esters, vinylaromatic compounds, dienes, etc. Homopolymers of mono-ethylenically unsaturated carboxylic acids or mixtures of these monomers may also be used. Examples include acrylic acid and methacrylic acid homopolymers and acrylic acid/methacrylic acid copolymers. Examples of polyacrylamides of use include polyacrylamides and polymethracrylamides and their N and N,N dialkyl derivatives containing 1–18 carbon alkyl groups.

Exemplary of the sulfonic acid containing polymer dispersants are the homopolymers of monoethylenically unsaturated sulfonic acids (or salts thereof) and copolymers thereof with the aforementioned ethylenically unsaturated monomers. Suitable sulfonated containing monomers include aromatic sulfonic acids (such as styrene sulfonic acids, 2-vinyl ethylbenzenesulfonic acid, 2-vinyl-3-bromobenzenesulfonic acid, 2-allylbenzene-sulfonic acid, vinylphenyl methanesulfonic acid), heterocyclic sulfonic acids (such as 2-sulfo-4-vinyl-furane and 2-sulfo-5-allylfurane), and aliphatic sulfonic acids (such as ethylenesulfonic acid and 1-phenylethylene sulfonic ac-id). Other sulfonated polymers of value in bringing about changes in the rheology of particulate mixtures or slurries include calcium lignosulfonates, formaldehyde modified napthalene sulfonates, sulfonated melamine-formaldehyde polymers and other sulfonated polymers.

As used herein, "equivalent nit particle size" is meant to be a measure of the equivalent diameter of a nit as if the nit were assumed to be spherically shaped. The equivalent nit particle size may be quantified, for example, by sieving a nit sample. Alternatively, the equivalent nit particle size for individual nits may be determined by an image analysis method wherein a nit sample is placed on a glass plate and a high-resolution picture is taken. From the measured area of a nit, the equivalent nit particle size can be calculated by assuming that the nit is circular across its cross-section. Nits useful in the present invention have an equivalent particle size that is greater than about 150 micrometers and less than about 10 millimeters (mm), more specifically greater than about 250 micrometers and less than about 5 mm, and suitably greater than about 300 micrometers and less than about 2 mm.

As used herein, the term "extensible" refers to articles that can increase in at least one of their dimensions in the x-y plane by at least 10% and specifically at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core can be extensible both in length and width. The absorbent article, however, may only be extensible in one of these directions such as the longitudinal direction. The absorbent article comprising an absorbent core can, in addition to being extensible, also be "stretchable". The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended (original) dimensions. It need not return all the way to its unextended dimensions, however. It may return to relaxed dimensions between its unextended dimensions and maximum extended dimensions.

As used herein, the term "fiber" or "fibrous" is meant to refer to a particulate material wherein the length to diameter ratio of such particulate material is greater than about 10 and specifically greater than about 20. Conversely, a "nonfiber" or "nonfibrous" material is meant to refer to a particulate material wherein the length to diameter ratio of such particulate material is about 10 or less.

As used herein, the term "free flowing" refers to the ability of particulates to readily flow in response to shear forces typically encountered in the use of a sanitary napkin worn against a human body—forces similar to those obtained by gently rubbing fingers together while the fingers are immersed in the particles of interest. Dry, loose, granular materials such as hardwood nits and polymethylurea (PMU) particles (hereafter described) are generally free-flowing under such conditions in contrast to materials such as clay which can deform but generally does not flow freely. Particularly, free-flowing particles will have an angle of repose (hereafter described) less than about 70° in the dry state and specifically less than about 60°. Similarly, free flowing particles will generally have high ratios of consolidation pressure ($\sigma_1$) to cohesive strength ($f_c$) measured according to the Jenike shear flow test for particles, as specified in ASTM Test Method D6128-97, "Standard Shear Testing Method for Bulk Solids Using the Jenike Shear Cell," herein incorporated by reference. This test examines interparticle shear forces under several loads and employs Mohr circle analysis to obtain consolidation pressure and cohesive strength of particles, as well as the effective angle of internal friction ($\delta$) and kinematic angle of internal friction ($\phi$). Of most interest is the ratio of consolidation pressure to cohesive strength, which herein is termed the "Flowability Coefficient." Flowability Coefficients of about 1 or less are indicative of a poorly flowing or nonflowing material. Free-flowing particles will generally have a Flowability Coefficient greater than about 2, specifically greater than about 2.5, more specifically greater than about 3, and most specifically from about 3.5 to about 10. Dry granular sand, a material with a very high flowability and low cohesive strength, can have a Flowability Coefficient of about 10. Jenike shear testing is performed commercially by Jenike & Johanson, Inc. (Westford, Mass.). In one embodiment, the particles of the present invention also have an effective angle of internal friction ($\delta$) of about 67° or less, specifically about 60° or less, and most specifically about 57° or less. Useful principles dealing with the Theological properties of granular particles are described by K. Shinohara in "Fundamental and Rheological Properties of Powders," Chapter 4 in Handbook of Powder Science and Technology, ed. by M. E. Fayed and L. Otten, $2^{nd}$ ed, Chapman & Hall, New York, 1987, pp. 96–145.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin. Characteristic high-yield fibers can have lignin content by mass of about 1% or greater, more specifically about 3% or greater, and still more specifically from about 2% to about 25%. Likewise, high yield fibers can have a kappa number greater than 20, for example. The high yield pulp fibers, after being prepared by pulping and optional bleaching steps and prior to being formed into dry bales or webs, in one embodiment can also be characterized by being comprised of comparatively whole, relatively undamaged fibers, high freeness (200 Canadian Standard Freeness (CSF) or greater, more specifically 250 CSF or greater, and still more specifically 400 CSF or greater), and low fines content (less than 25 percent, more specifically less than 20 percent, still more specifically less that 15 percent, and still more specifically less than 10 percent by the Britt jar test known to those skilled in the art of papermaking). In one embodiment, the high-yield fibers are predominately softwood and can be northern softwood BCTMP.

As used herein, the term "hydrophobic" refers to a material having a contact angle of water in air of at least 90 degrees. In contrast, as used herein, the term "hydrophilic" refers to a material having a contact angle of water in air of less than 90 degrees. A CAHN Surface Force Analyzer (SFA 222) can be used to measure hydrophilicity, as can a variety of other instruments known in the art.

As used herein, the term "nit" refers to a generally particulate material comprising entangled fibers. Nits are sometimes also referred to as "neps," "fiber bundles" or "fiber flakes." A nit will also generally comprise capillaries or voids within its structure between the entangled fibers forming the nit and may have an irregular shape, though more regular shapes such as ovoids or spheres can be obtained. Nits will generally exhibit a range of sizes resulting in a broad distribution of pore sizes within a mass of nits, with large pores between the nits and smaller pores within the nits. This pore size distribution can permit good intake of viscoelastic materials such as mucous and menses and can provide good intake of rapid gushes of fluid, while still providing the small pores needed for good absorbency and retention of fluid. Generally, nits and other free-flowing particles provide many pores with effective sizes on the order of the particle size, which generally is greater than the upper limits of pore size encountered in airlaids, fluff pulp, or tissue.

"Papermaking fibers," as used herein, include all known cellulosic fibers or fiber mixes comprising cellulosic fibers. Fibers suitable for making the webs of this invention comprise any natural or synthetic cellulosic fibers from biological sources including, but not limited to nonwoody fibers, such as cotton, abaca, kenaf, sabai grass, flax, esparto grass, straw, jute hemp, bagasse, milkweed floss fibers, and pineapple leaf fibers; bacteria capable of producing cellulose; lyocell, rayon, or other men-made cellulose fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods and other known pulping methods. In one embodiment, the nits comprise cellulosic fibers from two or more distinct biological sources, such as hardwood and softwood fibers, or wood-based fibers and cotton, or eucalyptus fibers and hemp fibers, and the like, wherein fibers from each source can be present at a level of 10% or greater based on mass of the fibers, or 20% or greater, or 30% or greater.

Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628, issued Jan. 21, 1997 to Gordon et al.

In embodiments with bleached papermaking fibers, any known bleaching method can be used. Synthetically prepared cellulose fiber can also be used, including rayon in all its varieties and other fibers derived from viscose or chemically modified cellulose. Chemically treated natural cellulosic fibers can be used such as mercerized pulps, chemically stiffened or crosslinked fibers, or sulfonated fibers. In one embodiment, the fibers are largely unrefined or only lightly refined (e.g., less than 3 hp-days/ton of fiber of applied refining energy). Either recycled fibers or virgin fibers or both can be used, but in one embodiment the fibers consist essentially of virgin fibers. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof.

As used herein, the term "polymeric web" refers to a porous or nonporous layer primarily composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides, and copolymers or mixtures thereof. Many additives and compounds can be added to the polymeric web or be part of the polymeric components, including antibacterial agents, odor-control additives, mineral filler particles, surfactants, pigments and dyes, emollients, and the like. The web may also be treated to have electrets for improved retention of certain particles or components of body fluids.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as pantiliners or tampons, or other absorbent articles such as diapers or incontinence pads. The term "feminine care pad" as used herein is synonymous with sanitary napkin.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant can be any surfactant known in the art, including anionic, cationic, nonionic and amphoteric surfactants. Examples of anionic surfactants include, among others, linear and branched-chain sodium alkylbenzenesulfonates; linear and branched-chain alkyl sulfates; linear and branched-chain alkyl ethoxy sulfates; and silicone phosphate esters, silicone sulfates, and silicone carboxylates such as those manufactured by Lambent Technologies, located in Norcross, Georgia. Cationic surfactants include, by way of illustration, tallow trimethylammonium chloride and, more generally, silicone amides, silicone amido quaternary amines, and silicone imidazoline quaternary amines. Examples of nonionic surfactants, include, again by way of illustration only, alkyl polyethoxylates; polyethoxylated alkylphenols; fatty acid ethanol amides; dimethicone copolyol esters, dimethiconol esters, and dimethicone copolyols such as those manufactured by Lambent Technologies; and complex polymers of ethylene oxide, propylene oxide, and alcohols. One exemplary class of amphoteric surfactants are the silicone amphoterics manufactured by Lambent Technologies (Norcross, Ga.).

As used herein, "water retention value" (WRV) is a measure that can be used to characterize some fibers useful for purposes of this invention. WRV is measured by dispersing 0.5 gram of fibers in deionized water, soaking overnight, then centrifuging the fibers in a 4.83 cm (1.9 inch) diameter tube with an 0.15 mm (100 mesh) screen at the bottom at 1000 gravities for 20 minutes. The samples are weighed, then dried at 105° C. for two hours and then weighed again. WRV is (wet weight-dry weight)/dry weight. Fibers useful for purposes of this invention can have a WRV of about 0.7 or greater, more specifically from about 1 to about 2. High yield pulp fibers typically have a WRV of about 1 or greater.

As used herein, a material will be considered to be "water soluble" when it substantially dissolves in excess water to form a solution, thereby losing its initial form and becoming essentially molecularly dispersed throughout the water solution. As a general rule, a water-soluble material will be free from a substantial degree of crosslinking, as crosslinking tends to render a material water insoluble. A material that is "water insoluble" is one that is not water soluble according to the above definition. Compressed materials in the present invention may be bonded with water soluble materials to permit expansion upon wetting. Water soluble adhesives may be used to join components in the present invention. Adhesives and absorbent components may also be water soluble in some embodiments.

As used herein, "wet strength agents" are materials used to protect, strengthen, or immobilize the bonds between fibers in the wet state. Typically, the means by which fibers are held together in paper and tissue products involve hydrogen bonds and sometimes combinations of hydrogen bonds and covalent and/or ionic bonds. In one embodiment of the present invention, wet strength additives are used to immobilize the fiber-to-fiber bond points and make them resistant to disruption in the wet state. In this instance, the term "wet state" as used herein refers to a condition when the product is largely saturated with water or other aqueous solutions, but could also mean significant saturation with water-containing body fluids such as urine, blood, mucus, menses, runny bowel movement, lymph and other body exudates.

There are a number of materials commonly used in the paper industry to impart wet strength to paper and board that are applicable to this invention. These materials are known in the art as "wet strength agents" and are commercially available from a wide variety of sources. Any material that when added to a paper web or sheet results in providing the sheet with a mean wet geometric tensile strength:dry geometric tensile strength ratio in excess of 0.1 will, for purposes of this invention, be termed a wet strength agent.

Suitable permanent wet strength agents are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin type resins. These materials have been described in patents issued to Keim (U.S. Pat. Nos. 3,700,623 and U.S. Pat. 3,772,076) and are sold by Hercules, Inc., located in Wilmington, Del. as KYMENE 557H polyamine-epichlorohydrin resins. Related materials are marketed by Henkel Chemical Co., located in Charlotte, N.C., and Georgia-Pacific Resins, Inc., located in Atlanta, Ga. Other useful wet strength agents include the polyamide-epichlorohydrin resins developed by Monsanto and marketed under the SANTO RES™ label, including those described in patents issued to Petrovich (U.S. Pat. No. 3,885,158; U.S. Pat. No. 3,899,388; U.S. Pat. No. 4,129,528 and U.S. Pat. No. 4,147,586) and van Eenam (U.S. Pat. No. 4,222,921). Although they are not as commonly used in consumer products, polyethylenimine resins are also suitable for immobilizing the bond points in the products of this invention. Another class of permanent-type wet strength agents are exemplified by the aminoplast resins obtained by reaction of formaldehyde with melamine or urea.

The efficacy of cationic wet strength agents can be enhanced by treatment of cellulosic fibers with reactive anionic compounds, according to U.S. Pat. No. 5,935,383, "Method for Improved Wet Strength Paper," issued Aug. 10, 1999 to Tong Sun and J. D.

Lindsay, herein incorporated by reference.

Intake and Rewet Test

The Intake and Rewet test indicates the absorption time to intake 2 ml of synthetic menses simulant. This test method is adapted for nits or other free-flowing particles in an elliptical-shaped nonwoven encasement having a major axis of 9.5 cm and a minor axis of 4 cm, comprising 3.0 grams of the dry granular material to be tested and a small quantity of superabsorbent particles underneath the granular absorbent material.

The elliptical pouch has a lower surface comprising a 20-gsm SMS (spunbond-meltblown-spunbond laminate) web produced by Corovin GMBH, Germany, treated with 15 gsm of Finley adhesive 2525A on the surface to be in contact with particles. This 20-gsm web is placed over a die element comprising a flat plate with an oval hole in it 9.5 cm long by 4 cm wide, with a depth of 9 mm. The 9-mm deep walls of the void in the die element are vertical. The web sags into the hole. Then 0.5 g of microcrystalline cellulose-coated superabsorbent particles are spread onto the adhesive of the web in the region over the oval hole of the underlying plate. The coated superabsorbent particles are prepared from Stockhausen 880 superabsorbent particles (Stockhausen Inc., Greenboro, S.C.) treated with cellulose powder type XL110 from Functional Foods, according to commonly owned copending application Ser. No. 60/129744, "Superabsorbent-containing Composites," filed Apr. 16, 1999, herein incorporated by reference. Afterwards, 3.0 grams of dry nits are spread over the superabsorbent particles such that the depth of the nits over the 20-gsm SMS layer is substantially uniform in the hole of the underlying plate. The beds of nits and the SMS layer are covered with a 40-gsm spunbond bicomponent (polyethylene/polypropylene) web available as Prism 12T from Kimberly-Clark Corp. (Neenah, Wis.). The lower SMS and upper bicomponent webs are then heat sealed by bringing a heated element into contact with the periphery of the SMS web around the oval hole in the underlying plate. The two webs are thus thermally joined together to define an oval-shaped pouch comprising nits and superabsorbent particles. The pouch is about 6 mm to about 9 mm thick. The pouch is placed on an hourglass-shaped coform layer 210 mm long and 65 mm wide, consisting essentially of 60 percent polypropylene and 40 percent bleached kraft softwood fibers. The coform is adhesively attached to a 20-micron thick polyethylene web serving as a backsheet. A 20-gsm spunbond cover was placed on top of the pouch and coform layer. The cover stock was attached to the coform and the backsheet with adhesive, and the article was die cut to the same width and length as the coform to form a sanitary napkin. A two millimeter edge seal was embossed within the coform and was two millimeters from the edge of the coform.

The pouch of absorbent particles is insulted with 2 ml of processed swine blood (obtained from Cocalico Inc., Reamstown, Pa.) delivered from a fluid reservoir having a 5.04 cm by 1.27 cm rectangular delivery slot cut into a clear acrylic block, such that the slot serves as a well to hold the fluid until it can be absorbed into the absorbent material. The block has a mass of 162 g and has a footprint (the contact area against the sample) of 7.3 cm by 7.5 cm, with the delivery slot being positioned centrally within the footprint. The slot is oriented with the longitudinal direction of the pouch and placed over the longitudinal centerline thereof. The surface of the block rests flat on the surface of the absorbent material, such that intake of fluid occurs substantially over the area of the slot adjacent the pouch of absorbent material. The time to absorb 2 ml of fluid is measured in seconds using a stopwatch, based on visual observation. Timing begins when the 2 ml of fluid enters the slot and contacts the absorbent material, and timing stops when the fluid has completely passed into the cover or upper surface of the absorbent material. A lower absorption time is an indication of faster intake rate for the particular material.

Once the material has been insulted, rewet can also be measured. The plastic block with the slot is left on the material for one minute after the fluid is absorbed. After one minute, the block is removed and the material is left undisturbed for 8 minutes. Next, preweighed pieces of Fort James (Richmond, Va.) Verigood® brand blotter material are placed on top of the specimen and subjected to a pressure of 3.45 kPa (0.5 psi) for three minutes. After the three minute interval, the blotter paper is removed and weighed, and the initial weight of the blotter is subtracted, yielding the amount of menstrual fluid absorbed by the blotter paper in grams. Higher values are an indication of a greater degree of rewet for the particular material tested.

A total of three rewet and intake measurements are done on each specimen.

Method for Determining Centrifuge Retention Capacity

As used herein, the Method for Determining Centrifuge Retention Capacity measures the amount of test fluid that a sample of absorbent material retains after a centrifugal force has been applied. The amount of fluid retained is calculated as a gram per gram retention. The test is typically conducted under TAPPI Standard Conditions.

In general, testing according to this method is performed by placing a 0.5 g sample of absorbent material into a modified cylinder, exposing the sample of absorbent material to a desired fluid for 60 minutes and then placing the cylinders into a centrifuge to remove excess fluid. The results are calculated to obtain the grams of fluid absorbed per gram of sample of absorbent material.

The following equipment and materials are used in the Method for Determining Centrifuge Retention Capacity:

Artificial Menses Fluid (simulant), disclosed in U.S. Pat. No. 5,883,231, issued Mar. 16,1999, to Achter et al. The simulant disclosed and claimed in U.S. Pat. No. 5,883,231 is commercially available from Cocalico Biologicals, Inc. 449 Stevens Rd., P.O. Box 265, Reamstown, Pa. 17567 USA.

Sorvall RT 6000D centrifuge, commercially available from Global Medical Instrumentation, Inc., 3874 Bridgewater Dr., St. Paul, Minn. 55123 USA.

Four 200 ml, screw top centrifuge bottles, commercially abailable from International Equipment Co., 300 Second Ave, Needham Heights, Mass. 02494 USA.

Balance, readable to 0.001 g (Note: standards should be NIST traceable and should be recertified at a frequency adequate to assure accuracy).

Four 50 ml Pyrex beakers.

Lab timer, 60 minute capacity, readable to one second, commercially available from from VWR Scientific Products, 1145 Conwell Ave., Willard, Ohio 44890 USA.

Four modified Lexan cylinders, 9 cm high, 3.1 cm ID, 4.8 cm OD, with a 300 holes/in$^2$ screen attached to the bottom.

U.S. standard 50 screen sieve, 8 inch diameter, 2 inch height, commercially available from VRW Scientific Products, 1145 Conwell Ave., Willard, Ohio 44890 USA, catalog number 57334-464.

Stainless steel screen, 4 holes per inch or enough open space to allow simulant to drain.

Specimen Preparation:

Prepare the absorbent material by using the U.S. standard 50 screen sieve to fractionate a sample to the 300 to 600 micron size. Store the fractionated sample in a sealed substantially airtight container for use when the sample or samples of absorbent material will be prepared. The modified cylinder is placed on the balance and the weight tared. Then 0.5 g of the −30/+50 particle size of the fractionated sample into one of the modified cylinders. Record this weight as Sample Weight. The modified cylinder containing the sample of absorbent material is weighed and this weight is recorded as Dry Cylinder Weight. Additional samples of absorbent material are placed in the three remaining modified cylinders according to the foregoing steps.

The simulant is removed from a refrigeration unit, placed on a rotator and then gently rotated for 30 minutes to thoroughly mix the contents and bring the simulant to room temperature.

The steps of the testing method are as follows:

1. 10 ml of simulant are placed into a 50 ml Pyrex beakers.
2. A modified cylinder containing the sample of absorbent material is placed into the 50 ml Pyrex beaker.
3. 15 ml of simulant are poured into the modified cylinder. This ensures that the sample of absorbent material has access to the simulant from both above and below.
4. Repeat steps 2 and 3 as necessary for any desired additional samples of absorbent material.
5. After step 4 has been completed, the timer is set for 60 minutes and started.
6. After 60 minutes have elapsed, the modified cylinders are removed from the Pyrex beakers and placed on the stainless steel screen for 60 seconds.
7. After 60 seconds, the modified cylinders are removed from the stainless steel screen and placed in the 200 ml centrifuge bottles.
8. The centrifuge bottles are placed in the centrifuge for 3 minutes at 1,200 rpm.
9. After 3 minutes, the modified cylinders are removed from the centrifuge bottles and the modified cylinders containing the sample of absorbent material is weighed. This weight is recorded as Wet Cylinder Weight.

The Centrifuge Retention Capacity of each sample of absorbent material is then alculated according to the following formula:

$$\frac{[(\text{Wet Cylinder Weight} - \text{Dry Cylinder Weight}) - \text{Product Weight}]}{(\text{Product Weight})}$$

Where reported in any of the following examples, the Centrifuge Retention Capacities are an average of two samples (i.e., n=2). The free-flowing particles of the present invention can have a Centrifuge Retention Capacity of at least 1.5 g/g, specifically at least 2 g/g, and most specifically about 2.2 g or greater.

Raw Material Absorbency Rate and Rewet Test Method

As used herein, the Raw Material Absorbency Rate and Rewet Test Method measures at least the following two characteristics of absorbent materials:

1. Absorbency rate—the amount of time, in seconds, it takes for a known amount of absorbent material to absorb multiple insults of known quantities of a fluid; and
2. Rewet—the amount of fluid, in grams, that is released from the absorbent material when blotter paper is placed on top of the absorbent material and a known pressure is applied for a predetermined period of time.

Testing according to this method consisted of using a stopwatch to determine the amount of time, in seconds, required for 10 ml of absorbent material to absorb multiple insults (1 or 2 ml) of fluid. A Harvard Syringe Pump (Harvard Apparatus, Inc., Holliston, Mass.) is programmed to dispense 2 ml of fluid onto 10 ml of absorbent material, at which time a tester simultaneously starts a stopwatch. The stopwatch is stopped when the 2 ml of fluid is absorbed into the absorbent material. A second insult of 2 ml is then dispensed and timed. The second insult is followed by a third insult, this time consisting of 1 ml, which is also timed. This results in a total of 5 ml and three timed insults. The tester then waits 60 seconds from absorption of the third insult before placing a pre-weighed blotter paper onto the 10 ml of absorbent material and applying a 0.5 psi pressure for 60 seconds. After 60 seconds, the blotter paper is reweighed and the fluid, in grams, that has been absorbed by the blotter paper is considered the amount of rewet. Testing is typically conducted under TAPPI Standard Conditions.

Equipment and Materials:

Harvard Apparatus Programmable Syringe Pump, Model No. 44, commercially available from Harvard Apparatus, South Natick, Mass. 01760 USA.

The fluid in this instance, by way of example only and not by way of limitation, is an artificial menses (simulant), disclosed in U.S. Pat. No. 5,883,231, issued Mar. 16, 1999, to Achter et al., the disclosure of which is hereby incorporated herein by reference to the extent that said disclosure is consistent (i.e., not contradictory) with the present specification. The simulant disclosed and claimed in U.S. Pat. No. 5,883,231 is commercially available from Cocalico Biologicals, Inc., 449 Stevens Rd., P.O. Box 265, Reamstown, Pa. 17567 USA.

Disposable plastic weighing boats commercially available from NCL of Wisconsin, Inc., Birnamwood, Wis. 54414 USA, part number W-D 80055.

60 cc disposable syringe, commercially available from Becton Dickenson, Rutherford, N.Y. USA; Tygon tubing, size 16 with 0.12" inner diameter, part number 6409-16, commercially available from Cole-Parmer Instrument Company, Chicago, Ill. 60648 USA; and ⅛" outer diameter hose, barb size, part number R-3603 and also commercially available from Cole-Parmer Instrument Company.

5.5 cm blotter paper, commercially available from from VWR Scientific Products, 1145 Conwell Ave., Willard, Ohio 44890 USA, catalog number 28310-015.

Weight, made by taking a 100 ml Pyrex beaker and filling it with any suitable substance to 717.5 grams to obtain a 0.5 psi loading.

Balance, readable to 0.001 g (Note: standards should be NIST traceable and should be recertified at a frequency adequate to assure accuracy).

Stopwatch, readable to 0.1 s (Note: stopwatch should be NIST traceable).

Graduated cylinder readable to 20 ml.

Clear acrylic plate (of a size sufficient to be supported on top of a disposable plastic weighing boat) with a hole drilled in the center thereof for insertion of the Tygon tubing.

Specimen Preparation:

The simulant is removed from a refrigeration unit, placed on a rotator and then gently rotated for 30 minutes to thoroughly mix the contents and bring the simulant to room temperature.

The graduated cylinder is placed onto the balance and the weight tared. 10 ml of absorbent material is introduced into the graduated cylinder. The graduated cylinder is removed from the balance. The bottom of the graduated cylinder is gently tapped on the top of the lab bench or similar hardened surface 10 times to induce settling. Visual inspection is made to ensure that there is 10 ml of absorbent material in the graduated cylinder. The 10 ml of absorbent material is poured into a weighing boat and the absorbent material is gently leveled.

The Harvard Syringe Pump is set to the Program Mode. The Infuse Rate is set to 250 ml/hr. with the Target Volume set to 2 ml. Diameter is set to the correct syringe size. The Harvard Syringe Pump is filled with 60 ml of simulant.

The steps of the testing method are as follows:

1. One end of the Tygon tubing is inserted through the hole in the acrylic plate.
2. The acrylic plate is placed over a weighing boat containing 10 ml of absorbent material. The Tygon tubing should be centered over the center of the absorbent material.
3. Simultaneously start the stopwatch and begin dispensing the first 2 ml insult of simulant.
4. Stop the stopwatch when the simulant is absorbed by the absorbent material. The reading on the stopwatch is recorded as "Insult 1" in seconds. In the event that the simulant is not absorbed by the absorbent material being tested (i.e., the simulant sits on the top of the absorbent material) within five minutes, stop the test and record 300+ seconds.
5. Simultaneously start the stopwatch and begin dispensing the second 2 ml insult of simulant.
6. Stop the stopwatch when the simulant is absorbed by the absorbent material. The reading on the stopwatch is recorded as "Insult 2" in seconds. In the event that the simulant is not absorbed by the absorbent material being tested (i.e., the simulant sits on the top of the absorbent material) within five minutes, stop the test and record 300+ seconds.
7. Simultaneously start the stopwatch and begin dispensing the simulant. In this instance, however, the Harvard Syringe Pump is halted after 1 ml of simulant has been dispensed.
8. Stop the stopwatch when the 1 ml of simulant is absorbed by the absorbent material. The reading on the stop watch is recorded as "Insult 3" in seconds. Once again, should the simulant not be absorbed by the absorbent material being tested (i.e., the simulant sits on the top of the absorbent material) within five minutes, stop the test and record 300+ seconds.
9. Wait 60 seconds after adsorption of the third insult.
10. Weigh two pieces of blotter paper and record this weight as "BP Dry."
11. At the end of the 60 seconds noted in step 9, gently place the 0.5 psi weight onto the blotter paper and start the stopwatch.
12. After 60 seconds, remove the weight and reweigh the blotter paper. This weight of the blotter paper is recorded as "BP Wet."

Steps 3 through 12 outlined above are repeated until the simulant is no longer absorbed by the absorbent material (i.e., the simulant sits on the top of the absorbent material and is not absorbed within five minutes).

The results of the rewet portion of the test method are recorded in grams and calculated as follows:

(BP Wet)−(BP Dry)=Rewet

Angle of Repose Test

Figure 9:
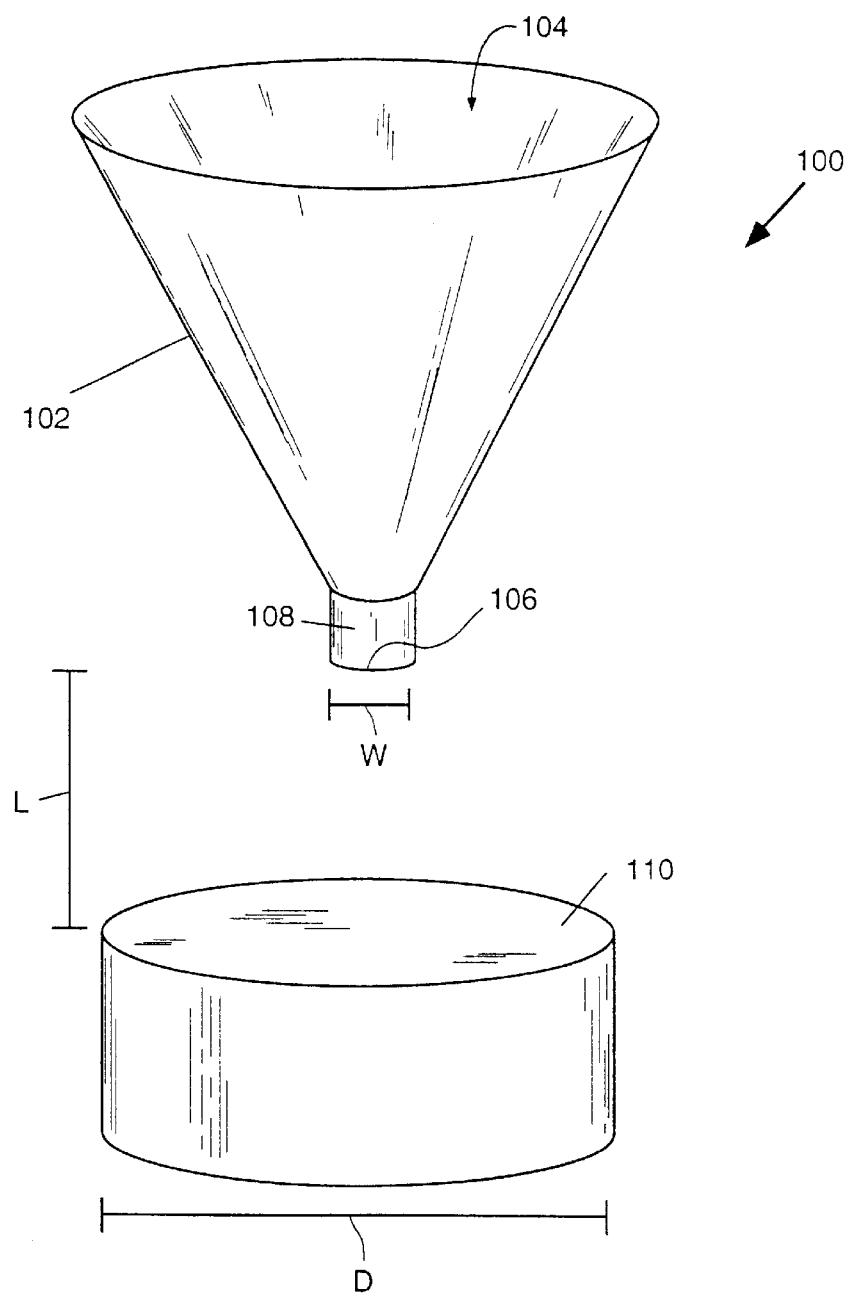
FIG. 9 shows a simple apparatus for measuring the angle of repose of free-flowing particles.

As used herein, "angle of repose" refers to the angle relative to the horizontal plane formed by the sides of a pile of free flowing particles prepared under controlled circumstances. Generally, a low angle of repose is indicative of the ability to flow readily, while a high angle of repose suggests that particulates do not flow well or tend to adhere. A measurement for angle of repose suited for the free-flowing particles of the present invention will be described using FIGS. 9 and 10. FIG. 9 depicts an apparatus 100 intended to permit measurement of the angle of repose of a pile of particles formed on a cylindrical platform 110. The apparatus comprises a powder funnel 102 (a Nalgene® 80 mm plastic funnel, Catalog No. 30252-955 in the VWR Scientific Products Catalog) having a height of 106 mm (the distance from the top of the funnel to the top of the stem 108). The powder funnel 102 has an upper opening 104 that is 104 mm wide. The lower stem 108 that has an outer diameter of 21 mm, a length of 33 mm, and is provided with a lower opening 106. Particles placed in the funnel fall to the brass cylinder 110 having a diameter D of 15.2 cm. The edges are free of burrs or other nonuniformities that would prevent particles from falling off the cylinder. The cylinder 110 is axially centered with the axis of the funnel 102. The upper surface of the cylinder 110 resides a distance L of 15 cm below the lower opening 106 of the funnel 102. The cylinder 110 has a height great enough to permit particles to spill to the side without rising from the underlying platform to reach the level of the upper surface of the cylinder 110. A height of at least 5 cm is recommended. The powder funnel 102 is held with a ringstand. Both the funnel 102 and the cylindrical platform 110 should be leveled.

Figure 10:
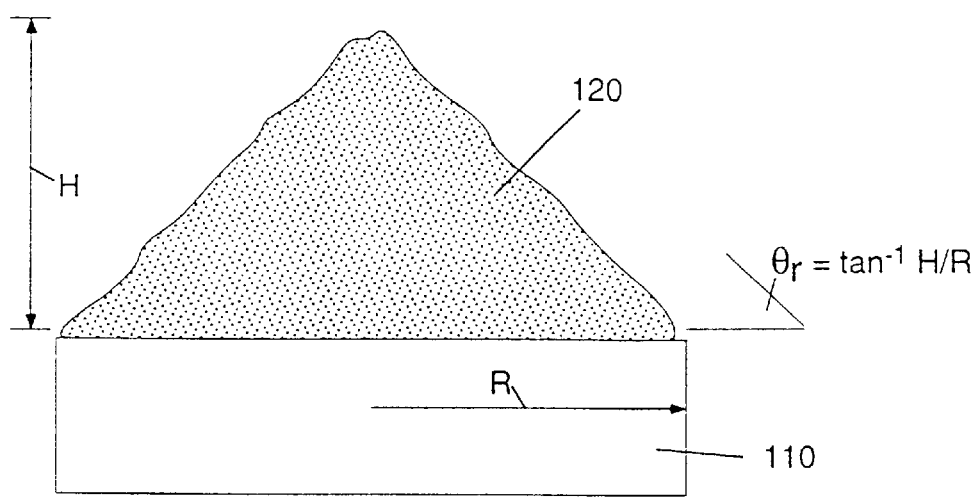
FIG. 10 shows how the angle of repose is determined in a pile of free-flowing particles.

To conduct the test, 100 cubic centimeters of particles are poured into the funnel 102. The particles are allowed to fall under the force of gravity to form a pile on the cylinder below, as shown in FIG. 10. The height H of the particle pile 120 on the cylinder 110 is measured, relative to the plane of the upper surface of the cylinder 110. The angle of repose, $\theta_r$, for the particles is then given by the arc tangent of H/R, where R is the radius of the cylinder 110 (D/2). This measurement is repeated 5 times to yield an average.

The effect of moisture should be considered in measuring angle of repose. Unless otherwise stated, it is assumed that the angle of repose is measured for substantially dry particles in equilibrium with air at 23° C. with a relative humidity of 30%, which typically will result in moisture content less than 5% for cellulosic nits. The effect of increasing moisture on the nits can be observed by measuring angle of repose as the nits are brought to increasing levels of moisture content. Conditioning the nits at a relative humidity of about 50%, for example, can bring the nits to a moisture content of about 5 to 7% in most cases, and higher relative humidities can be used to further elevate moisture content. For moisture contents above about 10%, it may be necessary to apply a fine mist of deionized water to the nits as they are stirred and to allow 15 minutes for a uniform redistribution of moisture within the nits. Once moistened, the nits are again measured for angle of repose.

If particles begin to bridge and cease flowing freely from the funnel, gentle tapping may be performed by gently striking the outer surface of the funnel three times at three uniformly spaced locations about the diameter of the funnel 102 at a height of 10 cm above the lower outlet 106, spaced apart by about 0.5 seconds. Striking is performed with only enough force to dislodge the particles. If bridging continues to be a problem, the particles can be slowly trickled into the funnel 102 to allow them to fall through the stem 108 and onto the cylindrical platform 110.

Nits without debonder and nits with a substantial amount of loose fibers projecting from the surface of the nits will often have an angle of repose as high as about 70 degrees when dry, but can still be useful in the present invention. When a greater degree of flowability is desired, free-flowing particles useful in the present invention can have an angle of repose while dry of about 60 degrees or less, more specifically about 55 degrees of less, and most specifically about 47 degrees or less, with exemplary ranges of from 10 to 45 degrees or from about 25 degrees to about 38 degrees. In some embodiments, at a moisture content of 50% (50 grams of water per 100 grams of dry fiber) and even 100%, the particles will still have an angle of repose less than about 75 degrees and can still be within the ranges specified above for dry particles. The angle of repose can increase by no more than 15 degrees, specifically no more than 10 degrees, and most specifically no more than 6 degrees, as moisture content is increased from 5% to 100%.

Gel Bed Permeability (GBP) Test

Figure 11:
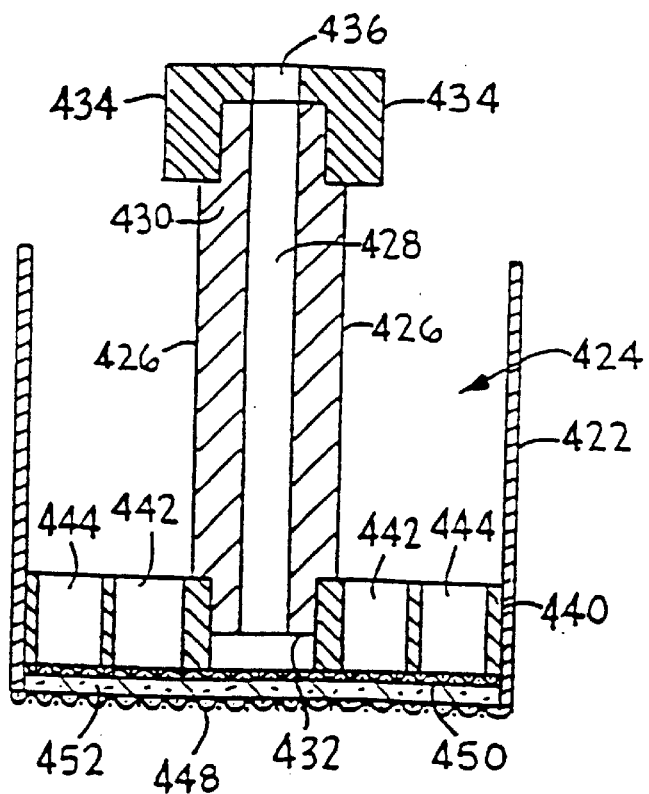
FIG. 11 depicts apparatus used to measure permeability of free-flowing particles.
Figure 12:
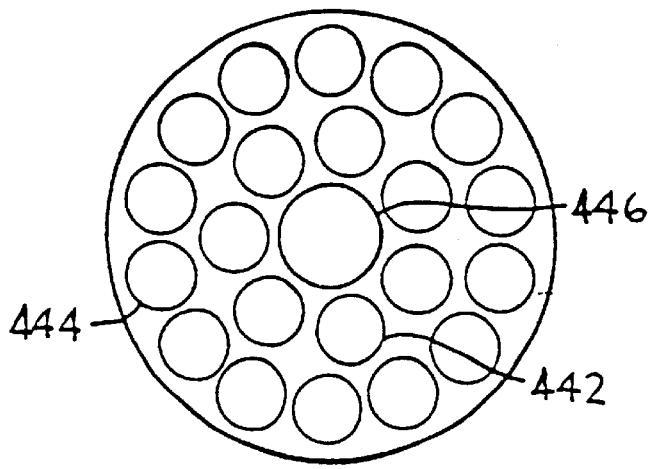
FIG. 12 depicts a bottom view of the apparatus of FIG. 11.

A suitable piston/cylinder apparatus for performing the Gel Bed Permeability (GBP) test is shown in FIGS. 11 and 12. Referring to FIG. 11, apparatus 420 consists of a cylinder 422 and a piston generally indicated as 424. As shown in FIG. 11, piston 424 consists of a cylindrical LEXAN® shaft 426 having a concentric cylindrical hole 428 bored down the longitudinal axis of the shaft. Both ends of shaft 426 are machined to provide ends 430 and 432. A weight, indicated as 434, rests on end 430 and has a cylindrical hole 436 bored through the center thereof. Inserted on the other end 432 is a circular piston head 440. Piston head 440 is sized so as to vertically move inside cylinder 422. As shown in FIG. 12, piston head 440 is provided with inner and outer concentric rings containing seven and fourteen 0.95 cm (0.375 inch) cylindrical holes, respectively, indicated generally by arrows 442 and 444. The holes in each of these concentric rings are bored from the top to bottom of piston head 440. Piston head 440 also has cylindrical hole 446 bored in the center thereof to receive end 432 of shaft 426.

Attached to the bottom end of cylinder 422 is a No. 400 mesh stainless steel cloth screen 448 that is biaxially stretched to tautness prior to attachment. Attached to the bottom end of piston head 440 is a No. 400 mesh stainless steel cloth screen 450 that is biaxially stretched to tautness prior to attachment. A sample of absorbent material indicated as 452 is supported on screen 448.

Cylinder 422 is bored from a transparent LEXAN® rod or equivalent and has an inner diameter of 6.00 cm (area=28.27 cm$^2$), a wall thickness of 0.5 cm, and a height of 5.0 cm. Piston head 440 is machined from a LEXAN® rod. It has a height of 0.625 inches (1.59 cm) and a diameter sized such that it fits within cylinder 422 with minimum wall clearances, but still slides freely. Hole 446 in the center of the piston head 440 has a threaded 0.625 inch (1.59 cm) opening (18 threads/inch) for end 432 of shaft 426. Shaft 426 is machined from a LEXAN® rod and has an outer diameter of 0.875 inches (2.22 cm) and an inner diameter of 0.250 inches (0.64 cm). End 432 is 0.5 inches (1.27 cm) long and is threaded to match hole 446 in piston head 440. End 430 is 2.54 cm (1 inch) long and 1.58 cm (0.623 inches) in diameter, forming an annular shoulder to support the stainless steel weight 434. The annular stainless steel weight 434 has an inner diameter of 1.59 cm (0.625 inches), so that it slips onto end 430 of shaft 426 and rests on the annular shoulder formed therein. The combined weight of piston 424 and weight 434 equals 596 g, which corresponds to a pressure of 20,685 dynes/cm$^2$ (0.30 psi), for an area of 28.27 cm$^2$.

When solutions flow through the piston/cylinder apparatus, the cylinder 422 generally rests on a 16-mesh, rigid stainless-steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the gel bed. It is important to measure each cylinder empty and keep track of which piston and weight were used. The same piston and weight should be used for measurement when gel is swollen.

The adsorbent layer used for GBP measurements is formed by swelling 3.0 g of a absorbent material in the GBP cylinder apparatus (dry polymer should be spread evenly over the screen of the cylinder prior to swelling) with 0.9% (w/v) aqueous NaCl for a time period of 15 minutes. The sample is taken from a population of absorbent material that is prescreened through U.S. standard #30 mesh and retained on U.S. standard #50 mesh. The absorbent material, therefore, has a particle size of between 300 and 600 microns. The particles may be prescreened by hand or automatically prescreened with, for example, a Ro-Tap Mechanical Sieve Shaker Model B, commercially available from W. S. Tyler, Inc., Mentor, Ohio USA.

At the end of the period, the cylinder is removed from the fluid and piston weight assembly is placed on the gel layer. The thickness of the swollen layer is determined by measuring from the bottom of the weight to top of the cylinder with a micrometer. The value obtained when taking this measurement with the empty cylinder is subtracted from the value obtained after swelling the gel. The resulting value is the height of the gel bed H.

The GBP measurement is initiated by adding the NaCl solution to cylinder 422 until the solution attains a height of 4.0 cm above the bottom of the gel layer 452. This solution height is maintained throughout the test. The quantity of fluid passing through the gel layer 452 versus time is measured gravimetrically. Data points are collected every second for the first two minutes of the test and every two seconds for the remainder. When the data are plotted as quantity of fluid passing through the bed versus time, it becomes clear to one skilled in the art when a steady flow rate has been attained. Only data collected once the flow rate has become steady is used in the flow rate calculation. The flow rate, Q, through the gel layer 452, is determined in units of g/sec by a linear least-square fit of fluid passing through the gel layer (measured in grams) versus time (in seconds).

Permeability in cm$^2$ is obtained by the following equation:

$$K=[Q*(H*Mu)]/[A*Rho*P]$$

where K=Gel Bed Permeability (cm$^2$); Q=flow rate (g/sec); H=height of gel bed (cm); Mu=liquid viscosity (poise); A=cross-sectional area for liquid flow (cm$^2$); Rho=liquid density (g/cm$^3$); and P=hydrostatic pressure (dynes/cm$^2$) (normally 3923 dynes/cm$^2$).

AUL and Free-swell Tests

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 2 kPa (0.3 pound per square inch).

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass. A level porous plate is used having ports confined within a 2.5 cm. diameter area to provide liquid saline solution, 0.9 (w/w) % sodium chloride, delivered from a reservoir to the porous plate such that there is no hydraulic head (neither positive pressure nor suction) at the top of the porous plate. Thus, fluid can be absorbed into the absorbent without overcoming a significant capillary pressure barrier to move liquid out of the porous plate. Fluid absorbed from the plate is replaced with liquid from the reservoir, which resides on an electronic balance that measures the amount of liquid removed from the reservoir and absorbed into the absorbent. The sample on the porous plate resides within a section of 2.54 cm (one-inch) inside diameter thermoplastic tubing machined-out slightly to be sure of concentricity. Stainless steel wire cloth with 0.15 mm openings (100 mesh) is fused on the bottom of the cylinder to restrain the sample and any particulates therein. Care must be taken to maintain a flat smooth bottom and not distort the inside of the cylinder. A 4.4 g piston ("spacer disk") is made from 2.54 cm (one inch) diameter solid material (e.g., a clear plastic) and is machined to closely fit without binding in the cylinder (i.e., the diameter is reduced to 2.527 cm). A standard 100 gm weight placed on the piston is used to provide a 21,000 dyne/sq.cm. (about 0.3 psi) restraining load which is commonly experienced in infant diapers. To carry out the test with a foam-like fibrous material or a foam, a material sample is cut into circular discs with a diameter slightly smaller than 2.54 cm (one inch) to freely fit within the sample tube. The sample mass should be from about 0.05 g to about 0.16 g.

This test is initiated by placing a 3 cm diameter GF/A glass filter paper onto the porous plate (the paper is sized to be larger than the inner diameter and smaller than the outer diameter of the cylinder), to insure good contact while eliminating evaporation over the ports of the DAT and then allowing saturation to occur. The material to be tested is placed on the wire cloth at the bottom of the AUL apparatus. The sample is then covered with the plastic spacer disc, which serves to protect the sample from being disturbed during the test and also to uniformly apply a load on the entire sample. After carefully placing the piston and weight on the sample in the cylinder, the AUL apparatus is placed on the glass filter paper. The amount of fluid pick-up is monitored as a function of time either directly by hand, with a strip chart recorder or directly into a data acquisition system.

The amount of fluid pickup measured after one hour is the AUL value, expressed as grams of liquid per dry gram of the tested material.

The AUL of the materials of the present invention can be above 6 grams/gram, more specifically about 10 grams/gram or greater, still more specifically about 15 grams/gram or greater, and most specifically about 25 grams/gram or greater, with an exemplary range of from about 9 to about 40 grams/gram. While high AUL values can be achieved without the addition of superabsorbent material or swellable binder material, especially high values of AUL are possible through incorporation of superabsorbent material into the absorbent structure.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. The materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

DETAILED DESCRIPTION OF THE DRAWINGS

It has been discovered that excellent fluid intake and control properties can be achieved in an absorbent article through the use of free-flowing absorbent particulates such as loose fibrous "nits" contained within an absorbent article. Synergistic benefits in fluid handling and body fit can be obtained when a pouch of free-flowing particles is coupled with other elements in an absorbent article. For example, good results have been obtained with cellulosic fibrous nits comprising papermaking fibers which have been mechanically formed by disperging to entangle fibers into small, discrete bundles.

Preparation of Nits

Some basic aspects of nit preparation are disclosed in U.S. Pat. No. 5,800,417, "Absorbent Composition Comprising Hydrogel-Forming Polymeric Material and Fiber Bundles," issued to K. Goerg-Wood et al., Sep. 18, 1998, herein incorporated by reference in its entirety.

One embodiment of a production process according to the present invention is illustrated in general in the flow chart of FIG. 1. Moist fibers are first provided, typically at an elevated consistency typically greater than 10% and more specifically at about 20% or higher and most specifically at about 30% or higher, with an exemplary range of 32% to about 55%. Any papermaking fibers can be used, as well as other cellulosic or absorbent polymer fibers capable of forming nits. In one embodiment, hardwood fibers are the primary fibrous component of the nits. In a related embodiment, short papermaking fibers are used for the production of nits, wherein the fibers have a weight-average length of less than 3.5 mm, specifically less than about 2 mm, and more specifically from about 0.2 mm to about 1.7 mm based on fiber length measurement with a Kajaani FS-200 instrument.

Providing the fibers at elevated consistency can require a dewatering step to make dilute fiber suspensions more concentrated. For example, a low-consistency slurry can be dewatered in a belt press. The belt press can be any suitable commercially-available unit, such as a Belt Filter Press from Komline Sanderson (Peapack, N.J.). Depending on the volume of material being processed, several belt presses may be arranged in parallel to provide the desired capacity. Process white water from the belt press can be conducted back to the pulping unit or other portions of the mill requiring water. At the outlet of the belt press, the filter cake typically can have from 25–45% solids, more specifically 30 to 45% solids and most specifically 35–40% solids. Other dewatering means for elevating the consistency of dilute fiber slurries include centrifugal filtration, screw presses, filtration and pressing on a papermaking machine, screen filters, flash drying, evaporative drying, and the like.

As shown in FIG. 1, mechanical energy is applied to the fibers during the disperging process of the present invention to cause fiber entanglement. A single- or twin-shaft disperger can be used capable of applying high-shear to pulp. High-shear treatment can last for about one minute or more (i.e., the average retention time of fibers passing through the device can be about one minute or greater). Examples of specific devices suitable for disperging include the BIVIS machine (commercially available from Clextral Company, Firminy Cedex, France) and the Maule shaft disperger such as Maule Type GR 11 manufactured by Ing. S. Maule & C. S.p.A., Torino, Italy, illustrated and described in detail in U.S. Pat. No. 5,772,845, "Soft Tissue," issued Jun. 30, 1998 to Farrington, Jr. et al., herein incorporated by reference.

Also of use in the present invention are other known dispergers for high-consistency treatment of papermaking pulp, such as those described by David W. Hostetter in "Comparing Kneading and Disk Dispersion," *PaperAge*, November 1995, p. 16. Hostetter explains that typical disk dispergers and kneaders for papermaking applications work by shearing action at around 30% consistency, with power requirements typically from 60 to 90 kWh/ton. Disk dispersion (or disperging) is generally most effective at 95° C. or higher, so disk dispergers are often preceded by a heating unit such as a heated screw conveyor. They operate typically at 1200 to 1800 rpm. One example is the Voith Sulzer "HTD" disperger (Appleton, Wis.), which has automatic power control and control over the gap where much of the shear on the fibers takes place. For best results, disk dispergers generally should be operated at low throughputs to increase the dwell time and energy applied to the fibers in order to promote nit formation. When exposure to high shear is for a short period of time, an additional dispersing step may be needed to create suitable nits.

Kneaders (regarded as a specific form of disperger as used herein) usually operate at lower temperatures, such as about 40° C. to 70° C., and are available in single and double shaft designs with rotational speeds of 200 to 1000 rpm. Retention time in the kneading zone is long compared to disk dispersion and can be effective in imparting curl or entanglement. One example of a kneader is the Voith Sulzer KD-500 kneading disperger (so termed in the above-referenced article of Hostetter—kneading can be considered as one form of disperging for the purposes of the present invention). The Ahlstrom MDR® Kneader can also be used. Another example of a kneader is provided in U.S. Pat. No. 3,836,336, issued Sep. 17, 1974 to Yasui et al., herein incorporated by reference. Kneaders are generally operated at power levels similar to those of disk dispergers or other dispergers, but can be operated at higher power levels for purposes of the present invention.

All forms of dispergers in prior commercial operation, including kneaders, disk dispergers, and shaft dispergers, are believed to have generally been run in a manner to avoid the formation of nits, which are not desired for commercial paper production. However, for the purposes of the present invention, nit formation is to be promoted by operation, for example, at one or more of elevated energy levels, elevated dwell times (tied to throughput), and elevated consistencies. For a given device, simple optimization of energy, throughput, and consistency can be applied to maximize nit production. Further, applied power, throughput rates, and temperature can be optimized for a given furnish to achieve the targeted particle density, absorbent capacity, and size distribution. Chemical additives (nit conditioners) can also play a useful but optional role, as described below. In one embodiment, energy levels above the typical levels of commercial disperger operation are applied. Specifically, energy levels above 90 kilowatt-hours/ton (kwh/t) can be applied. More specifically, energy levels for disperging of fibers can be any of the following ranges: about 95 kwh/t or greater, about 140 kwh/t or greater, about 200 kwh/t or greater, from about 95 kwh/ton to about 600 kwh/t, and from about 110 kwh/ton to about 300 kwh/ton.

In the BIVIS disperger, consistencies greater than 50% can be utilized without plugging. This device can be generally described as a pressurized twin screw shaft disperger, each shaft having several screw flights oriented in the direction of material flow followed by several flights oriented in the opposite direction to create back pressure. The screw flights are notched to permit the material to pass through the notches from one series of flights to another. One can utilize a consistency which is as high as possible for the particular machine used in order to maximize fiber-to-fiber contact, or can optimize the consistency for the particular product attributes being sought.

The temperature of the fibrous suspension entering the disperger can be about 20° C. or greater, specifically about 50° C. or greater, more specifically about 70° C. or greater, and most specifically about 90° C. or greater. Disperging (generally synonymous with "dispersing" or "dispersion" in the art of mechanical treatment of papermaking fibers) will elevate the temperature, depending on the energy input. The temperature of the pulp immediately after dispersion can be about 50° C. or higher, more specifically about 80° C. or higher, with an exemplary range of 90° C. to 130° C. and more specifically from about 100° C. to about 115° C. The upper limit on the temperature is dictated by whether or not the apparatus is pressurized, since the aqueous fibrous suspensions within an apparatus operating at atmospheric pressure cannot be heated beyond the boiling point of water. Other principles for operation of dispergers are disclosed in U.S. Pat. No. 5,348,620, "Method of Treating Papermaking Fibers for Making Tissue," issued to Hermans et al., Sep. 20, 1994, and those parts of which that are not contradictory to the present invention are herein incorporated by reference.

The outlet consistency from the disperger (e.g., a BIVIS or Maule device) can be from about 20% to about 75%, specifically from about 40% to about 60% and more specifically from about 45% to about 55%. Good results can be obtained with specific energy values above about 90 kilowatt hours per metric ton, though it is expected that some nits can be produced at energy input levels as low as 25 to 90 kilowatt-hours per metric ton and also at much higher specific energy levels, such as about 300 or 600 kilowatt-hours per metric ton. Outlet consistency in practice has ranged from 47% to 55%, though lower and higher values are within the scope of the present invention, as previously defined.

Nit Conditioners and Particle Conditioners

As shown in the embodiment of FIG. 1, the nits (as well as other free-flowing particles) can be treated at least in part with nit conditioners (or, more generally, "particle conditioners") such as a debonder, a lubricant, a wax, a silicone compound, or other hydrophobic material to modify fiber-fiber interactions during disperging and/or to modify particle-particle interactions once incorporated into an absorbent article. For example, nit conditioners or particle conditioners can improve the free flowing properties of the particles. Such conditioners and other chemicals can be added at any suitable time during preparation and treatment of the particles. In the case of nits, nit conditioners can be added in a pulper as pulp is initially being disintegrated and prepared, during or after a dewatering process wherein pulp consistency is being elevated, at the inlet of the disperger (e.g., at a feed screw), or nit conditioners and other chemicals can be injected into any one of several zones in the disperger itself or added to the nits after formation, such as before, during, or after drying. Also, chemical addition during or after nit drying can be selectively onto the surface of the surface and can efficiently modify particle-particle interactions.

Surprisingly, addition of debonder or lubricants prior to or during preparation of fibrous nits from moist fibers has been discovered to reduce the particle size distribution of the nits and can increase the yield of nits in a desired particle size range. In addition to the benefits obtained by adding debonders known from the art of papermaking, benefits in nit properties can also be achieved by adding known surfactants or dispersants during the processing of the nits. Without wishing to be bound by theory, it is believed that lubricants such as waxes, oils, and silicone compounds, or surfactants or dispersants, such as Triton X-100, when present during a disperging operation, can modify the surface interactions between fibers to reduce the size of nits formed from entangled fibers. It is also believed, again without wishing to be bound by theory, that the presence of an effective amount of at least one of lubricants, debonders, dispersants and surfactants during high-consistency disperging of papermaking fibers can reduce the friction between nits and allow nits to flow past one another more readily, permitting local velocity fields or shear fields to be established that better promote separation of nits and creation of nits with reduced quantities of fibers projecting from the surface of the nits.

Without wishing to be bound by theory, it is believed that debonders on the surface of a fibrous nit can prevent bonding or clumping between nits and can enhance the lubricity of the nits relative to one another. Thus, it is believed that debonder selectively located on the outer surface of a nit will be more effective in terms of the performance of an absorbent article than debonder applied uniformly throughout the fibrous material of a nit. However, in the manufacturing of nits, it has been found that debonder present throughout the pulp often improves the size distribution of the nits by reducing the size of the nits into a desired range. Again, without wishing to be bound by theory, it is believed that the presence of debonder increases the lubricity of fibers during a disperging process and allows flocs to be broken up into smaller sized bundles. Thus, for example, a process that might result in a mean particle size of about 1 mm without debonder might yield a mean particle size of about 0.6 mm with 0.5% to 2% debonder present (weight percentage based on dry fiber mass).

Application of the debonding agent can therefore be done in either or both of two ways: (1) applying a debonder to the fibers or fiber slurry prior to or during disperging to control formation of nits and nit size, and (2) applying a debonder (or other hydrophobic material or compound comprising fatty moieties) to the surface of at least a portion of the nits after the nits have been formed by mechanical processes and before, after, or during drying of the nits.

Many debonders tend to reduce water absorbency as a result of hydrophobicity caused by the same fatty long chain portion which gives the product its effectiveness. In order to overcome this problem, some manufacturers have formed adducts of ethylene or propylene oxide in order to make the products somewhat more hydrophilic. Those interested in the chemistry of debonders will find them widely described in the patent literature. The following list of U.S. patents provides a sampling, although it is not intended to be exhaustive: Hervey et al., U.S. Pat. Nos. 3,395,708 and 3,554,862; Forssblad et al, U.S. Pat. No. 3,677,886; Emanuelsson et al., U.S. Pat. No. 4,144,122; Osborne, III., U.S. Pat. No. 4,351,699; and Hellsten et al., U.S. Pat. No. 4,476,323. All of the aforementioned patents describe cationic debonders. Laursen, in U.S. Pat. No. 4,303,471, herein incorporated by reference, describes what might be considered a representative nonanionic debonder.

Suitable debonders include any number of quaternary ammonium compounds and other softeners known in the art, including Berocell 596 and 584 (quaternary ammonium compounds) manufactured by Eka Nobel Inc., which are believed to be made in accordance with U.S. Pat. Nos. 3,972,855 and 4,144,122; Adogen 442 (dimethyl dihydrogenated tallow ammonium chloride) manufactured by Sherex Chemical Company; Quasoft 203 (quaternary ammonium salt) manufactured by Quaker Chemical Company; and Arquad 2HT75 (di(hydrogenated tallow) dimethyl ammonium chloride) manufactured by Akzo Chemical Company. Softening agents known in the art of tissue making can also serve as debonders or hydrophobic matter suitable for the present invention and can include, without limitation, fatty acids, waxes, quaternary ammonium salts, dimethyl dihydrogenated tallow ammonium chloride, quaternary ammonium methyl sulfate, carboxylated polyethylene, cocamide diethanol amine, coco betaine, sodium lauroyl sarcosinate, partly ethoxylated quaternary ammonium salt, distearyl dimethyl ammonium chloride, methyl-1-oleyl amidoethyl-2-oleyl imidazolinium methylsulfate (Varisoft 3690 from Witco Corporation), and the like.

Anti-static agents typically have side chains similar to those of useful debonders and can be present as well. In some cases, anti-static compounds are helpful in reducing static electricity-induced clumping of nits in their dry state, especially during manufacturing.

Silicone compounds can be useful in providing nits with desired properties, especially in terms of resisting clumping when wet and in providing useful tactile and free flowing properties when dry. Useful silicone compounds include silicone-based debonders, anti-static agents, softness agents, surface active agents, and the like, many of which can be obtained from Lambent Technologies, Inc., as described by A. J. O'Lenick, Jr., and J. K. Parkinson, in "Silicone Compounds: Not Just Oil Phases Anymore," *Soap/Cosmetics/Chemical Specialties*, Vol. 74, No. 6, June 1998, pp. 55–57. Exemplary silicone compounds include silicone quats such as silicone alkylamido quaternary compounds based on dimethicone copolyol chemistry, which can be useful as softeners, anti-static agents, and debonders; silicone esters, including phosphate esters which can provide lubricity; dimethiconol stearate and dimethicone copolyol isostearate, which is highly lubricious and can be applied as microemulsion in water; silicone copolymers with polyacrylate, polyacrylamide, or polysulfonic acid; silicone iethioniates; silicone carboxylates; silicone sulfates; silicone sulfosuccinates; silicone amphoterics; silicone betaines; and silicone imidazoline quats. Related patents describing such compounds including the following: U.S. Pat. Nos. 5,149,765; 4,960,845; 5,296,434; 4,717,498; 5,098,979; 5,135,294; 5,196,499; 5,073,619; 4,654,161; 5,237,035; 5,070,171; 5,070,168; 5,280,099; 5,300,666; 4,482,429; 4,432,833 (which discloses hydrophilic quaternary amine debonders) and U.S. Pat. No. 5,120,812, all of which are herein incorporated by reference. Hydrophilic debonders may be applied at the same doses and in a similar manner as hydrophobic debonders.

Though chemical additives that serve as debonders or lubricants can be useful in the production of nits for one or more of prevention of agglomeration, reduction of particle cohesiveness, prevention of static electricity (in the case of some cationic debonders in particular), and good control over nit size during disperging, nevertheless, other surface-active compounds can also play a role in controlling nit formation during disperging. Thus, a variety of surfactants and dispersants (previously defined) known in the art can also be applied during disperging to modify fiber-fiber interactions, modify nit-nit interactions, or control flocculation tendencies in the pulp suspension, all with potential benefits in controlling nit size or rheology of the dry particles.

Surfactants can be anionic, cationic, or nonionic, and can include any known in the art that are not incompatible with the health and property requirements of the present invention.

The nits can be combined with other agents in the pouch to further increase the absorbent capacity of the pouch or to control fluid the handling performance or macroscopic mechanical or rheological properties of the contents of the pouch. Materials capable of providing additional absorbent capacity include superabsorbent particles, particularly superabsorbents adapted for intake of menses, cellulose fibers, superabsorbent fibers and films, and one or more layers of a superabsorbent-treated tissue. The nits can also comprise a percentage of inorganic material or minerals such as clays (e.g., kaolin clay, bentonite, etc.), calcium carbonate, zeolites, vermiculite, titanium dioxide, mica, talc, alumina, silica, sodium bicarbonate, and the like. Other additives can be applied for specific purposes, such as odor control agents, ion exchange resins, anti-microbials, chitosan and chitin particles or additives, enzymes, surfactants, plasticizers such as polyols, and the like. Add-on levels can be varied to achieve the desired objectives, but by way of example can be selected from any of the following ranges for weight percents based on dry fibers: from 1% to 50%, from 2% to 10%, from 1%–5%, less than 10%, less than about 5%, less than 2%, from about 0.2% to about 3%, and substantially 0%.

For polymethyl urea spheres or for free-flowing particles in general, Vermiculite and clay particles can be present, particularly when other more regular shaped particles are present to enhance flowability. For example, if about 20% or more, specifically about 30% or more and more specifically about 40% or more of the volume of the particulate matter is occupied by substantially spherical or ovoid free-flowing particles, non-spherical particles such as vermiculite or clays can be present while still permitting good rheological properties to be maintained. Likewise, when over 40% and specifically over 50% of the mass of particulate matter is nits, then clays or vermiculite can be present without suffering from the rheological disadvantages presented by the pure minerals.

Drying of Nits

After disperging, the nits generally require input of further energy to dry them, as shown in FIG. 1. In some embodiments, the nits, once dried, are substantially free of clumps of multiple nits. Thus, some form of agitation during drying can be useful. Agitation after drying to break apart clumps can also be practiced. Once the nits are extruded or removed from the disperger in their moist state, they can be agitated and maintained in a loose state during drying or until they are sufficiently dry that hydrogen bonds between nits are unlikely to form. A high-shear air dryer or fluidized bed dryer can be used, wherein jets of heated air rising from beneath the nits in a tank, drum, rotary dryer, or bed stir and agitate the nits and help maintain them in a loosened state. In one embodiment, jets of air adjacent the exit port of the disperger immediately break up the nits and cause both agitation and drying to begin. Likewise, nits may be dumped, conveyed, or pneumatically blown into rotating drums or tumblers which permit passage of heated gases into the nits. Rotating dryer units, especially those with stirring means or spoiler bars are also useful, for the mechanical stirring or motion of the dryer helps prevent clumping of the nits as they dry and helps in drying the nits uniformly. Periodic bursts of high velocity air jets in the dryers to further agitate the particles can be helpful. Any number of commercial particle dryers, fluidized beds systems, and high shear dryers can be adapted to the purpose of drying nits, using principles well known to those skilled in the art. Examples include particle processing equipment of Carman Industries, Inc., including Carman® Fluid Bed Processors such as the Model FBP-1322, Adjust-A-Flow™ Vibrating Feeders, and Vibrating Bin Dischargers (see the Web pages for Carman Industries).

Useful examples of fluidized bed dryers are the fluid bed dryers of Swenson Process Equipment (15700 Lathrop Avenue Harvey, Ill. 60426), or the Swenson rotary dryers and flash dryers.

Other examples of useful dryer means include the "plow dryer" of Processall, Inc., (Cincinnati, Ohio), which uses primarily mechanical means to fluidize the particles without high shear or particle degradation. Fluidization is achieved by means of a shaft with attached mixing elements. This device comprises a vessel with a shaft having a series of rotating elements (plows), designed to lift and separate the product inside the vessel. The design of the blades, the number and spacing of the elements, and the speed all contribute to fluidization. The application of upward moving jets of air in the plow mixer is believed to offer advantages over mechanical action alone. Thus, the nits can be dried by a combination of low-shear gaseous fluidization and the action of rotating plow elements in a tank. In this manner, agglomerates can be broken up and rapid drying can be achieved. However, mechanical shear can replace much of the shear normally provided by gas streams, as exemplified by the Processall U-MAX Rotary Vacuum Dryers (Cincinnati, Ohio).

Following application of suitable mechanical energy into an elevated consistency slurry of fibers, the fibers will generally have become entangled into small, dense bundles (nits). The nits can have a mean particle size of about 50 micrometers to about 1000 micrometers, and more specifically within the range of from about 100 micrometers to about 850 micrometers, more specifically still from about 300 micrometers to about 850 micrometers, and most specifically from about 300 micrometers to about 600 micrometers, as determined by sieve analysis according to American Society for Testing and Materials (ASTM) test method D-1921. In one embodiment, less than 15% by weight and more specifically less than 5% by weight of the nits have a particle size greater than 2 mm or a size less than 50 micrometers. More specifically, less than 5% by weight of the nits have a particle size greater than 1 mm. Most specifically, less than 1% by weight of the nits have a particle size greater than 1 mm. Alternatively, at least 90% by weight and or, more specifically, at least 95% by weight of the dry nits or dry free-flowing particles have a particle size, as determined by sieve analysis (e.g., ASTM method D-1921), of any one of the following ranges: from 100 micrometers to 850 micrometers, from 100 micrometers to 800 micrometers, from 300 micrometers to 850 micrometers, from 300 micrometers to 600 micrometers. It is understood that the particles measured by sieve analysis may comprise cohesive agglomerates of smaller particles.

Methods of manufacturing the nits can further comprise subsequent treatments after drying such as sorting, sieving, screening, winnowing, and the like to remove the largest nits and/or to remove small fibers or other undesired particles. Sorting of the nits by particle size by screening, sieving, and the like can be done. Sorting or separating can also be performed by aerodynamic methods (e.g., entrainment in a fluidized bed) to remove particles with the largest effective surface area or aerodynamic drag, or to sort particles according to density. Cyclones can be effective in sorting particles entrained in air or other fluids according to the density of the particles. Several useful principles for classification and size reduction of particles are described in "Size Reduction of Solids: Crushing and Grinding Equipment," by L. G. Austin and O. Trass, Chapter 12 in *Handbook of Powder Science and Technology*, ed. by M. E. Fayed and L. Otten, $2^{nd}$ ed, Chapman & Hall, New York, 1887, pp. 586–634, with particular emphasis on pp. 610–611. Nits can be classified by other methods such as by screening, exemplified by vibrating or gyratory screeners, such as those described by N. McCauley in "Vibrating and Gyratory Screeners: Proper Installation Yields Top Performance," in *Powder and Bulk Engineering*, December 1999, pp. 35–39; sieving, including ultrasonic sieving, such as with a SonoScreen® device by Telsonic Ultrasonics (Bridgeport, N.J.), or gyratory sieves, such as the Vort-Siv® Model RBF-10 gyratory sieve (MM Industries, Salem, Ohio); air classification such as with the NSP Powderizer® by Sturtevant, Inc. (Hanover, Mass.) or Marsulex® Air Classifiers (Marsulex Environmental Technologies, Lebanon, Pa.), or centrifugal air classifiers by CCE Technologies (Eagan, Minn.) and the like. In one embodiment, classification into two or more particle sizes is performed with a Coanda-effect gas stream particle classifier as described in U.S. Pat. No. 6,015,648, "Gas Stream Classifier and Process for Producing Toner," issued to S. Mitsumura et al., Jan. 18, 2000, herein incorporated by reference.

The dry nits typically have a density above the critical density of the fibers, so that upon being wetted, the individual nits are unlikely to lose substantial volume but can even swell, resulting in increased void volume or improved body fit of a pouch of nits in an absorbent article. Nits combined with hydrogel forming materials (superabsorbent particles) are especially likely to swell substantially upon wetting and can improve body fit through that mechanism.

Other Free-flowing Particles

In addition to cellulosic nits, useful materials for forming free-flowing particles include polymethyl urea spheres, as disclosed in WO 98/43684, "Absorbent Item," M. Raidel, Oct. 8, 1998. Microporous macrobeads can also be used, such as those disclosed by A. J. Disapio et al. in "Microporous Macrobeads Provide New Opportunities in Skin Care," *Soap and Cosmetics*, Vol. 75, No. 2, February 1999, pp. 42–47, which are palpable polymeric beads that may be spherical or formed by attrition of spheres comprising pores within the bead for retention or release of chemical agents or liquids. Microporous macrobeads are commonly made from acrylate copolymers with added monomers to control surface properties, void volume, etc. For example, ester-rich monomers lead to highly lipophilic surfaces. Particle size for macrobeads useful in the present invention can be from about 100 to 500 microns, or from about 300 to 600 microns. Microporous macrobeads may be used alone or in combination with nits, microspheres, beads, or PMU particles. Porous, hollow, or solid spheres of silica and other minerals can also be used, as well as other particle shapes adapted for free flowing performance. Particles that have been coated with anti-stick agents such as silicones, talc, fluorinated polymers, and the like can also provide good flowability in the dry state.

The free-flowing particles can be absorbent but substantially non-swelling (i.e., when wetted with 50% moisture by weight, the bulk volume of the assembled particles increases by less than 20%, or at a 200% moisture uptake, the bulk volume of the particles increases by less than 25%). When an effective quantity of free-flowing particles are disposed within a porous pouch or restrained between two webs of material, with the web closest to the body side of the wearer of the absorbent article necessarily being porous, the free-flowing particles can serve both as an effective intake means for the absorption of menses and other body fluids, and as a body-conforming means for maintaining good fit against the body and comfort of the wearer. In one embodiment, the free-flowing particles can remain mobile even when wet, particularly when previously treated with at least one of lubricants, debonders, surfactants, dispersants, or hydrophobic material, and can flow in response to shear or compressive forces over a wide range of saturation values, permitting the nits to conform to the body and provide comfort.

Two or more kinds of free-flowing particles may be combined. The kinds of particles present in an absorbent article can differ in physical properties such as particle size, surface smoothness, wetting characteristics, presence of debonder or anti-static compounds or other anti-clumping agents; density, fiber type, fuzziness or degree of fibrillation, etc. Other particles or agents may be added for comfort, compressibility, and tactile properties, including small pieces of soft, deformable foam, such as regular or irregular shaped particles of foam rubber or polyurethane foam, having, by way of example only, a particle size from about 300 micrometers to 2 mm, and specifically from about 400 micrometers to about 1 mm. While the foam or other added particles may not be highly free flowing or perhaps not free flowing at all by its self, when combined with a sufficient quantity of free-flowing particles the combination can display free flow properties nonetheless. In other embodiments, one or more kinds of nits can be combined with other particles such as microspheres, spherical minerals, coated particles, and the like.

Incorporation into Absorbent Articles

Following drying and other processing steps in the preparation of nits or other free-flowing particles, the particles are incorporated into an absorbent article for the absorption of body fluids or other liquids. In one embodiment, nits comprising papermaking fibers can serve as the absorbent material in elongated absorbent pads for absorbing oil or other spilled liquids. Illustrative absorbent pigs are detailed in copending patent application Ser. No. 09/119602, "An Elongated Liquid Absorbent Pad and System for Collecting Leaks and Spills," filed Jul. 22, 1998 by J. D. Cotton, J. J. Tanner, and J. D. Lindsay, herein incorporated by reference in its entirety. In particular, free-flowing particles such as eucalyptus nits or sulfite softwood nits encased in an elongated liquid pervious web such as a spunbond web can form the interior absorbent material of an elongated absorbent pig suitable for containment of oil spills and other leaks in an industrial or workplace setting. The free-flowing particles allow the pig to conform to the surroundings, which are often irregular, in order to maximize leak prevention and absorption of fluids.

The free-flowing particles of the present invention can also be of value in many absorbent articles, particularly those adapted to conform to the body of a wearer, exploiting the ability of free-flowing particles to deform and flow in response to the presence of a body while still maintaining high void volume, even when wet. Thus, the free-flowing particles of the present invention could be used as an absorbent component in sanitary napkins (feminine care pads and related catamenial devices, including "ultra-thin" pads and pantiliners and maxipads), incontinence pads, diapers, menstrual pants, disposable briefs for children (training pants), breast pads, bed pads, sweat absorbing pads, helmet liners, body-contacting absorbents for ostomy bags, wound dressings, and the like.

Figure 2:
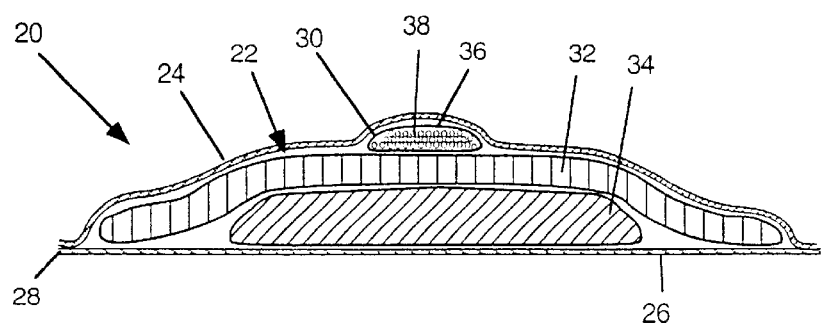
FIG. 2 depicts a sanitary napkin of the present invention in cross-sectional view showing an intake member comprising a longitudinal pouch of nits.

FIG. 2 depicts the cross-section along the transverse centerline of an absorbent article 20 which, in this embodiment, is a sanitary napkin having a longitudinal direction normal to the cross-section shown. The article 20 comprises an absorbent core 22 disposed between a topsheet 24 and a liquid impervious backsheet 26, the backsheet 26 being joined to the topsheet 24 at the periphery 28 of the sanitary napkin 20. The topsheet 24 can comprise any fluid pervious cover material known in the art, such as nonwoven webs or apertured films, or other materials such as hydrophilic wet laid basesheets treated with portions of hydrophobic matter, including those of Chen et al. in commonly owned copending application, "Dual-zoned Absorbent Webs", Ser. No. 08/997,287, filed Dec. 22, 1997, herein incorporated by reference.

The absorbent core 22 comprises a conformable intake member 30, an upper absorbent layer 32 and a lower absorbent layer 34. The conformable intake member 30 comprises a longitudinal pouch 36 of free-flowing particles 38 such as nits. The free-flowing particles 38 can be substantially free of superabsorbent particles or other powdered or granular materials, or can be combined with superabsorbent particles or other granular materials if desired.

In the embodiment depicted in FIG. 2, the upper absorbent layer 32 is transversely wider than the lower absorbent layer 34 such that the upper absorbent layer 32 is held in a convex upwards position, wherein inwardly lateral compression of the sanitary napkin 20 from the longitudinal sides by the legs of the wearer will tend to flex the upper absorbent layer 32 upward toward the body of the wearer, thus helping the conformable intake member 30 to be held in place against the body for good body fit and effective functioning as an intake member.

The upper absorbent layer 32 and the lower absorbent layer 34, as well as any other absorbent components apart from the free-flowing particles 38, can independently be any porous absorbent material known to be useful in sanitary napkins or other absorbent articles, such as one or more plies of wetlaid or airlaid tissue; cellulosic airlaid webs of comminuted fibers (commonly termed "airfelt"); other dry laid and airlaid webs; coform; creped cellulose wadding; peat moss; absorbent foams such as the hydrophilic polyether polyurethane foams of U.S. Pat. No. 5,914,125 and foams produced from high internal phase emulsions (HIPE) or other means, including those disclosed in U.S. Pat. No. 5,692,939, issued Dec. 2, 1997 to DesMarais, U.S. Pat. No. 5,851,648, issued to K. J. Stone et al., Dec. 22, 1998, or in U.S. Pat. No. 5,795,921, issued Aug. 18, 1998 to Dyer et al.; the foam-structured fibrous absorbent materials of F.-J. Chen et al. disclosed in the commonly owned, copending US patent application "Fibrous Absorbent Material and Methods of Making the Same," Ser. No. 09/083,873, filed May 22, 1998, herein incorporated by reference; absorbent sponges; synthetic staple fibers; polymeric fibers; hydrogel-forming polymer gelling agents, fiber-foam composites; absorbent nonwoven webs; cotton; wool; keratin fibers; or any equivalent materials or combinations of materials. The upper absorbent layer 32 and lower absorbent layer 34 can also comprise superabsorbent particles, fibers coated with or attached to superabsorbent particles, or other superabsorbent materials.

The nits can comprise papermaking fibers having at least 30% hardwood fibers and specifically at least about 30% eucalyptus fibers by weight, more specifically at least 60% hardwood fibers by weight. The nits can have an angle of repose of less than 72° and specifically less than about 60° in the dry state and in one embodiment, can still have angles of repose in the aforementioned ranges even at a moisture content of 50%.

The conformable intake member 30 can be elongated in the longitudinal direction of the article 20, and can have an aspect ratio of 2 or greater, more specifically about 3 or greater, more specifically still about 4 or greater, and most specifically from about 4 to about 8. The width of the conformable intake member 30 can be about 2 cm or greater, or less about 5 cm or less or more specifically about 4 cm or less, while having a length of about 8 cm or greater, more specifically about 10 cm or greater, and most specifically about 15 cm or greater. The same dimensional considerations can be applied specifically to the pouch 36 itself, as well.

Apart from the added thickness contributed by the pouch of particles 38, the thickness of the absorbent article 20 can be from about 2 mm to about 50 mm, more specifically from about 3 mm to about 25 mm, more specifically still from about 3 mm to about 15 mm, and most specifically from about 4 mm to about 10 mm. Ultrathin articles can have a thickness less than about 6 mm.

Various types of free-flowing particles 38 can be incorporated into one or more discrete pouches 36 in the article or can be mixed together uniformly or in gradient form. Principles and equipment for mixing free-flowing particles are described by B. H. Kaye in "Mixing of Powders," Chapter 11 in *Handbook of Powder Science and Technology*, ed. by M. E. Fayed and L. Otten, $2^{nd}$ ed, Chapman & Hall, New York, 1887, pp. 568–585.

The pouch 36 can be a nonwoven web or tissue web adapted to fully enclose the free-flowing particles 38. However, it need not be a single material forming a complete encasement or envelope for the particles 38, but can be formed by the interaction of a plurality of webs or absorbent layers to define a sealed volume capable of enclosing free-flowing particles 38. For example, a pouch 36 can be formed by the interaction of a backsheet 26, an outer absorbent member 42 comprising a central void 44 for receiving free-flowing particles, and a topsheet 24, whereby attachment of the various components serves to prevent the free-flowing particles 38 from escaping the article 20.

In one embodiment, the article 20 comprises a pocket of substantially loose absorbent material comprising a first type of free-flowing particles 38 and a second type of particles (not shown) to obtain a balance between various properties such as ability to flow freely when dry or when wet, absorbency, conformability, ability to resist bunching, etc. A third type of particles (not shown) or even more types of particles can also be present. In one embodiment, the first type of particles 38 is hardwood nits, optionally comprising 50% or more of the mass of the absorbent material in the pocket. The second type of particles can be other cellulosic nits, such as, for example, softwood nits having a substantially larger particle size than the first type of particles. The second type of particles, like the first type, can be treated with a small quantity (e.g., less than 5% by dry mass, or less than 1% by dry mass) silicones or other hydrophobic materials optionally residing primarily on the surface of the particles to help prevent sticking or clumping of particles when wet. Thus, in one embodiment, the central absorbent member 46 comprises loose nits of fibrous material comprising a first type of free-flowing particles 38 and a second type of free-flowing particles, substantially distinguished in a material property selected from fiber type, mean particle size (determined by sieve analysis according to American Society for Testing and Materials (ASTM) test method D-1921), ash content, chemical additive content, Water Retention Value, and wetting angle of the surface of the particles. Superabsorbent particles and odor control materials can be present as the second type or third type of particles or as a portion of a mix or composite comprising the second or third type of particles. When superabsorbents or hydrogel-forming materials are incorporated with nits, they can be present in an amount greater than 0 to less than 100 weight percent, specifically from about 5 to about 95 weight percent, more specifically from about 15 to about 85 weight percent, and more specifically still from about 20 to about 50 weight percent, based on the total weight of the superabsorbent or hydrogel-forming polymeric material and nits in the absorbent composition. In one embodiment, less than about 10% superabsorbent particles are present for nits treated with hydrophobic material, in order to help maintain a free flowing nature of the nits even when wetted.

In one embodiment, nits or other free-flowing particles 38 such as hollow spheres are combined with deformable particles having, by way of example only, a particle size of about 2 mm or less, more specifically about 0.7 mm or less, including pieces of a soft foam such as a polyurethane foam or foam rubber material. Rounded particles can be used. The soft, deformable particles combined with the can help improve the tactile properties of the filled pouch 36, allowing a softer feel and more comfort when worn against the body. In general, the free flowing particles 38 for use in any of the absorbent members of the present invention can be combined with one or more deformable materials, particularly in particulate form, for improved comfort and avoidance of a grainy feel, especially when larger sized free-flowing particles are used.

The topsheet 24 can be any material known to be useful as topsheets in absorbent articles. Exemplary topsheets can be made in accordance with U.S. Pat. No. 5,533,991, issued Jul. 9, 1996 to Kirby et al.; U.S. Pat. No. 4,342,314 issued Aug. 3, 1982 to Radel et al. and U.S. Pat. No. 4,463,045 issued Jul. 31, 1984 to Ahr et al. The topsheet 24 may comprise an additional transfer layer (not shown) to help direct fluid into the absorbent core 22, as disclosed, for example, in U.S. Pat. No. 4,397,644, issued Aug. 9, 1983 to Matthews et al. The topsheet 24 may comprise one or more layers of microdenier fibers, such as those disclosed in European Patent Application 893,517-A2, "Micro-Denier Nonwoven Materials Made Using Modular Die Units," A. Fabbricante, et al., published Jan. 27, 1999. The topsheet 24 need not have uniform properties but can be preferentially more permeable or liquid pervious or wettable over the central absorbent member than it is elsewhere.

The backsheet 26 may be any flexible, liquid impervious material that prevents discharges collected by the absorbent article 20, such as a sanitary napkin, from escaping the article 20 and soiling the undergarments and clothing of the wearer.

The backsheet 26 and other components may be biodegradable and/or flushable. A flushable article is one that can be directly discarded into a toilet and flushed without clogging piping and without harm to septic systems. The backsheet 26 may also be extensible or elastically deformable for use in extensible absorbent articles. Any methods known in the art for production of elastic or stretchable films or cover sheets may be used, including those disclosed in U.S. Pat. No. 5,702,378, issued to Widlund et al., Dec. 30, 1997 and in U.S. Pat. No. 5,824,004, issued Oct. 20, 1998 to Osborn, III et al.

Figure 3:
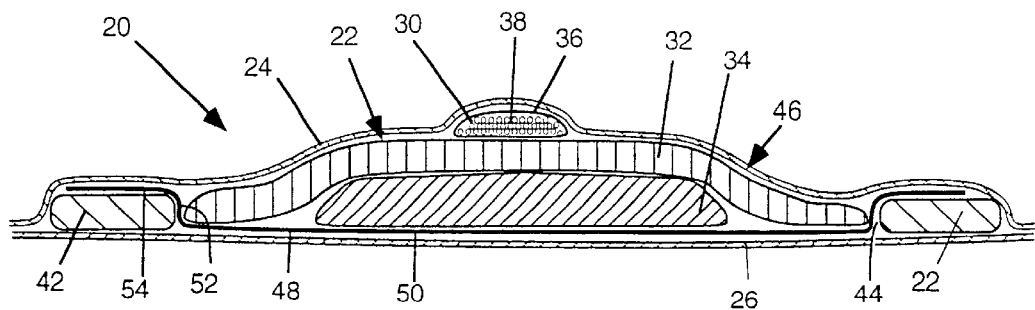
FIG. 3 is a cross-sectional view of an absorbent article of the present invention with a conformable intake member comprising free-flowing particles and further comprising a wicking barrier to impede fluid flow from a central absorbent member to an outer absorbent member.

FIG. 3 depicts an absorbent article 20 related to that of FIG. 2 and generally follows the number scheme of FIG. 2. However, the absorbent core 22 of the absorbent article 20 further comprises an outer absorbent member 42 with a central void 44 therein for receiving the lower absorbent layer 34 and the upper absorbent layer 32, which, together with the conformable intake member 30 form a central absorbent member 46 that is laterally surrounded by the outer absorbent member 42. The central absorbent member can comprise from 0.5 grams to about 10 grams of dry nits, specifically from about 2 grams to 5 grams, and can comprise from about 0 grams to 5 grams of superabsorbent particles or fibers.

A wicking barrier 48 separates the outer absorbent member 42 from the central absorbent member 46. The wicking barrier 48 is a section of polymeric film or other flexible, hydrophobic or liquid impervious material to help contain fluid within the central absorbent member 46 and to reduce lateral flow therefrom to the longitudinal sides of the article 20. For example, the wicking barrier 48 can be a polyolefin film, a fluid-resistant nonwoven web, a tissue treated to be hydrophobic, or the transfer delay barrier materials disclosed in the commonly owned US patent application Ser. No. 60/079,657, "An Absorbent System for Personal Care Products Having Controlled Placement of Visco-Elastic Fluids" by A. S. Burnes et al., herein incorporated by reference.

The wicking barrier 48 is optionally provided with apertures for controlled release of fluid from the central absorbent member 46 to the outer absorbent member 42. As depicted, the wicking barrier 48 has an underlying portion 50 beneath the lower absorbent layer 34, a vertical component 52 spanning a vertical distance between the outer absorbent member 42 and the central absorbent member 46, and a horizontal component 54 spanning a horizontal distance on or above the body-side surface of the outer absorbent member 42. The wicking barrier 48 helps prevent fluid communication between the outer absorbent member 42 to the central absorbent member 46 not only by impairing lateral wicking, but by obstructing contact between the two absorbent members 42, 46 when the article 20 is worn and laterally compressed. The Intrinsic Absorbent Capacity of the barrier material can be about 1 or less, more specifically less than about 0.5, more specifically still less than about 0.3, and most specifically less than about 0.1. The material of the wicking barrier 48 can be substantially non-absorbent.

The outer absorbent member 42 can be a contiguous piece of absorbent material with a central hole, or can be two longitudinal strips of absorbent material wherein the central void 44 is defined by the space between the two strips.

Figure 4A:
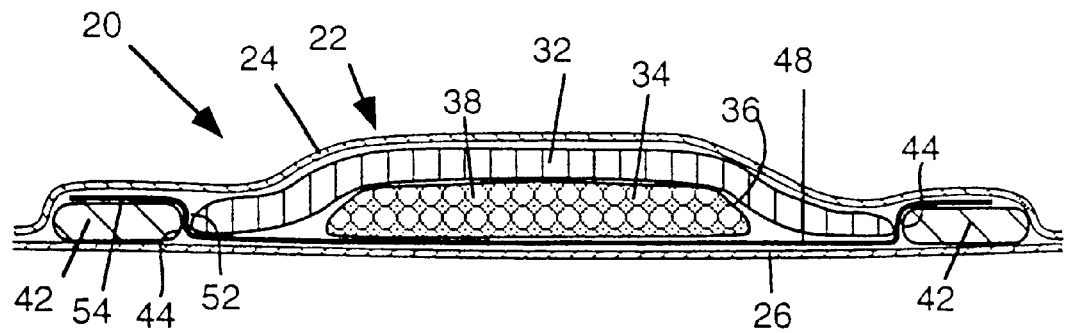
FIGS. 4A and 4B depict cross-sectional views of two versions of an absorbent article having a pouch of nits or free-flowing particles beneath an upper absorbent layer, wherein the pouch helps predispose the upper absorbent layer for upward flexing when the article is worn.
Figure 4B:
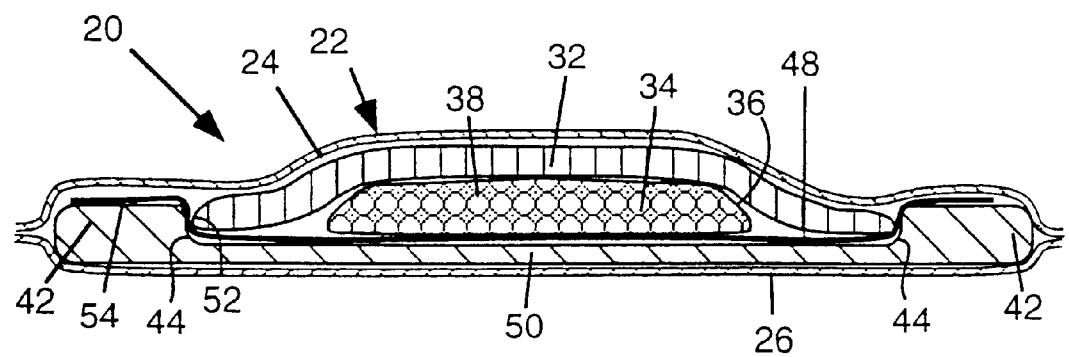

FIGS. 4A and 4B depict the transverse cross-section of an absorbent article 20 also comprising a central absorbent member 46 comprising an upper absorbent layer 32 and a pouch 36 comprising free-flowing particles 38 in a pouch 36 disposed beneath the upper absorbent layer 32; an outer absorbent member 42 having a central void 44 for receiving the central absorbent member 46; a wicking barrier 48 disposed between the central absorbent member 46 and the outer absorbent member 42. The pouch 36 is narrower than the upper absorbent layer 32. The upper absorbent layer 32 therefore assumes a convex upward shape predisposed to flex toward the body of the wearer during inwardly lateral compression from the longitudinal sides of the article 20.

The wicking barrier 48 extends below the pouch 36 of free-flowing particles 38 and has a vertical component 52 spanning a vertical distance along the inner walls of the central void 44 of the outer absorbent member 42, and further has a horizontal component 54 spanning a horizontal distance on the body-side surface of the outer absorbent member 42. The wicking barrier 48 can comprise multiple sections, such as two strips of polymeric film or two strips of a substantially liquid impervious nonwoven web extending along the longitudinal sides of the upper absorbent layer 32 to hinder wicking between the central absorbent member 46 and the outer absorbent member 42.

In FIG. 4A, the outer absorbent member 42 is divided along the transverse centerline by a central void 44 passing completely through the outer absorbent member 42, while in FIG. 4B, the outer absorbent member 42 is not divided but comprises a relatively thinner underlying portion 50 beneath the central absorbent member 46 and joining the two longitudinal sides of the outer absorbent member 42 along the transverse centerline. In FIG. 4B, the central void 44 is a depression and not a hole passing completely through the outer absorbent member 42. Thus, the pouch 36 can be disposed between two or more layers of absorbent material or particle restraining material (including the wicking barrier 48), in which case the free-flowing particles 38 can be restrained by the surrounding materials without the need for the pouch 36 depicted in the embodiment of FIG. 4B.

Figure 5:
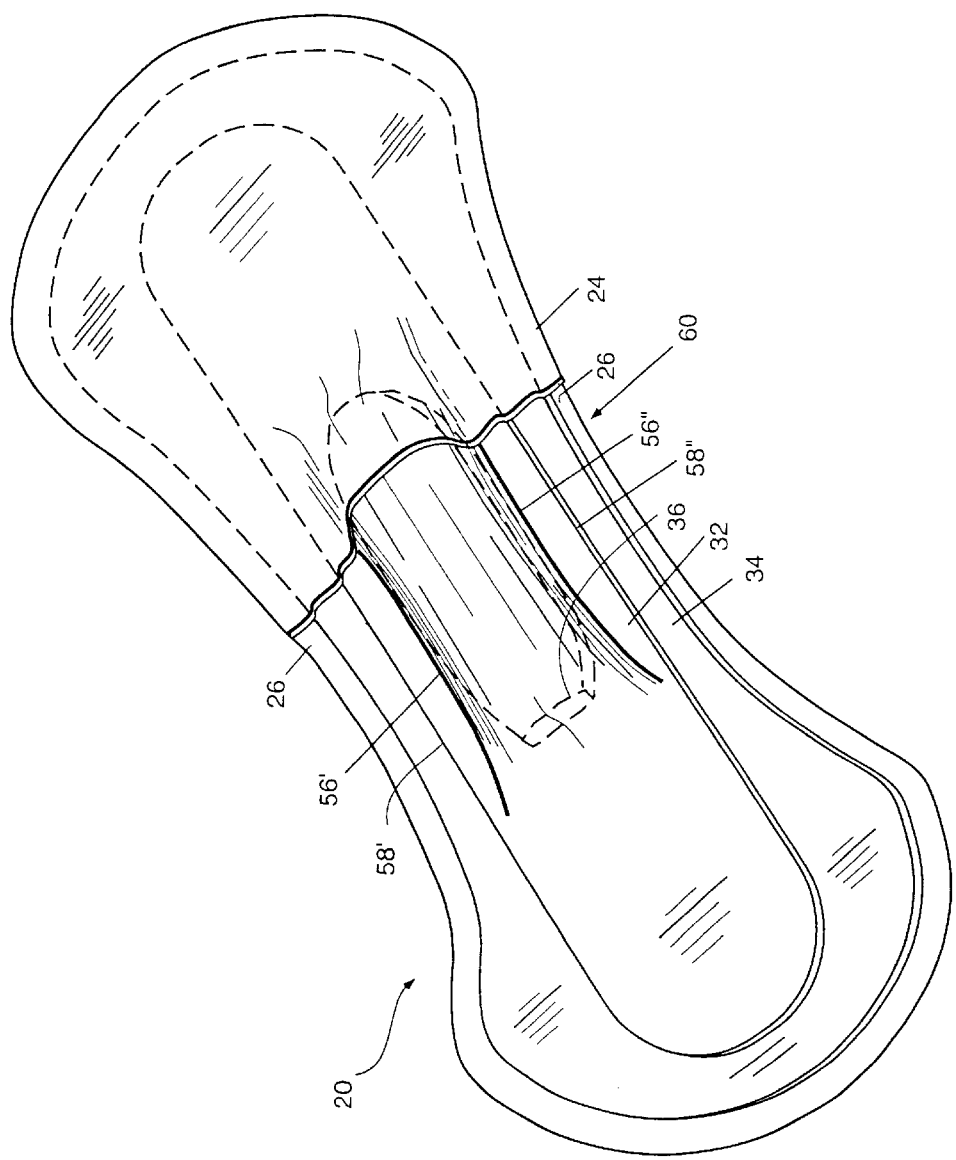
FIG. 5 is a partial cutaway view of a sanitary napkin comprising a pouch of nits or free-flowing particles disposed between two absorbent layers.

FIG. 5 is a partial cutaway view of an absorbent article 20 according to the present invention. The article 20 comprises a topsheet 24, which is cut away to reveal several underlying components, particularly an upper absorbent member 32, which has a medial hump therein due to the presence of an underlying pouch 36 of free-flowing particles, depicted here in a truncated oval shape having a thickness substantially greater than the thickness of the upper absorbent member 32. The upper absorbent member 32 further comprises a pair of optional, substantially longitudinal crease lines 56', 56" in the crotch region 60, the crease lines 56', 56" being spaced apart about the longitudinal centerline of the article 20. The crease lines 56', 56" are transversely outside the longitudinal sides of the pouch 36 and within the longitudinal sides 58', 58" of the upper absorbent member 32. The crease lines 56', 56" also extend into the underlying lower absorbent member 34, which also has a thickness substantially lower than the pouch 36 of free-flowing particles in this embodiment. Thus, the crease lines 56', 56" in both the upper absorbent member 32 and the lower absorbent member 34 permit upward folding of the outer longitudinal sides of the lower absorbent member 34 and the upper absorbent member 32 to form a valley fold when the absorbent article 20 is laterally compressed inward by the legs of the user when worn, while the elevated pouch 36 helps contribute to the formation of a central mound when compressed laterally inward to give an overall W-shape to the article 20 (with the central part of the W-shape in one embodiment being substantially rounded).

In one embodiment, the upper absorbent member 32 and the pouch 36 can partially separated from the lower absorbent member 34 by a horizontal wicking barrier (not shown).

Figure 6A:
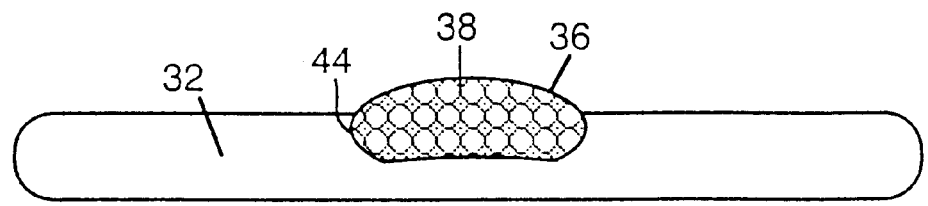
FIGS. 6A–6C depict embodiments in which a central pouch of nits or free-flowing particles disposed on an absorbent layer can serve as a conformable intake member.
Figure 6B:
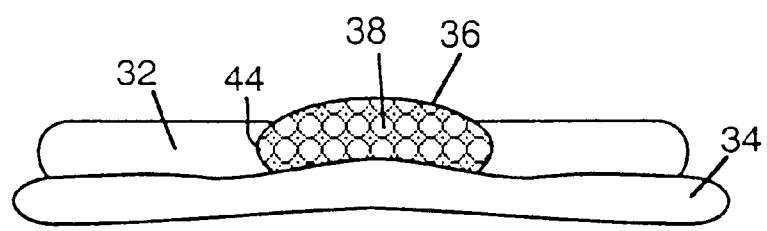
Figure 6C:
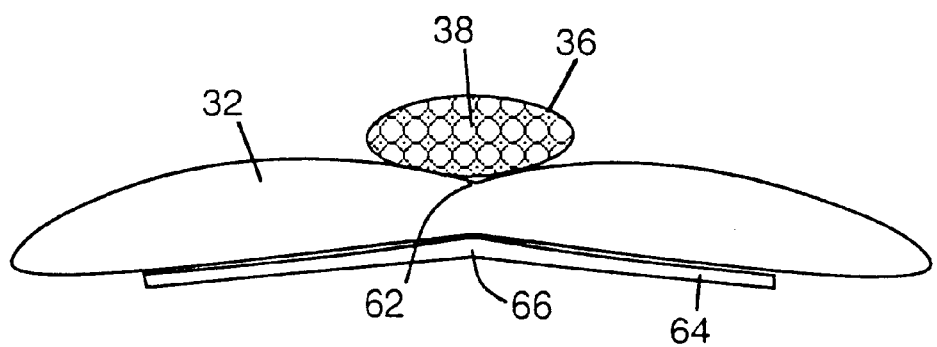

FIG. 6 depicts cross-sectional views along transverse centerlines of absorbent articles showing several ways in which a pouch 36 of nits or other free-flowing particles 38 can serve as a conformable intake member disposed on an upper absorbent layer 32. In FIG. 6A, the pouch 36 is disposed in a central void 44 within the upper absorbent layer 32. In FIG. 6B, the pouch 36 is disposed in a central void 44 passing completely through the upper absorbent layer 32, with second layer, the lower absorbent layer 34 beneath the pouch 36. The lower absorbent layer 34 is preshaped to have a convex upward shape to predispose it to flex upward when inwardly laterally compressed, thus directing the pouch 36 toward the body. In FIG. 6C, the upper absorbent layer 32 is preshaped for upward deflection when inwardly laterally compressed from the longitudinal sides. The upper absorbent layer 32 has a central shaping line 62 where the lower absorbent layer 34 has been scored, folded, stamped, embossed, or the like to promote upward flexure. A resilient deflection element 64 comprising a central hinge 66 is further disposed beneath the upper absorbent layer 32 to further control the deflection of the absorbent article toward the body of the wearer when the article is worn.

Figure 7:
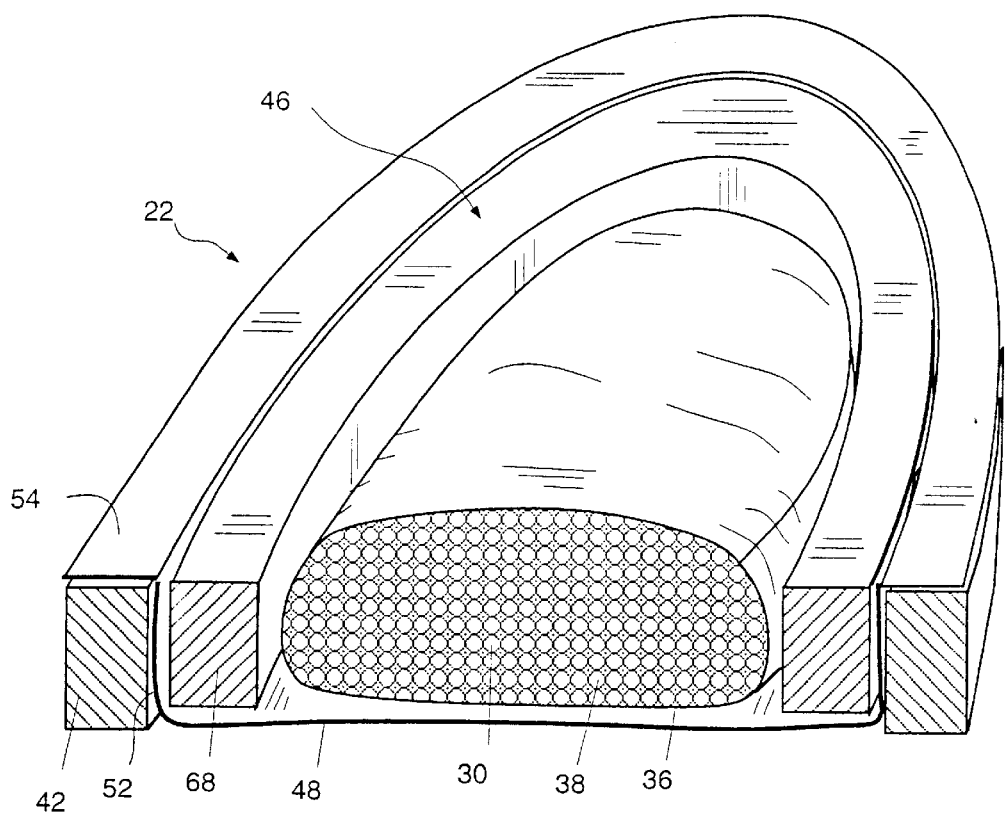
FIG. 7 depicts a cutaway view of an absorbent core comprising a wicking barrier and a central absorbent member having an internal pouch of free-flowing particles.

FIG. 7 shows a partial cutaway view of an absorbent core 22 for use in an absorbent article (not shown) according to the present invention. The absorbent core 22 comprises an outer absorbent member 42 having a central elliptical hole therein for receiving a central absorbent member 46. The outer absorbent member 42 can be an outer annular ring of absorbent material. The central absorbent member 46 comprises an inner annular ring 68 of absorbent material with an inner void therein, and a conformable intake member 30 comprising nits or free-flowing particles 38 in a liquid-pervious pouch 36 which prevents particles from escaping the conformable intake member 30.

Between the outer absorbent member 42 and the central absorbent member 46 is a wicking barrier 48, which comprises a vertical component 52 and a horizontal component 54 on or above the body-side surface of the outer absorbent member 42.

Figure 8:
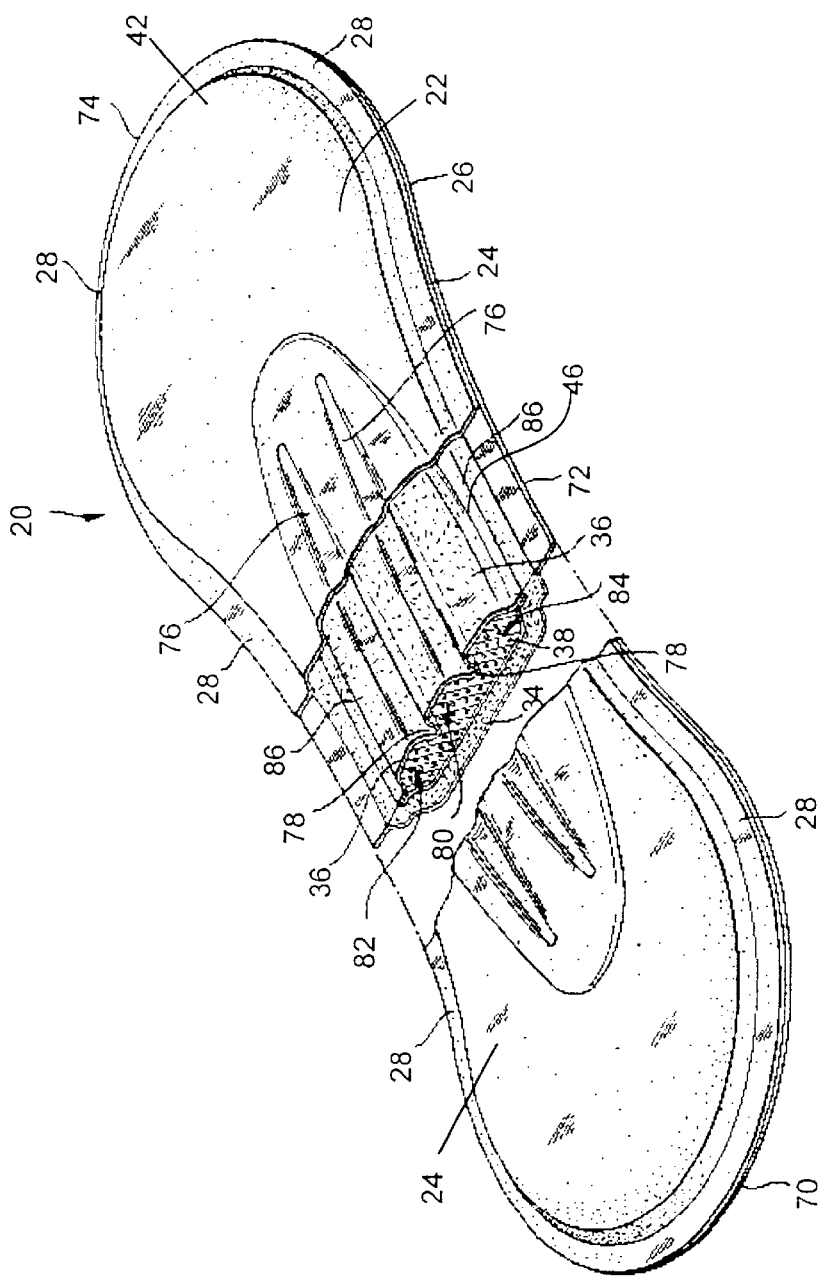
FIG. 8 depicts a partial sectional view of a pad comprising a central pillow filled with nits and/or other free-flowing particles.

FIG. 8 shows a "pillow pad" design based on the Raidel patent application (WO 98101684), adapted according to the present invention to comprise nits. FIG. 7 shows a pad 20 in partial section view. The pad 20 comprises a frontal region 70, a middle region 72 and a rear region 74. A liquid-pervious layer topsheet 24 and a liquid-impervious backsheet 26 are joined together at the periphery 28. The absorbent core 22 comprises a central absorbent member 46 and an outer absorbent member 42. The central absorbent member 46 comprises a pouch 36 containing cellulosic nits 38 therein. The pouch 36 may be made from a nonwoven web.

In the embodiment shown in FIG. 8, the pouch 36 is almost entirely filled with free-flowing particles 38 such as nits. Complete filling with nits does not pose any serious problem in use since the nits do not expand substantially upon wetting. If substantially swellable materials were also present, such as superabsorbent particles, the pouch 36 can be only partially filled with absorbent material to prevent rupture. Alternatively, the pouch 36 can comprise elastomeric material or pleats or folds that can allow the pouch 36 to expand when the free-flowing particles 38 and other absorbent materials inside the pouch 36 are wetted.

Grooves 76 extend in the longitudinal direction of the article 20. The pouch 36 of the absorbent core comprises tied-in areas 78 which cause a degree of separation of the pouch 36 into a central chamber 80 and lateral chambers 82, 84. The delimitation walls of the individual chambers do not reach all the way to the base of the pouch 36, so that a limited degree of material exchange can occur between the individual chambers.

As shown in FIG. 8, the pouch 36 comprises two sections which are interconnected at the peripheral margins 86 of the pouch 36. This construction facilitates filling of the absorbent core 22 with free-flowing particles 38 because a lower half of the pouch 36 can be filled with particles, and then an upper half can be placed over the lower half of the pouch 36 to seal the free-flowing particles 38.

The pouch 36 depicted in FIG. 8 is substantially oval in shape and is backed by additional absorbent material in a lower absorbent layer 34 of the central absorbent member 46. The lower absorbent layer 34 contributes to wearer comfort and to absorbency of the absorbent core 22.

A wicking barrier (not shown) may also be present between the central absorbent member 46 and the outer absorbent member 42. The lower surface of the lower absorbent layer 34 may comprise a polymeric film which can extend past the peripheral margins 86 of the central absorbent member 46 such that some of the wicking barrier also extends on the body-side surface of the outer absorbent member 42 in the middle region 72 (crotch region) of the absorbent article 20 for improved leakage control.

Without wishing to be bound by theory, it is believed that when the article 20 comes into contact with menses or blood, the grooves 76 help distribute the fluid longitudinally, after which fluid can be taken up by the free-flowing particles 38 in the pouch 36. The grooves 76 are also believed to provide increased transverse flexibility of the absorbent article 20, providing for good body fit and comfort, while reducing the effective size of any one chamber 80, 82, 84, such that shifting of the particles 38 is not a serious problem.

FIGS. 9 and 10 were previously discussed in relation to the Angle of Repose test.

FIGS. 11 and 12 were previously discussed in relation to the Gel Bed Permeability test.

Figure 13:
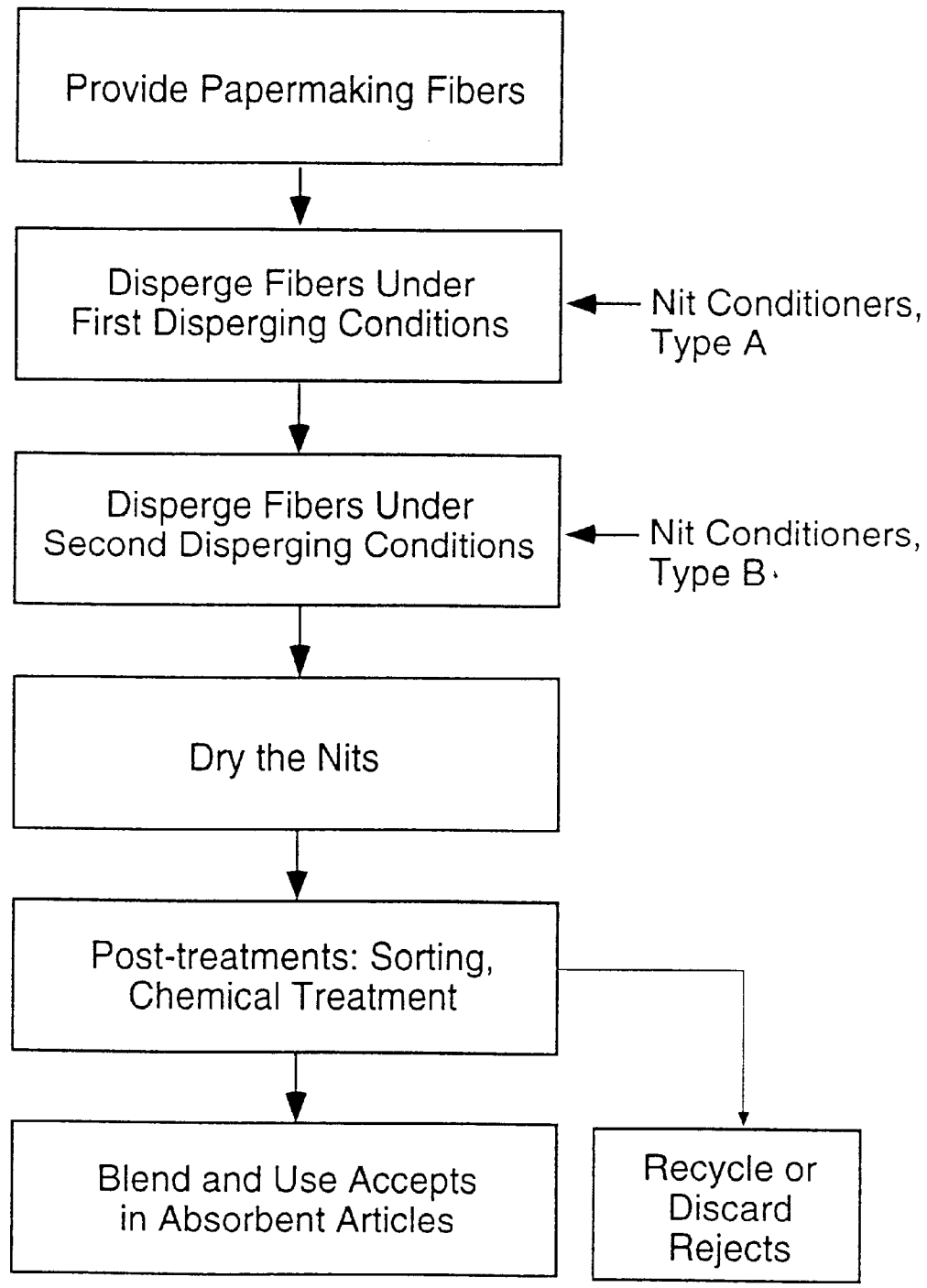
FIG. 13 is a flowchart for a method of preparing absorbent articles comprising nits that have been disperged twice.

FIG. 13 depicts a flowchart for a process of making nits in which the stream of fibers is disperged more than once, allowing modifications in chemistry and process conditions to permit improved control over nit properties in the two or more separate steps. It has been discovered that a second step of dispersing can help improve the flowability and absorbency properties of the nits. Thus, hardwood fibers or a slurry comprising hardwood fibers can be substantially curled or formed into nits in a first disperging operation, such as by treatment with a Maule disperger, a BIVIS disperger, a disk disperger, or other suitable equipment capable of curling and dispersing high-consistency wood pulp. The mechanically treated fibers or nits can then be optionally dried, followed by adjustment of the moisture content to bring the consistency to about 18% or greater, or 20% or greater, such as from 20% to 30%. Thereafter the fibers are again subjected to disperging at a suitable energy level to create nits, which are then dried. For example, a Maule shaft disperger can be used to create nits in a first step with an exit consistency of about 30% or higher, whereafter the consistency is reduced to from about 20% to about 30% for further mechanical processing in a Hobart mixer for high-consistency pulp. Without wishing to be limited by theory, it is believed that a second disperging step under different processing conditions (different consistency or different mechanical equipment) can create new shear conditions that may help remove free fibers projecting from the surface of nits formed in the first step, fibers that may not have been sufficiently able to become entangled into the nit under the conditions of the first treatment.

The use of two or more disperging steps provides increased flexibility to achieve specific objectives. For example, nit conditioners and disperger conditions in the first disperging step may be designed to control flock formation and the initial size of the nits to maximize yield in a desired size range. The second dispersing step may further improved the size distribution and may use different chemistry aimed at modifying the surface of the nits rather than the body of the nits. In this way improved control over nit properties is possible.

In addition, without wishing to be bound by theory, it is believed that drying or partial drying after a first disperging step, followed by remoistening, a second disperging step, and final drying, can promote hydrogen bonding of previously loose fibers with the parent nits such that the fibers are no longer projecting from the nits to the degree before. By remoistening partially dried nits and drying the nits again, new hydrogen bonds can form between loose fibers and the other fibers in the nits from which the loose fibers project. If the nits are simply wetted and redried, new hydrogen bonds may form between projecting fibers and other nits, resulting in clumps. Disperging or mechanical shear is needed after rewetting to separate the nits and promote bonds between fibers in the same nit rather than bonds between nits. Following the second dispersing step, entanglements between adjacent nits will have been largely disrupted by the mechanical action and tighter, denser nits will have been formed. Drying can then be completed, optionally with pneumatic or mechanical agitation to prevent additional clumping.

Further, the use of two or more disperging steps offers additional combinations of temperature and chemistry to control the properties of the nits. For example, the first disperging step may be done at an elevated pH (e.g., pH above 8, such as from 9 to 11), wherein the fibers are swollen and relatively flexible. Then the second disperging step may be performed under lower pH, such as a pH of from about 4 to 6, wherein the swelling of the fibers are reduced and the ability of the fibers to collapse into nits may be enhanced. Benefits can also be obtained by the reverse procedure, in which a first disperging step is conducted at low pH, followed by a second step at elevated pH, with the potential to produce nits that are relatively more round or that have other desired morphological properties.

By disperging nits in two or more stages, a first chemical can be added in a first disperging step, followed by addition of a second chemical in a second disperging step. This can be particularly helpful when the two chemicals would give undesired reactions when added simultaneously, such as an anionic compound and a cationic compound. For example, an anionic anti-microbial compound and a cationic wet strength agent or cationic debonder could be added in separate disperging steps. Or two charged compounds can be added that would normally interfere with each other or cause precipitation.

Figure 14:
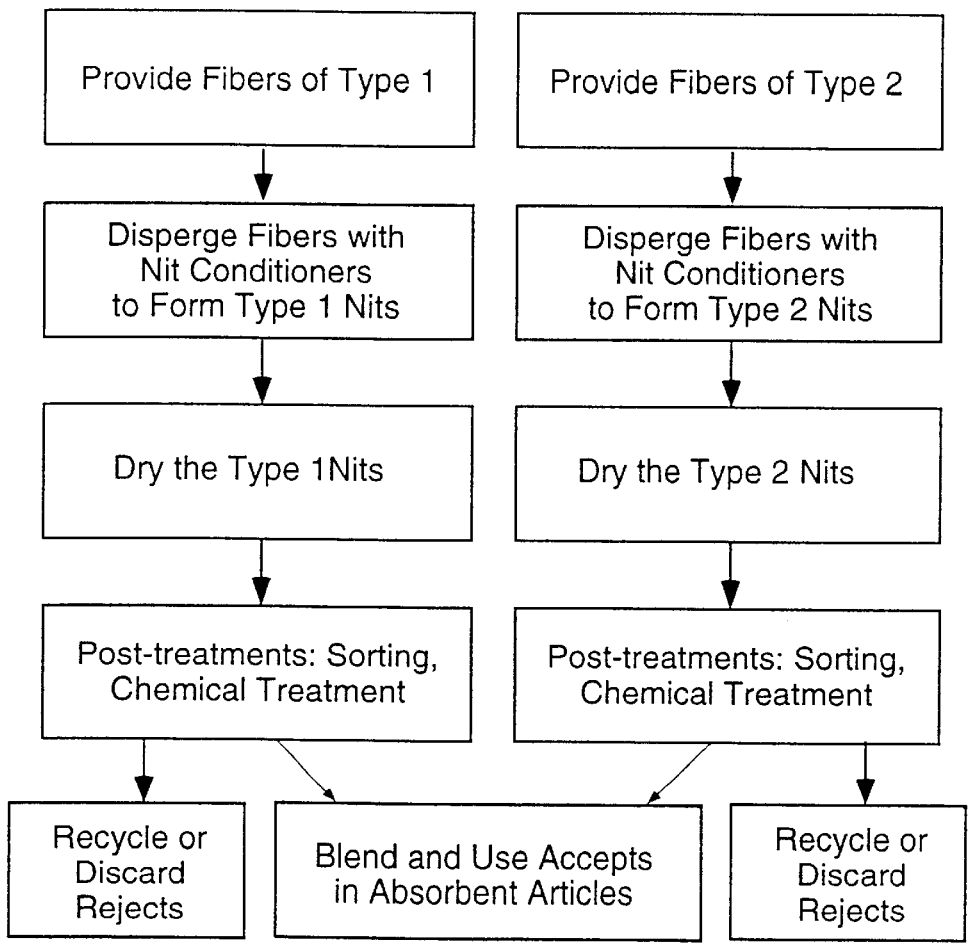
FIG. 14 is a flowchart for a method of preparing absorbent articles with two or more kinds of nits.

FIG. 14 depicts a flowchart for preparing an absorbent article comprising two or more kinds of nits. Nits of a first fiber type and a second fiber type are prepared via dispersing in the presence of nit conditioners and then dried, forming two material streams that can be independently exposed to post-treatments such as sorting by size by sieving, screening, or other classification methods, and such as chemical treatment, including deposition of hydrophobic matter on a portion of the outer surface of the nits. The nits can then be combined and used to fill a pouch in an absorbent article. Alternatively, the nits may be combined prior to any of the post-treatments or even prior to drying. When sorting by size or other properties occurs as a post-treatment, a fraction of the particle will be rejects that can be recycled (e.g., repulped and used in nits production, or used in other processes) or discarded. This can be generally true for all nits production methods of the present invention, even when not explicitly stated. The accepts are used to prepare the absorbent article.

Figure 15:
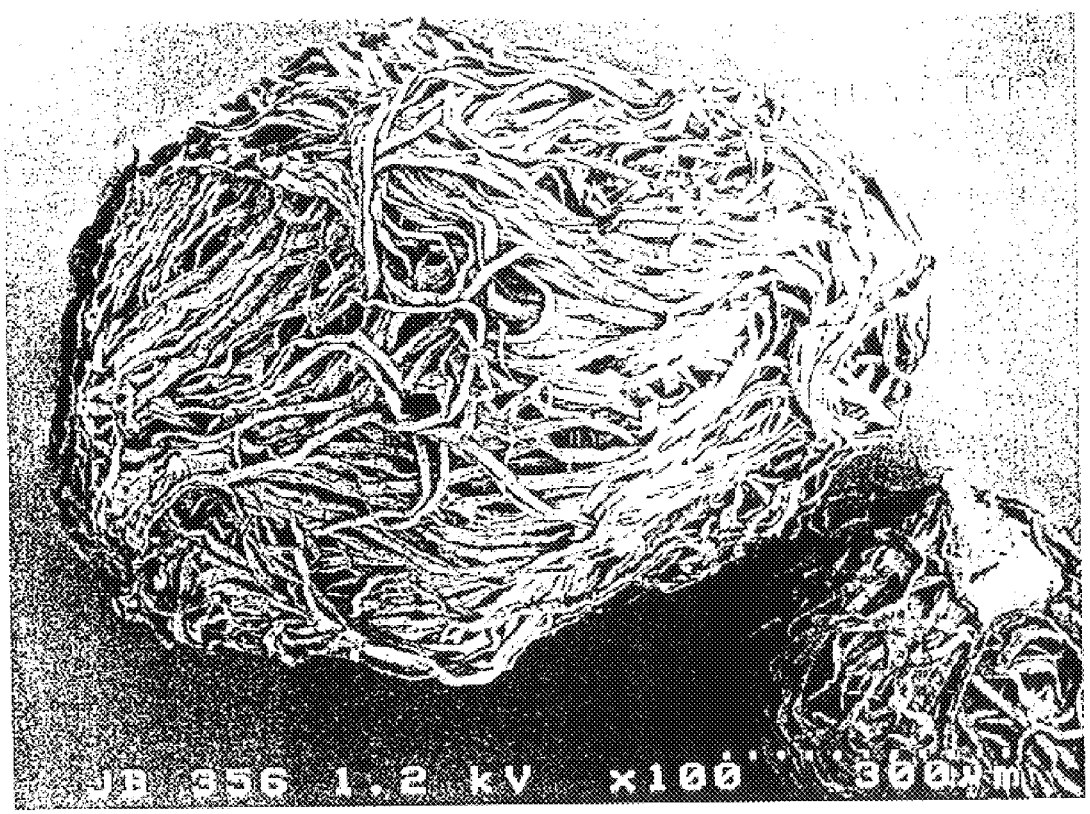
FIG. 15 is an SEM micrograph of a eucalyptus nit made according to the present invention.
Figure 16:
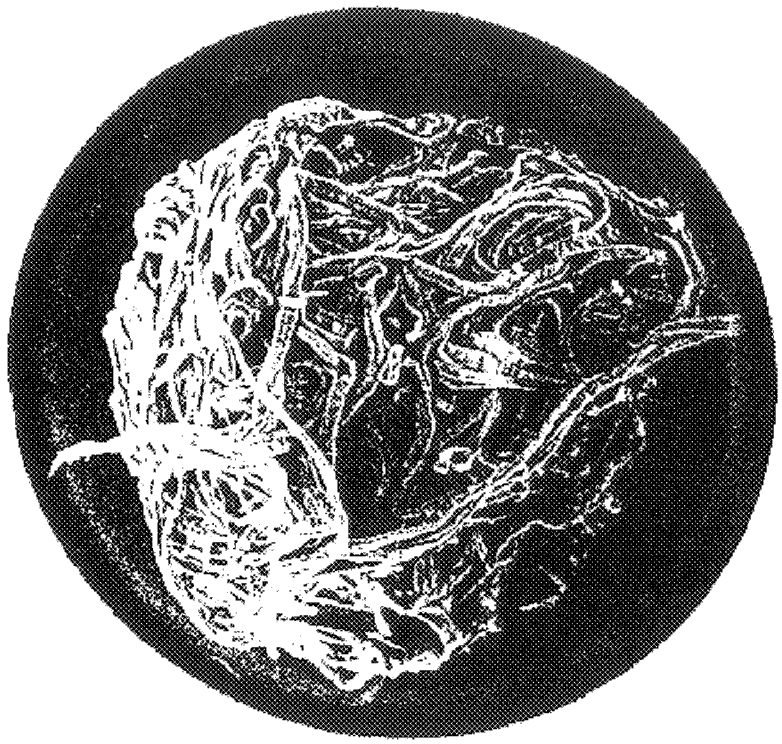
FIG. 16 is an SEM micrograph of a eucalyptus nit with fibers projecting from the surface of the nit.
Figure 17:
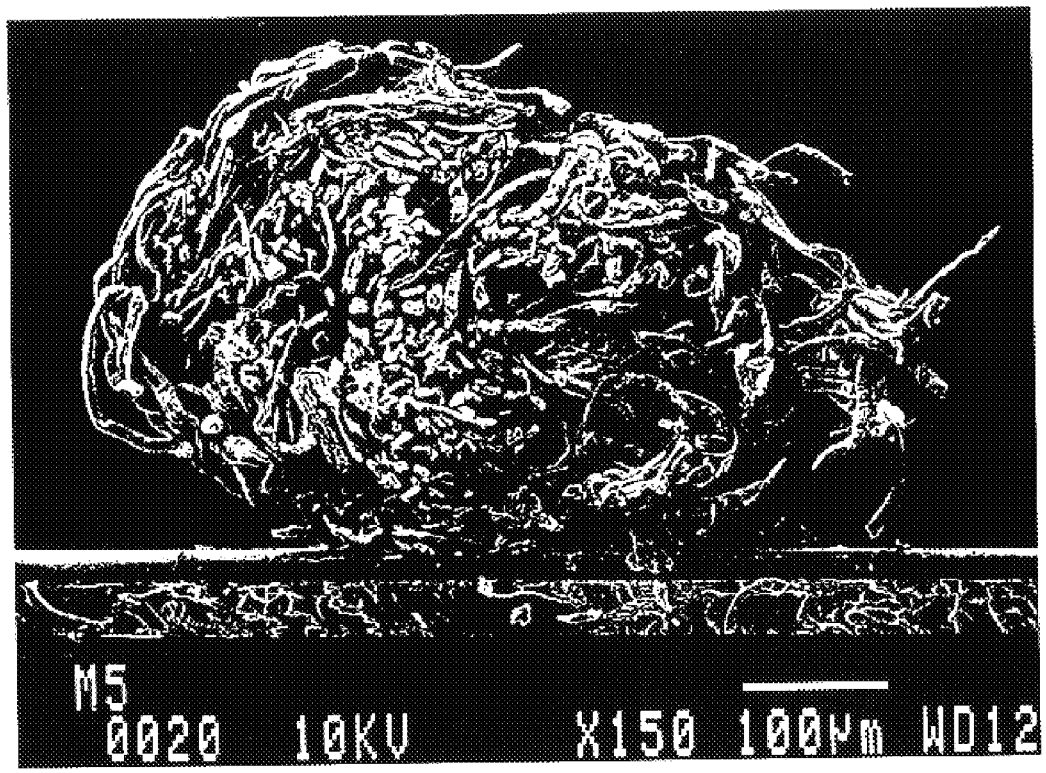
FIG. 17 is an SEM micrograph of the cross-section of a eucalyptus nit prepared with a Maule disperger.

FIGS. 15 to 17 show SEM micrographs of eucalyptus nits prepared according to conditions identified below in the Examples. FIG. 15 shows a rounded, ovoid nit substantially free of fibers ascending from the nit that could readily become entangled with other nits. The nit shown in FIG. 16 is still relatively free of fibers ascending from the surface, though it appears that two fibers do ascend. FIG. 17 is a cross-section of another eucalyptus nit produced with a Maule disperger, which was cut by a blade after being frozen in liquid nitrogen to reveal the interior structure.

Other Additives and Treatments

In one embodiment, known cationic retention aids are added to the pulp fibers prior to nit formation to promote and control floc formulation. Retention aids known in papermaking include a variety of cationic polymers such as polyacrylamides, cationic starch, modified guar gum, or dual-component retention aid systems, such as COMPOZIL® cationic polymer-colloidal silica microparticle systems, can be useful in controlling the size of nits formed from a papermaking slurry of wood fibers. Related principles are discussed by S. Main and P. Simonson in "Retention Aids for High-speed Paper Machines," *Tappi Journal*, Vol. 82, No. 4, pp. 78–84, herein incorporated by reference. For example, adding a cationic starch or polymer such as polyacrylamide to a pulp slurry followed by subsequent addition of anionic silica or other anionic compounds, according to Main and Simonson, can be effective in promoting formation of small, dense, flocs, which, in one embodiment, can be a useful treatment preparatory to forming the nits of the present invention. Compounds comprising certain metal ions, such as alum or ferric chloride, can also be useful in promoting and controlling floc formation.

The additives may be provided in the furnish prior to mechanical processing, or injected during the dispersing process or other mechanical treatments prior to drying, or applied to the exterior surface of the nits before, after, or during drying. For additives intended to improve lubricity and prevent clumping of the particles, the additives can be preferentially distributed on the surface of the particles, so the additive in pure form or as a solution can be applied to the exterior of the particles after their formation and optionally during or after the drying process. Additives may be applied by spray, by contact with a wetted surface, by trickling of a stream into a mixed bed of particles, and the like. The additives may be applied uniformly or nonuniformly to the surface of treated particles, and all or suitable only a portion of the particles may be treated. In one embodiment, from 5% to 90% of the particles are treated, specifically from about 10% to 70%, more specifically from 10% to 50%, and most specifically from about 10% to about 30% of the particles are treated.

In one embodiment, nits are disperged with added ammonium zirconium carbonate, such as 0.3 to 3 weight percent based on dry fiber mass, followed by treatment at elevated temperature (greater than 100° C.), optionally in a fluidized bed or high shear air drier, to crosslink the fibers inside the nits but not between the nits, maintaining a loose bulk structure in the dried product. Ammonium zirconium carbonate can act as a crosslinker and can impart lubricity, promoting a free-flow behavior in the nits and optionally contributing to useful tactile properties. Minerals and fillers such as clays and zeolites may also be added to the fibers in making nits, for odor control, absorbency control, antimicrobial control, or other purposes.

In another embodiment, the nits are treated with both a debonder and crosslinking agent. Specifically, it is within the scope of the invention to add both a debonding agent a latent crosslinking agent to the pulp prior to completion of drying of the nits. Without wishing to be bound by theory, a beneficial interaction between debonders and crosslinkers in some embodiments may be expected due the ability of debonders to promote formation of nits in a useful size range while crosslinkers can further enhance the ability of nits to maintain their shape and size when wetted, or can be used to attach or retain desired additives in the nits. Useful principles for treatment of pulp or fibers with debonders and crosslinkers are described in U.S. Pat. No. 5,225,047, "Crosslinked Cellulose Products and Method for Their Preparation," issued to Graef et al., Jul. 6, 1993, herein incorporated by reference. Likewise, a beneficial interaction between surfactants and crosslinkers is expected, according to the present invention.

In one embodiment, the debonding agent or surfactant is added to the pulp prior to the addition of the latent crosslinking agent. The latent crosslinking agent can be added to cellulose while it is at a moisture content greater than about 10%, more specifically greater than about 30%. Crosslinking is substantially completed during subsequent drying or after drying in an additional curing step at elevated temperature.

The latent crosslinking agent may be selected from any of the following well known materials which serve this function. Types are selected from urea derivatives such as methylolated urea, methylolated cyclic ureas, methylolated lower alkyl substituted cyclic ureas, dihydroxy cyclic ureas, lower alkyl substituted dihydroxy cyclic ureas, methylolated dihydroxy cyclic ureas, and mixtures of any of these types. One latent crosslinking material is dimethyloldihydroxyethyleneurea (DMDHEU, 1,3-dihydroxymethyl-4,5-dihydroxy-2-imidazolidinone). This material is readily commercially available in a stable form. Other urea-based materials which are eminently suitable include dimethylol urea (DMU, Bis[N-hydroxymethyl]urea), dihydroxethyleneurea (DHEU, 4,5-dihydroxy-2-imidazolidinone), dimethylolethylene area (DMEU, 1,3-dihydroxymethyl-2-imidazolidinone), and 4,5-dihydroxy-1,3-dimethyl-2-imidazolidinone (DDI, dimethyldihydroxyethyleneurea).

In addition to those latent crosslinking agents based on urea, other materials that are suitable are polycarboxylic organic acids. Among these is 1,2,3,4-butanetetracarboxylic acid.

All of the crosslinking agents just described may be reacted with the cellulose either during normal drying of the sheeted material or subsequent to this time by raising the pulp or nits to an elevated temperature, typically above 100° C.

A neutral or acidic catalyst may be included with the latent crosslinking agent to increase the reaction rate between the crosslinker and the cellulose. Acidic salts are particularly useful as catalysts when the urea-based materials are employed. These salts may typically be ammonium chloride or sulfate, aluminum chloride, magnesium chloride or mixtures of these or many other similar materials. Alkali metal salts of phosphorous-containing acids, such as sodium hexametaphosphate and sodium hypophosphite, with or without additional oxalic acid, are useful catalysts for 1,2,3,4-butane carboxylic acid.

The crosslinking agent is typically present in an amount in the range of about 0.1% to about 15% (weight percent based on the mass of dry fiber), specifically from about 0.3% to about 6%, and more specifically from about 0.5% to about 3%. Similarly, the debonding agent is generally present in an amount of about 0.1% to about 10% (weight percent based on the mass of dry fiber), specifically from about 0.3% to about 4%, and more specifically from about 0.5% to about 2%. Generally, there will be no need for washing of the pulp after the crosslinking reaction is completed.

In one embodiment, the conversion of fibers into dense, free flowing nits can be achieved using two or more steps of disperging or kneading. In some experimental work, it has been discovered that a second step of disperging or high-consistency mechanical shearing can help improve flowability and absorbency properties of the nits. Thus, hardwood fibers or a slurry comprising hardwood fibers can be substantially curled or formed into nits in a first disperging or kneading operation, such as by treatment with a Maule disperger, a BIVIS disperger, a disk disperger, or other suitable equipment capable of curling and disperging high-consistency wood pulp. The mechanically treated fibers or nits can then be optionally dried, followed by adjustment of the moisture content to bring the consistency to about 20% or greater, such as from 20% to 30%. Thereafter the fibers are again subjected to mechanical kneading or disperging at a suitable energy level to create nits, which are then dried. For example, a Maule shaft disperger can be used to create nits in a first step with an exit consistency of about 30% or higher, whereafter the consistency is reduced to from about 20% to about 30% for further mechanical processing in a Hobart mixer for high-consistency mixing and kneading. Without wishing to be limited by theory, it is believed that a second disperging step under different processing conditions (different consistency or different mechanical equipment) can create new shear conditions that may help remove free fibers projecting from the surface of nits formed in the first step, fibers that may not have been sufficiently able to become entangled into the nit under the conditions of the first treatment.

In addition, it is believed that drying or partial drying after a first disperging step, followed by remoistening, a second disperging step, and final drying, can promote hydrogen bonding of previously loose fibers with the parent nits such that the fibers are no longer projecting from the nits to the degree before. In other words, it is believed that the particularly good nit properties achieved in two disperging steps with intermediate drying can be explained in terms of hydrogen bonding. By remoistening partially dried nits and drying the nits again, new hydrogen bonds can form between loose fibers and the other fibers in the nits from which the loose fibers project. If the nits are simply wetted and redried, new hydrogen bonds may form between projecting fibers and other nits, resulting in clumps. Disperging or mechanical shear is needed after rewetting to separate the nits and promote bonds between fibers in the same nit rather than bonds between nits. Following the second disperging step, entanglements between adjacent nits will have been largely disrupted by the mechanical action and tighter, denser nits will have been formed. Drying can then be completed, optionally with agitation to prevent additional clumping. But if the consistency of the nits is sufficiently high after the second disperging step, such as at least about 30% and specifically at least about 40%, relatively little agitation may be needed during drying because the nits will have little tendency to clump, especially if debonder is present.

Further, the use of two or more disperging steps offers the opportunity for unique combinations of temperature and chemistry better tailor the properties of the nits. For example, the first disperging step may be done at an elevated pH (e.g., pH above 8, such as from 9 to 11), wherein the fibers are swollen and relatively flexible. Then the second disperging step may be performed under lower pH, such as a pH of from about 4 to 6, wherein the swelling of the fibers are reduced and the ability of the fibers to collapse into nits may be enhanced. Benefits can also be obtained by the reverse procedure, in which a first kneading or disperging step is conducted at low pH, followed by a second step at elevated pH, with the potential to produce nits that are relatively more round or that have other useful morphological properties.

Another benefit of disperging nits in two or more stages is that a first chemical can be added in a first disperging step, followed by addition of a second chemical in a second disperging step. This can be particularly helpful when the two chemicals would give undesired reactions when added simultaneously, such as an anionic compound and a cationic compound. For example, an anionic anti-microbial compound and a cationic wet strength agent or cationic debonder could be added in separate disperging steps. Or two charged compounds can be added that would normally interfere with each other or cause precipitation.

Nit Properties and Incorporation Into Absorbent Articles

Two or more types of nit materials may be combined in a single absorbent product, generally by incorporation of the nits into the central absorbent section and particularly as a component of the upper absorbent member, though nits or other free flowing absorbent material can also be used in the central absorbent member if the material is sufficiently restrained or under sufficient tension that the shape directing role of the central absorbent member is not compromised. The nits or other free flowing absorbent particles may be blended or layered within an enclosed pouch or pocket or may be distributed in two or more enclosed pouches or pockets, especially pockets having a longitudinal orientation and a length substantially greater than their width. The pocket or pouch is generally formed by joining two particle restraining layers together such that a region between the two layers is open and able to receive particles. Particle restraining layers can include a topsheet, a backsheet, a layer of absorbent material such as an airlaid web or tissue layer, a polymeric film or nonwoven web in general, and the like, such that the nits are not able to escape from the article under normal conditions of use. The same applies to other loose particles or chips of material as well, including superabsorbent particles and fibers; mixtures of nits and absorbent polymers; encapsulated materials; starch globules; loose curled fibers and/or loose crosslinked fibers, such as those of U.S. Pat. No. 5,190,563, issued Mar. 2, 1993 to Herron et al., herein incorporated by reference; chips of densified BCTMP; other chips or particles of densified cellulosic materials, and particularly absorbent materials that remain free flowing when wet, such as the materials disclosed in WO 98/43684, "Absorbent Item," M. Raidel, Oct. 8, 1998; and the like. Raidel in particular discloses the use of free-flowing materials such as hollow spheres of polymethylurea with an absorbent capacity of greater than about 10 grams of fluid per gram of free-flowing absorbent. Another class of potentially useful free-flowing particles is microporous macrobeads, such as those disclosed by A. J. Disapio et al. in "Microporous Macrobeads Provide New Opportunities in Skin Care," Soap and Cosmetics, Vol. 75, No. 2, February 1999, pp. 42–47, which are palpable polymeric beads that may be spherical or formed by attrition of spheres comprising pores within the bead for retention or release of chemical agents or liquids. Microporous macrobeads are commonly made from acrylate copolymers with added monomers to control surface properties, void volume, etc. For example, ester-rich monomers lead to highly lipophilic surfaces. Particle size can be from about 100 to 500 microns, or from 50 to 100 microns, or about 50 microns or less. Microporous macrobeads may be used alone or in combination with nits, microspheres, beads, or PMU particles.

Various types of nits or other free-flowing particles can be incorporated in discrete pouches or layers in an absorbent article, or can be mixed together uniformly or in gradient form. Principles and equipment for mixing free-flowing particles are described by B. H. Kaye in "Mixing of Powders," Chapter 11 in *Handbook of Powder Science and Technology*, ed. by M. E. Fayed and L. Otten, $2^{nd}$ ed, Chapman & Hall, New York, 1887, pp. 568–585.

Nits and other free-flowing particles can be placed in a central depression in an outer absorbent member, restrained beneath by absorbent material or by an underlying backsheet, and then the nits can be restrained from above by a superposed topsheet that is adhesively attached to the surrounding portions of the outer absorbent member. Multiple layers of nits or other free flowing particles can be added. A porous web serving as a top restraint for a first layer of nits can serve as the lower restraint for a second layer, which in turn can be restrained from above by a topsheet or other porous web with pore size sufficiently small to restrain the nits or particles. In one embodiment, the nits are tightly packed into the pocket or pouch such that some positive tension is maintained on the encasing sections of the pocket or pouch even when the article in unrestrained, for particles that are too loose and free to shift can fail to conform well to the body in used.

In one embodiment, the absorbent core and optionally the central absorbent member has a pocket of substantially loose absorbent material comprising a first type of particles and a second type of particles to obtain a balance between various properties such as ability to flow freely when dry or when wet, absorbency, conformability, ability to resist bunching, etc. A third type of particles or even more types of particles can also be present. In one embodiment, the first type of particles is hardwood nits, comprising by way of example only 50% or more of the mass of the absorbent material in the pocket. The second type of particles can be other cellulosic nits, such as, for example, softwood nits having a substantially larger particle size than the first type of particles. The second type of particles, like the first type, can be treated with a small quantity (e.g., less than 5% by dry mass, and specifically less than 1% by dry mass) silicones or other hydrophobic materials which can residing primarily on the surface of the particles to help prevent sticking or clumping of particles when wet. Alternatively, the second type of particles can be a mixture of cellulose and minerals such as kaolin or bentonite (resulting in a high ash content relative to mineral free cellulosic fibers), or may be crosslinked fibers or crosslinked nits (in which case the water retention value of the crosslinked nits will generally be substantially lower than for nits that are not crosslinked), or may be fiber-superabsorbent composites such as fibers wrapped around hydrogel material. A useful crosslinking agent is ammonium zirconium carbonate, which can be applied to a fiber slurry before making nits at a dosage, for example, from about 0.3 to 3% by weight, and then subjecting the nits to elevated temperature to effect crosslinking. The lubricity provided by the ammonium zirconium carbonate can be beneficial for the use of nits in the absorbent article. Wet strength agents such as Kymene can also be beneficial in controlling wet properties of the nits and increasing their ability to maintain bulk or remain free flowing when wet. Thus, in one embodiment, the central absorbent member comprises loose nits of fibrous material comprising a first type of nits and a second type of nits, substantially distinguished in a material property selected from fiber type, mean particle size (determined by sieve analysis according to American Society for Testing and Materials (ASTM) test method D-1921), ash content, chemical additive content, Water Retention Value, and wetting angle of the surface of the nits. Superabsorbent particles and odor control materials can be present as the second type or third type of particles or as a portion of a mix or composite comprising the second or third type of particles. When superabsorbents or hydrogel-forming materials are incorporated with the nits, they can be present in an amount greater than 0 to less than 100 weight percent, specifically from about 5 to about 95 weight percent, more specifically from about 15 to about 85 weight percent, and more specifically still from about 20 to about 50 weight percent, based on the total weight of the superabsorbent or hydrogel-forming polymeric material and nits in the absorbent composition. In one embodiment, less than about 10% superabsorbent particles are present for nits treated with hydrophobic material, in order to help maintain a free flowing nature of the nits even when wetted.

In one embodiment, nits or other free-flowing materials such as hollow spheres are combined with deformable particles that can have a particle size of about 2 mm or less, more specifically about 0.7 mm or less, including pieces of a soft foam such as a polyurethane foam or foam rubber material. Rounded particles are produced in some embodiments. The soft, deformable particles combined with the nits help improve the tactile properties of the pouch of nits, allowing a softer feel and more comfort when worn against the body. In general, the nits or other free flowing particles for use in any of the absorbent members of the present invention can be combined with one or more deformable materials, particularly in particulate form, for improved comfort and avoidance of a grainy feel, especially when larger sized free-flowing particles are used.

The nits can be enclosed in an encasement which is a thin, flexible, liquid pervious fibrous layer such as a spunbond web that encircles the nits and restrains them such that they do not escape the article or shift to undesired portions of the article. The encasement forms a pocket or pouch for holding the nits. In one embodiment, the pocket or pouch holding the nits can be substantially centered about the longitudinal axis of the article and can be located in the crotch region thereof.

In one embodiment, the nits in an absorbent article are disposed toward the body side surface and have at least one absorbent web between the nits and the backsheet. The nits can be contained within a framework formed by a central void in an outer absorbent member which restrains the nits or the pocket or pouch containing the nits and which helps maintain the nits along the longitudinal axis of the article. The absorbent web below the nits also helps provide proper shaping and helps hold the nits against the body of the user, especially if the absorbent web is a central rising member (hereafter described). Alternatively, a nonabsorbent central rising member can be beneath the nits to help urge them toward the body of the wearer.

With a central rising member below the nits or free-flowing particles, multiple discrete pockets can be helpful in reducing the tendency of nits or free-flowing particles to shift to the sides when the central portion of the pad is elevated by the action of the central rising member. In one embodiment, the maximum transverse (lateral) width of particle-containing pockets is less than about 3 cm and specifically less than about 2 cm. Discrete pockets of nits can be formed by adhesively laminated two fibrous webs together with regions of adhesive material joining the webs, according to principles known for formation of pockets of superabsorbent material in U.S. Pat. No. 5,030,314, "Apparatus for Forming Discrete Particulate Areas in a Composite Article," issued to T. B. Lang, Jul. 9, 1991, herein incorporated by reference, or according to other methods known in the art.

In another embodiment, the absorbent core comprises a molded, three-dimensional high bulk wet laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997; U.S. Pat. No. 5,429,686, issued to Chiu et al. on Jul. 4, 1995; U.S. Pat. No. 5,399,412, issued to S. J. Sudall and S. A. Engel on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; all of which are herein incorporated in their entirety by reference. Such uncreped structures can offer a plurality of flow channels along the surface of the web. When stacked or layered with other planar materials such as a polymer film, void space can still exist adjacent the surface of the tissue web to permit rapid flow of fluid parallel to the plane of the tissue web. Further, the uncreped tissues show excellent wet resiliency and high bulk under load when wet. Without wishing to be limited by theory, it is believed that the three-dimensional surface structures of such textured webs can maintain their shape and bulk when wet because the hydrogen bonds defining the arrangement of the fibers are formed in the molded, three-dimensional state, so the structure does not relax to a flat state when wetted.

Absorbent Components of the Core

The absorbent article generally comprises an outer absorbent member or outer shaping member and further comprises a central absorbent member located on, within, or beneath the outer absorbent member or outer shaping member, wherein the central absorbent member comprises a pouch of free-flowing particles. In embodiments where the pouch of free-flowing particles is intended to serve a major absorbent component (e.g., absorbent capacity of about 10 g or greater) as opposed to an intake strip, the outer absorbent member or outer shaping member can have a central void or depression for receiving the central absorbent member comprising a pouch of free-flowing particles, wherein the walls of the central void or depression provide lateral restraint to the pouch to prevent undesired deformation toward the longitudinal sides of the article. The pouch can be disposed on the body-side surface of the outer absorbent member or outer shaping member or facing the body-side but disposed within a central void in the outer absorbent member or outer shaping member.

The outer shaping member is not necessarily absorbent but provides shaping to the article, and can be a closed cell foam, or any absorbent material as well. If the central absorbent member has suitable capacity and especially if a wicking barrier is in place to prevent leakage to the outer shaping member, the outer shaping member need not absorb fluid to serve a useful function in an article capable of good performance. However, the outer member can be absorbent while also providing shaping functionality. If the central absorbent member has adequate absorbent capacity and especially if a wicking barrier is in place, it is unlikely that the outer absorbent member will become significantly moistened in use, in which case a low-cost material with poor wet resiliency can be used, such as ordinary fluff pulp or airfelt, without loss of performance.

In general, the absorbent core may be manufactured from a wide variety of liquid absorbent materials commonly used in disposable sanitary napkins, diapers, and other absorbent articles. Examples of suitable absorbent materials include comminuted wood pulp which is generally referred to as airfelt or fluff pulp, creped cellulose wadding, absorbent foams, absorbent sponges, synthetic staple fibers, polymeric fibers, hydrogel-forming polymer gelling agents, or any equivalent materials or combinations of materials.

The absorbent materials of the absorbent core, including the outer absorbent member or other members, can comprise one or more plies of wetlaid or airlaid tissue; cellulosic airlaid webs of comminuted fibers (commonly termed "airfelt"); other dry laid webs; creped cellulose wadding, absorbent foams; absorbent sponges; synthetic staple fibers; polymeric fibers; hydrogel-forming polymer gelling agents, or any equivalent materials or combinations of materials. Other useful materials include cellulose-superabsorbent mixtures or composites; hydroentangled webs comprising cellulosic fibers; composites of synthetic fibers and papermaking fibers; rayon; lyocell or other solvent-spun hydrophilic fibers, such as those disclosed in U.S. Pat. No. 5,725,821, issued Mar. 10, 1998 to Gannon et al., herein incorporated by reference; cellulosic foams including regenerated cellulose foams; hydrophilic, flexible foams; fiber-foam composites; absorbent nonwoven webs; cotton; wool; keratin fibers; peat moss and other absorbent vegetable matter; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998, herein incorporated by reference; or absorbent foams produced from high internal phase emulsions (HIPE) or other means, such as the foams disclosed in U.S. Pat. No. 5,692,939, issued Dec. 2, 1997 to DesMarais, U.S. Pat. No. 5,851,648, issued to K. J. Stone et al., Dec. 22, 1998, or in U.S. Pat. No. 5,795,921, issued Aug. 18, 1998 to Dyer et al., all of which are herein incorporated by reference. The absorbent materials of the absorbent core can also comprise corrugated absorbent materials for enhanced longitudinal transport of fluid, such as the materials disclosed in U.S. Pat. No. 4,578,070, issued Mar. 25, 1986 to Holtman, herein incorporated by reference in its entirety. In one embodiment, at least one layer of the absorbent core comprises cellulosic fibers and PET (polyethylene terephthalate) staple fibers, such as from about 5% to about 20% staple fibers by weight, to provide increased wet resiliency and integrity of the absorbent core.

A commercially available air-laid web is AIRTEXT™ 395 air-laid web sold by James River Corporation located in Green Bay, Wis. AIRTEX 395 air-laid web is 100% virgin softwood held together by an acrylic binder. Concert Fabrication Ltee, of Ontario, Canada, also produces a variety of densified airlaid webs held together with thermoplastic binder material. Other useful densified airlaid webs include the layered materials comprising superabsorbent particles and cellulosic fibers disclosed in U.S. Pat. No. 5,866,242, issued Feb. 2, 1999 to Tan et al., herein incorporated by reference.

A particularly useful cellulose-polymer composite material is coform, a hydraulically entangled mixture of pulp fibers and polymer, such as the materials disclosed in U.S. Pat. No. 4,879,170, issued Nov. 7, 1989 to Radwanski et al.; U.S. Pat. No. 4,100,324 to Anderson et al. issued Jul. 11, 1978, and U.S. Pat. No. 5,350,624 to Georger et al. issued Sep. 27, 1994, or the materials made by the methods of Lau et al. in U.S. Pat. No. 5,711,970 issued Jan. 27, 1998, all of which are incorporated herein by reference in their entireties.

Any suitable form of cellulosic material can be incorporated in the absorbent materials of the absorbent core, including wood fibers, such as bleached kraft softwood or hardwood, high yield wood fibers, and chemithermomechanical pulp fibers; bagasse; milkweed; wheat straw; kenaf; hemp; or peat moss. High yield fibers can be used to make absorbent members, exemplified by the high-yield airfelt disclosed in U.S. Patent No. 4,247,362, issued to J. C. Williams, Jan. 27, 1981, herein incorporated by reference. The fibers can also be crosslinked, sulfonated, mercerized, heat treated, mixed with thermoplastic stabilizer fibers, or treated with wet strength agents. Caustic-treated fibers, such as those made according to U.S. Pat. No. 5,858,021, "Treatment Process for Cellulosic Fibers," issued to Tong Sun and Sheng Hu, Jan. 12, 1999, herein incorporated by reference, can be especially beneficial in providing good absorbency and bulk properties. Mixtures of various fibers can be used, including coform, which comprises thermoplastic fibers and wood fibers deposited together in an airlaying process.

The absorbent materials of the absorbent core can comprise chemically modified cellulose, including any known cellulose derivatives, such as 2,3-dialdehyde cellulose or other cellulosic polymers derived therefrom, including those of K. Rahn and T. Heinze in "New Cellulosic Polymers by Subsequent Modification of 2,3-Dialdehyde Cellulose," *Cellulose Chemistry and Technology*, 32: 173–183 (1998), including sodium bisulfite adducts of 2,3-dialdehyde cellulose or various carboxy cellulose compounds. The modified cellulose compounds may be in powder, fiber, or film form. Likewise, acetylated cellulose may be used, as well as cellulosic fibers or films prepared from solutions of polysaccharides, particularly cellulose, in an aqueous tertiary amine N-oxide solvent, especially N-methylmorpholine N-oxide (NMMO); lyocell fibers in particular may be used, including those of U.S. Pat. No. 5,837,184, "Process for the Production of Cellulose Fibres Having a Reduced Tendency to Fibrillation," issued to H. Firgo, Nov. 17, 1998, herein incorporated by reference.

The absorbent core can also comprise the crinkled, quilted, absorbent pad disclosed in U.S. Pat. No. 4,650,481, issued Mar. 17, 1987 to O'Connor et al., herein incorporated by reference. The quilted form can be obtained in the pouch filled with particles by stitching or bonding certain portions of the encasement together.

Absorbent materials with high wicking fluxes can also be used in the present invention, including the materials of U.S. Pat. No. 5,843,852, "Absorbent Structure for Liquid Distribution," issued to J. Dutkiewicz et al., Dec. 1, 1998, herein incorporated by reference. Multilobal fibers or fibers with complex extruded cross-sections for high wicking flux can also be incorporated in the present invention.

The article may also comprise hydrophobic material around the sides of the absorbent core to further reduce edge leakage. For example, hydrophobic fibers may be placed in discrete areas, such as around the periphery of the hydrophilic absorbent core, to provide barriers against leakage, as exemplified in U.S. Pat. No. 5,817,079, "Selective Placement of Absorbent Product Materials in Sanitary Napkins and the Like," issued to R. Bergquist et al., Oct. 6, 1998, herein incorporated by reference. A related approach which can be applied to the present invention is given by Csillag in U.S. Pat. No. 4,015,604, issued Apr. 5, 1977. An absorbent product is disclosed with side leakage control means comprising a narrow longitudinally extending zone along each side edge of the product but spaced away from each of the side edges. This zone is impregnated with a liquid hydrophobic material from the garment facing surface to the body facing surface of the product. The hydrophobic impregnate is applied to a hydrophilic pad as the pad passes through the manufacturing equipment. Likewise, Canadian Pat. No. 884,608 issued to Levesque, Nov. 2, 1971, relates to treating the edges of a sanitary napkin product with hydrophobic material in order to prevent side leakage. In accordance with Levesque, the absorbent layer in the zone of the edges of the absorbent material is rendered hydrophobic while being maintained in a gas and moisture vapor permeable condition. The hydrophobic zone may be coated with a liquid repellent composition or chemically modified to render the fibers hydrophobic. In these embodiments with added hydrophobic fibers or hydrophobic matter toward the longitudinal sides of the absorbent core, a wicking barrier such as a polymeric film can pass over at least a portion of the surface of the hydrophobic areas in the crotch region of the absorbent core.

In many embodiments, a central pouch of nits is attached to an underlying absorbent layer to form a central absorbent member, and the central absorbent member is placed on the surface of or within a central void in an outer absorbent member. A wicking barrier can also be present to separate at least a portion of the central absorbent member from the outer absorbent member such that fluid communication between the two members is reduced.

The Wicking Barrier

The wicking barrier comprises one or more segments of a barrier material that impedes wicking from a central absorbent member or from a pouch of nits to laterally adjacent absorbent material or to absorbent material beneath the central absorbent member or from a pouch of nits. The barrier material can be a polymeric film or plastic film; a nonwoven web; a layer of rubber, silicone, or other non-absorbent materials; or a less pervious paper sheet including, for example, glassine, wax paper, impregnated papers, paper-polymer composites, densified tissue, paper or tissue containing internal sizing to render it less hydrophilic, paper or tissue treated with hydrophobic matter such as wax, silicone, thermoplastic material, or polyolefins. Flexible hydrophobic foams may also be used, such as a closed-cell polyurethane foam or a silicone foam. A hydrophobic web such as a bonded carded web of a polyolefin (such as materials commonly used for surge layers in diapers, but without surfactants or other hydrophilic treatments) can also be used, provided that a useful barrier function is achieved.

Such materials can include the transfer delay barrier materials disclosed in the commonly owned U.S. patent application Ser. No. 60/079,657, "An Absorbent System for Personal Care Products Having Controlled Placement of Visco-Elastic Fluids" by A. S. Burnes et al., previously incorporated by reference.

The barrier material can also comprise hydrophobic matter that is used to impregnate a portion of the outer absorbent member or a portion of the central absorbent member to reduce lateral wicking. Such hydrophobic matter can include adhesives and particularly hot melt adhesives added to the absorbent article while molten; wax; pastes or emulsions comprising waxes; silicone-based fluids, gels, pastes, or caulk; phenolic resins or other resins which are cured after impregnating the fibrous material of the central absorbent member or outer absorbent member; polyolefins or other plastic or hydrophobic material added as powder, particularly sintered powder, or held in place by adhesives, or by thermal bonding. In addition to the impregnating material, which helps prevent lateral fluid flow in the article, there can be a distinct break, gap, or slit between the central absorbent member and the outer absorbent member in the crotch region to further impede fluid communication, especially by removing or severing fibrous pathways between the central absorbent member and the outer absorbent member.

The barrier material can be placed along a portion of the perimeter of a central absorbent member to reduce or prevent wicking to the surrounding outer absorbent member. In such an embodiment, the wicking barrier can comprise a thin layer of a hydrophobic material such as a polymeric film, a nonwoven web, a thermoplastic material, a layer of hot melt adhesive, or a flexible material such as a wax impregnated in the fibers adjacent the perimeter of the central absorbent member. When the wicking barrier is a polymeric film or nonwoven web, it can have radial dimensions when set in place slightly greater than the radial dimensions of the central absorbent member such that a strip of the material rests on the surface of the absorbent core to define a visible barrier along at least a portion of the perimeter of the central absorbent member.

Examples of absorbent core construction incorporating wicking barriers and related structures are disclosed in commonly owned copending applications Ser. No. 09/165,875, "Absorbent Article with Center Fill Performance," filed Oct. 2, 1998, Ser. No. 09/165,871, "Absorbent Article Having Good Body Fit Under Dynamic Conditions," also filed Oct. 2, 1998; and Serial No. Unknown, "Center-Fill Absorbent Article with a Wicking Barrier and Central Rising Member," filed Oct. 1, 1999 by Chen et al.; all of which are herein incorporated by reference.

Central Rising Member

The central rising member is a structure generally beneath the central absorbent member, or beneath the pouch filled with free-flowing particles in particular, and above the backsheet which causes the central absorbent member (or at least a portion thereof) in the crotch region of an absorbent article to deflect upward when the absorbent article is laterally compressed in the crotch region from the longitudinal sides of the article. The central rising member can be a flexible absorbent material such as densified airlaid pulp fibers, coform, or one or more layers of creped or uncreped tissue, adapted with bending lines, scoremarks, flexure points, and/or folded sections such as an "e"-folded web such that lateral compression from the longitudinal sides of the central rising member causes at least a portion of the central rising member to deflect upwards with sufficient force or resiliency that the overlying central absorbent member can be deflected or urged toward the body. An absorbent central rising member can also be configured as a flattened tube.

The central rising member can comprise a at least one ply of a resilient material having a wall thickness, an internal void within the resilient material, present due to folding or layering of the material, wherein the z-direction thickness of the internal void increases in size during lateral compression as the upper surface of the central rising member is displaced upward. Alternatively, the central rising member can lack an internal void, being a single layer of material that is folded or creased to form an inverted V-shape or U-shape when the longitudinal sides thereof are moved inward toward the initial longitudinal centerline of the central rising member.

The central rising member can comprise a thermoplastic deformation element as disclosed by K. B. Buell in U.S. Pat. No. 5,300,055, issued Apr. 5, 1994, herein incorporated by reference, but the central rising member can also be non-thermoplastic such as a densified cellulosic web. Thus, the central rising member can have a flexure means, and particularly a longitudinally extending flexure hinge, for inducing the body facing surface of the central rising member to have a convex upward configuration when the sanitary napkin is worn. In an alternative embodiment, the deformation element has a central region having a "W" shaped cross-section wherein the body facing surface of the central rising member having the convex upward configuration is located in the central region, generally symmetrically between the longitudinal side edges of the napkin. In another embodiment, the central rising member has a cup-shaped front region and a back region having a convex upward configured body-facing surface.

In one embodiment, the central rising member can be a flattened, rolled tissue or paper structure including "e"-folded materials, with a centerline aligned with the longitudinal axis of the article (the flat cross-bar of the "e"-shape lying in the transverse direction, normal to the longitudinal axis of the article). Upon lateral compression from the longitudinal sides of the article, the flattened "e"-shape deflects upwardly, the upper loop of the "e"-shape springing back into the approximate shape of a semicircle to urge the upper surface of the central absorbent member toward the body of the wearer.

The central rising member can also comprise the liquid pervious spacing structure for moving the topsheet away from the core, as disclosed by R. B. Visscher et al. in U.S. Pat. No. 5,324,278, issued Jun. 28, 1994, herein incorporated by reference.

Detailed examples of central rising members and their construction are disclosed in the commonly owned copending application, Serial No. Unknown, "Center-Fill Absorbent Article with a Wicking Barrier and Central Rising Member," filed Oct. 1, 1999 by Chen et al.; herein incorporated by reference in its entirety, which also provides further details on options for topsheets, backsheets, and other members of the absorbent core.

EXAMPLES

Example 1

Nit Preparation With a BIVIS Disperger

Bahia Sul eucalyptus pulp sheets were disintegrated using a Grubbens Pulper (Medium Consistency Pulper Model 01R, Cellwood Grubbens AB, Sweden) at approximately six percent consistency. Pulp was disintegrated about 30 minutes. Runs were performed with and without debonder. For runs with debonder addition, the debonder was added after five minutes of disintegration.

At the end of pulping, the pulp was diluted to about 4.5% consistency and pumped over to the dump chest of a Bivis device while the agitator was running. The Bivis disperger (commonly termed an extruder by the manufacturer) was Model BC-45, manufactured by Clextral Inc., Firminy, France. Pumping was achieved using a pulper dump pump. The Bivis dump tank transfer pump was set to be in the recirculating mode. An Andritz belt press (Continuous Belt Press, Model CPF 0.5 meter, P3, Andritz-Ruthner, Inc., Arlington, Tex.) was used to dewater the pulp and discharge it into a screw conveyor system. Once activated, the feed valve off the Bivis Dump Tank Transfer Pump was opened and the recirculation valve was closed. The belt press was configured to give a discharge mat 2.5 cm thick. Discharge consistency was approximately 32 percent. This mat was broken up by the break-up screw at the end of the belt press and then was transferred by the screw conveying system to the feed hopper of the Bivis extruder.

Pulp was further disintegrated by the double feed screw system in the bottom of the feed hopper. The disintegrated pulp was fed to the Bivis feed screw and directly into the Bivis extruder. The Bivis extruder is a double screw, co-rotating extruder with the internal screw profile given in Table 1. All screw elements were single flight.

TABLE 1

Zones in the Bivis Extruder.

| Bivis Zone | Element No. | Screw Type | Length (mm) | Pitch (mm) | Slot width (mm) |
| --- | --- | --- | --- | --- | --- |
| Feed | 1 | T1F | 100 | 50 | none |
| Feed | 2 | T1F | 100 | 50 | none |
| 1 | 3 | T1F | 100 | 33 | none |
| 1 | 4 | T1F | 50 | 25 | none |
| 1 | 5 | RH6 | 50 | −15 | 6 |
| 2 | 6 | T1F | 100 | 33 | none |
| 2 | 7 | T1F | 50 | 25 | none |
| 2 | 8 | RH6 | 50 | −15 | 6 |
| 3 | 9 | T1F | 100 | 33 | none |
| 3 | 10 | T1F | 50 | 25 | none |
| 3 | 11 | RH6 | 50 | −15 | 6 |
| Discharge | 12 | T1F | 100 | 33 | none |
| Discharge | 13 | T1F | 100 | 33 | none |

Two extraction zones were used for all runs. Extraction plates were installed in Zones 1 and 2. Water and pulp fines were extracted from these zones.

For all samples, an attempt was made to control specific energy to a low-to-intermediate level in one set of runs and to high specific energy for another set of runs. Temperature was recorded. Maximum temperature generally correlates directly to specific energy, but maximum temperature tended to migrate toward Zone 1 as time progressed.

Ranges of the above parameters are given in Table 2 below:

TABLE 2

High and Low Process Values for the BIVIS-produced Nits.

| | Low | High |
| --- | --- | --- |
| Specific Energy (kW-h/T) | 90.4 | 218.3 |
| Outlet Consistency (%) | 46.8 | 55.1 |
| Max Temperature (° C.) | 99 | 116 |

The debonder was a quanternary ammonium compound, MacKernium™ 516Q-60 (McIntyre Group, Ltd., Chicago, Ill.) added at a dose of 2.78 kg (6.15 pounds) per metric ton.

Nits prepared were then oven dried overnight at 43° C.

Example 2

Nit Preparation Using a Maule Disperger

About 800 kg of Bahia Sul bleached eucalyptus kraft pulp were disintegrated using a Sulzer Escher-Wyss High Consistency Pulper (Model ST-C-W, Voith-Sulzer PaperTech, formerly Sulzer Escher-Wyss Gmbh, Ravensburg, West Germany). Pulp was disintegrated for 30 minutes at 12% to 15% consistency. At the end of 30 minutes, pulp was diluted to approximately 4% consistency and pumped to a first chest. Slurry was then ed at approximately 4% consistency from the first chest to a Black-Clawson Double Nip Thickener® (Model 200, Black Clawson, Middletown, Ohio) where it was dewatered to approximately 12% consistency and fed via screw conveyor to the headbox of the Andritz Belt Press (Andritz-Ruthner, Inc., Arlington, Tex.).

Pulp was discharged from the Belt Press at approximately 35% consistency to a break-up screw and thence to the Maule kneader/disperger by a heating screw, to raise the kneader inlet temperature to 80° C. Kneader outlet temperature was approximately 100° C. Target specific energy for the kneader was 98 kW-hr/ton (5.5 horsepower-days per ton).

One run was performed using the preceding procedure with the following exception: The outlet door to the kneader was closed and the kneader was operated with a rotor speed of 48 rpm for 10 minutes. This resulted in a higher energy input to pulp, causing the nits to be smaller with fewer fibers projecting from the surface of the nits, resulting in an improvement in the flowability of the nits.

Example 3

Bleached kraft eucalyptus pulp from Cenibra, Inc. was dispersed in a Maule disperger at an entry temperature of about 25° C. (room temperature) and an inlet consistency of 20% to form nits. Berocell 584 debonder was added a level of 3 kg/ton prior to dispersing. Nits were spread onto flat surfaces to a depth of about 2 cm and air dried overnight. The nits proved to be free flowing and were substantially free of free fibers rising from the surfaces of the nits that could cause entanglement between nits. The nits were screened to a size range between about 300 and 850 microns and then encased in spunbond nonwoven webs and sealed with heat sealing to produce particulate pouches suitable for incorporation into absorbent articles.

Example 4

Bleached kraft eucalyptus pulp from Aracruz, Inc. (Brazil) was dispersed in a Maule disperger (Maule Type GR 11 manufactured by Ing. S. Maule & C. S.p.A., Torino, Italy) at an entry temperature of about 25° C. (room temperature) and an inlet consistency of 20% to form nits. Nits were prepared with and without MacKernium 516Q-60 debonder. When added, the debonder was present at a dose of 2.78 kg (6.15 pounds) MacKernium 516Q-60 debonder per metric ton of pulp. The nits were made on the Maule machine and oven dried over night at 43° C. The nits were sieved to different size particles as listed below in Table 3. Nits in the size range from 300 to 600 micrometers were used in subsequent production of absorbent articles for other Examples. The percentage of yield at the different particle sizes show a significant difference between debonded versus non-debonded eucalyptus nits. Although a one useful particle size distribution range is from 300 microns to 850 microns, for some embodiments a useful range can be from 300 microns to 600 microns for good containment of the nits and product comfort. Larger nits, in some cases, can more likely be perceived as grainy or uncomfortable.

Surprisingly, the percent yield for the particle size range 300 microns to 600 microns was much higher when debonder had been added to the pulp than without debonder.

TABLE 3

Particle Size Distribution and Percentage of Yield for Eucalyptus Nits

| Screen Number | Particle Size, microns | Debonder Added % per Screen (n = 4) | No Debonder % per Screen (n = 4) |
| --- | --- | --- | --- |
| 20 | >850 | 41.35 | 62.5 |
| 30 | 600–850 | 24.71 | 19.5 |
| 50 | 300–600 | 34.52 | 12.2 |
| Pan | <300 | 3.39 | 0.82 |

Table 4 shows the difference between debonded versus non-debonded eucalyptus nits in terms of Centrifuge Retention Capacity values (n=2), as measured according to the Method for Determining Centrifuge Retention Capacity given above. The addition of debonder improves the Centrifuge Retention Capacity value—a surprising result given that the debonder has a hydrophobic nature. The debonder was MacKernium 516Q-60 at 2.78 kg (6.15 pounds) per metric ton of pulp. The eucalyptus nits were made on the Maule machine and oven dried over night at 43° C. The control codes were non-debonded Weyerhaeuser NB416 pulp and debonded Weyerhaeuser NF405 pulp. Pulp-based materials with debonder normally reduce the centrifuge retention capacity value as shown.

TABLE 4

Centrifuge Retention Capacity Values for Maule-produced Eucalyptus Nits

| Screen Number | Particle Size | Debonded CRC (g/g) | Non-Debonded CRC (g/g) |
| --- | --- | --- | --- |
| As Is | 300–850 | 2.3 | 1.4 |
| 20 | 850 | 2.6 | 1.6 |
| 30 | 600 | 2.0 | 1.6 |
| 50 | 300 | 2.3 | 1.5 |
| NB416 | NA | — | 5.7 |
| NF405 | NA | 3.9 | — |

The fluid intake and flow back values of eucalyptus nits is another property which can be considered. A fast intake and low flow back value can be useful in some embodiments. Table 5 shows the fluid intake and flow-back on the raw material (the Maule-produced eucalyptus nits), performed according to the Raw Material Absorbency Rate and Rewet Test Method given above. In this test, the third insult is 1 ml, while the first two use 2 ml of fluid. Surprisingly, the time required for taking in the second insult is generally roughly the same as the time required for the first insult, and the time required for the third insult when doubled to normalize it to 2 ml is still only slightly greater than required for the first or second insults. In other words, in the Raw Material Absorbency Rate and Rewet Test, the nits of the present example show an ability to take fluid in at a high rate even after multiple insults.

In Table 5, on average, the non-debonded nits had higher flow-back values than those with the MacKernium 516Q-60 debonder.

Table 6 shows the fluid intake and flow-back for eucalyptus nits enclosed in a pouch or "pillow case," prepared and measured according to the Intake and Rewet Test given above. The non-debonded nits also had higher flow-back values than those with the MacKernium 516Q-60 debonder. Fluff based products normally have fast intake and high flow back values. The intake times for the three insults when tested with the encased material showed increasing times required for multiple insults.

TABLE 5

Maule-produced Nits Intake Times And Flow Back Values for the Raw Material

| | Screen Number | Insult 1 (sec) | Insult 2 (sec) | Insult 3 (sec) | Flow Back 3 (g) |
| --- | --- | --- | --- | --- | --- |
| Debonded | As Is | 29.6 | 29.6 | 17.3 | 0.57 |
| Non-Debonded | As Is | 26.5 | 29.3 | 15.1 | 0.67 |
| Debonded | 20 | 28.0 | 28.6 | 14.9 | 0.67 |
| Non-Debonded | 20 | 30.3 | 30.7 | 18.8 | 0.77 |
| Debonded | 30 | 28.1 | 30.5 | 17.7 | 0.85 |
| Non-Debonded | 30 | 28.0 | 29.4 | 15.9 | 0.59 |
| Debonded | 50 | 28.8 | 30.1 | 16.9 | 0.55 |
| Non-Debonded | 50 | 28.5 | 31.4 | 18.1 | 0.77 |
| Debonded | 30–50 | 29.0 | 33.2 | 19.6 | 0.92 |
| Non-Debonded | 30–50 | 29.2 | 30.6 | 16.5 | 0.62 |

TABLE 6

Maule-produced Nits Intake Times and Flow Back for Encased Material

|  | Screen Number | Insult 1 (sec) | Flow Back 1 (g) | Insult 2 (sec) | Flow Back 2 (g) | Insult 3 (sec) | Flow Back 3 (g) |
|---|---|---|---|---|---|---|---|
| Debonded | As Is | 10.8 | 0.15 | 23.5 | 0.24 | 53.6 | 0.42 |
| Non-Debonded | As Is | 10.7 | 0.40 | 12.9 | 0.50 | 21.2 | 0.58 |
| Debonded | 20 | 10.7 | 0.05 | 22.5 | 0.13 | 40.0 | 0.33 |
| Non-Debonded | 20 | 8.7 | 0.26 | 11.4 | 0.38 | 16.1 | 0.52 |
| Debonded | 30 | 13.0 | 0.15 | 31.6 | 0.24 | 60.7 | 0.28 |
| Non-Debonded | 30 | 9.3 | 0.49 | 13.7 | 0.53 | 21.0 | 0.50 |
| Debonded | 50 | 10.0 | 0.13 | 33.7 | 0.17 | 57.0 | 0.27 |
| Non-Debonded | 50 | 11.4 | 0.54 | 21.3 | 0.67 | 35.6 | 0.63 |
| Debonded | 30–50 | 10.4 | 0.14 | 25.3 | 0.12 | 46.8 | 0.20 |
| Non-Debonded | 30–50 | 9.9 | 0.45 | 14.0 | 0.55 | 20.7 | 0.54 |
| NB416 | — | 18.1 | 0.18 | 97.9 | 0.11 | 230.5 | 1.3 |
| CF405 | — | 32.0 | 0.43 | 189.6 | 0.36 | >300 | NA |

Permeability testing was performed to determine the acceptable range of permeability for debonded Eucalyptus nits compared to three control materials. The control materials were non-debonded eucalyptus nits, CF-405 pulp from Weyerhaeuser Corporation (a debonded pulp), and NB416 pulp from Weyerhaeuser Corporation. The test method used to determine permeability was the Gel Bed Permeability test given above and the flow back test method was Intake and Rewet Test Method given above (for nits encased in a pouch). The data are summarized in Table 7 below.

TABLE 7

Permeability Data for Eucalyptus Nits.

|  | Screen size | Flow Back Values (g) | Permeability ($10^{-9}$ cm$^2$) |
|---|---|---|---|
| Debonded Eucalyptus Nits | 30–50 | 0.14 | 528 |
| Non-Debonded Eucalyptus Nits | 30–50 | 0.45 | 1372 |
| CF-405 | 400 gsm, densified to .076 g/cc | 0.43 | 618 |
| NB-416 | 400 gsm, densified to .076 g/cc | 0.18 | 549 |

A high permeability permits rapid fluid intake. A high permeability value for eucalyptus nits correlates to a high rewet value which creates a wet surface against the body. Lower permeability allows for fast fluid intake but less available void volume, which allows the fluid to be absorbed and retained by the material. The lower the permeability value, the less viscoelastic fluids are able to pass directly through the absorbent bed. In some embodiments, the viscoelastic fluids are selectively retained with the nits, yielding higher capacity and lower rewet values. A used permeability range is believed to exist below about $7 \times 10^{-7}$ cm$^2$, such as a range between about $3 \times 10^{-7}$ cm$^2$ and about $7^{-7} \times 10$, or, more specifically, between about $4.5 \times 7.0^{-7}$ cm$^2$ and about $7^{-7} \times 10$. Permeability results showed that debonded eucalyptus nits were in the same range for treated and non-treated fluff but were outside the non-debonded eucalyptus nits permeability values.

The nits sieved within the size range of 300 micrometers to 600 micrometers were then tested for cohesive strength, according to ASTM test method D-6128. The Flowability Coefficient (FFC) was obtained, which is the ratio of consolidation pressure ($\sigma_1$) to cohesive strength ($f_c$) measured according to the Jenike shear flow test for particles, as specified in ASTM Test Method D6128-97, "Standard Shear Testing Method for Bulk Solids Using the Jenike Shear Cell." The testing was performed for Maule-produced nits both with and without debonder, with testing performed by Jenike & Johanson, Inc. (Westford, Mass.). Results for low, medium, and high consolidation are shown in Table 8. The consolidation pressure, $\sigma_1$, and the cohesive strength, "Str.", are both reported in both pounds per square foot (psf), as reported by the testing firm, and in kPa. In addition to FFC (Flowability Coefficient), which is dimensionless, results are also shown for effective angle of internal friction ($\delta$) and kinematic angle of internal friction ($\phi$). The Flowability Coefficient values greater than 2 and also greater than 3 are indicative of a material with a degree of free flowing behavior. Nits with substantially higher flowability have been prepared, such as those of Example 8 below, and are expected to have even higher Flowability Coefficients. For example, highly flowable particles for use in the present invention can also have a Flowability Coefficient of 3.5 or greater or of about 4 or greater. The effective angle of internal friction can also be related to flowability or tendency to bridge in hopper flow. The effective angle of internal friction can be from about 40° to about 67°, or from about 40° to about 60°. The testing in this case did not show strong differences in the measured parameters for the nits with and without debonder.

TABLE 8

Jenike Shear Cell Data for Sieved Maule-produced Nits.

| Consolidation | Sample | $\sigma_1$, psf | $\sigma_1$, kPa | Str., psf | Str., kPa | FFC | $\delta$ | $\phi$ |
|---|---|---|---|---|---|---|---|---|
| Low | Debonder | 90 | 4.31 | 38 | 1.82 | 2.4 | 65° | 57° |
| Low | No deb. | 87 | 4.16 | 39 | 1.87 | 2.2 | 67° | 60° |
| Medium | Debonder | 362 | 17.32 | 116 | 5.55 | 3.1 | 62° | 56° |
| Medium | No deb. | 386 | 18.47 | 135 | 6.46 | 2.9 | 62° | 56° |
| High | Debonder | 727 | 34.79 | 243 | 11.63 | 3 | 59° | 52° |
| High | No deb. | 720 | 34.46 | 199 | 9.52 | 3.6 | 60° | 54° |

Compressibility testing also performed by Jenike & Johanson yielded density values of up to 232 kg/cubic meter (14.5 pounds per cubic foot) for both sets of nits tested, with a range of from 104 kg/cubic meter 6.5 to 232 kg/cubic meter, with the variation due to possible voids inside the bed of nits when the nits were poured into a contained.

Example 5

Eucalyptus nits were also produced on the BIVIS equipment described above. Table 9 lists the centrifuge retention capacity values for eucalyptus nits with MacKernium 516Q-60 debonder at three different levels. The eucalyptus nits were oven dried over night at 43° C. An increase in debonder did not appear to reduce the absorbent capacity of the nits.

The control codes were non-debonded Weyerhaeuser NB416 pulp and debonded Weyerhaeuser NF405 pulp. Pulp-based materials with debonder normally reduce the centrifuge retention capacity value as shown.

TABLE 9

BIVIS-produced Centrifuge Retention Capacity Values

| Sample | Particle Size | Debonder Level (kg/metric ton of pulp) | CRC (g/g) |
|---|---|---|---|
| Eucalyptus nits | 300–850 | 0.68 | 1.6 |
| Eucalyptus nits | 300–850 | 2.78 | 1.2 |
| Eucalyptus nits | 300–850 | 4.54 | 1.6 |
| NB416 | NA | NA | 5.7 |
| NF405 | NA | NA | 3.9 |

The fluid intake and flow back values were measured and are shown in Table 10, measured according to the Raw Material Absorbency Rate and Rewet Test Method. These results show how the specific type of debonder does not inhibit fluid intake or increase the flow-back values independent of the amount of debonder.

TABLE 10

BIVIS-produced Raw Material Intake Times and Flow Back Values

| Sample | Debonder Level (lbs./metric ton of pulp) | Energy Level (Amp) | Insult 1 (sec) | Insult 2 (sec) | Insult 3 (sec) | Flow Back 3 (g) |
|---|---|---|---|---|---|---|
| As Is | 1.5 | 58 | 28.1 | 30.0 | 20.9 | 0.90 |
| As Is | 1.5 | 94 | 27.6 | 31.7 | 21.4 | 0.93 |
| As Is | 6.17 | 67 | 28.8 | 29.6 | 15.9 | 0.81 |
| As Is | 6.17 | 102 | 28.2 | 30.9 | 17.0 | 0.84 |
| As Is | 10.0 | 62 | 28.1 | 31.6 | 18.9 | 0.94 |
| As Is | 10.0 | 100 | 30.6 | 33.4 | 19.6 | 0.96 |

Example 6

A small scale non-menstrual use test was run on the Maule produced non-debonded and debonded eucalyptus nits of Example 4. The nits were sieved to four different particle sizes. 3.0 grams of dry nits were placed in a nonwoven pouch and heat sealed on all edges. The pouch was 95 mm long and 40 mm wide. The pouch was oval in shape and constructed of 40 gsm (1.2 osy) pink prism on the top and 20 gsm white SMS (spunbond-meltblown-spunbond laminate) on the bottom. On the bottom of the pouch, 0.5 grams of superabsorbent material was attached with adhesive. The oval pouch was placed on top of and in the center of a pre-cut, pre-adhesive sprayed hour glass shaped 90-gsm coform layer. The coform layer was 210 mm long and 65 m wide and constructed of 60 percent polypropylene and 40 percent pulp. The coform was adhesively attached to a 20-micron thick polyethylene web serving as a backsheet. A 20-gsm spunbond cover was placed on top of the pouch and coform layer. The cover stock was attached to the coform and the backsheet with adhesive, and the article was die cut to the same width and length of the coform to form a sanitary napkin. A two millimeter edge seal was embossed within the coform and was two millimeters from the edge of the coform. Nine subjects wore each code for one hour dry and one hour wet with 5 milliliters of Astroglide® injected into the middle of the pouch. Astroglide® was injected into the center of the pouch using a syringe and needle and uniformly distributed in the pouch. Astroglide® is a personal lubricant manufactured by BioFilm, Inc.(Vista, Calif.). The subjects completed a questionnaire to rate the following attributes: pad comfort, pad softness, and bulkiness. It is a combination of these attributes which determine if a product is acceptable to wear by the woman. The scale is from 1 to 7 with 7 being the best rating for comfort, softness and least bulkiness of the product. The average subject attribute results are summarized in Tables 11 and 12. One useful eucalyptus nits particle size range is from 20 to 50 mesh and more specifically greater than 30 mesh but less than 50 mesh.

TABLE 11

Average Subject Attribute Ratings for Debonded Nits

| Attribute | 20 Screen | 30 Screen | 30–50 Screen | 50 Screen |
|---|---|---|---|---|
| Pad Comfort | 6.5 | 6.0 | 6.3 | 6.5 |
| Pad Softness | 6.5 | 6.7 | 6.6 | 6.6 |
| Bulkiness | 6.4 | 6.6 | 6.6 | 6.6 |

TABLE 12

| Attribute | Average Subject Attribute Ratings for Non-Debonded Nits | | | |
|---|---|---|---|---|
| | 20 Screen | 30 Screen | 30–50 Screen | 50 Screen |
| Pad Comfort | 6.5 | 6.5 | 6.6 | 6.7 |
| Pad Softness | 6.7 | 6.7 | 6.9 | 6.7 |
| Bulkiness | 6.2 | 6.6 | 6.6 | 6.6 |

Example 7

A 175-gsm airlaid densified web with a density of about 0.1 g/cc was cut to a dumbbell shape with a length of about 21.5 cm and a width at the transverse centerline of about 6 cm. A central region of the outer absorbent member was removed by a die cutting operation to provide a central void in the outer absorbent member 42.7 cm long and 3.7 cm wide. The dumbbell-shaped outer absorbent member was placed on a 20-gsm polyethylene backsheet provided with contact adhesive. The backsheet was substantially larger than the dumbbell-shaped absorbent web. A rose-colored 20-gsm polyethylene film was die cut to be a rounded rectangle 20.3 cm long by 4.7 cm in width and was centrally placed over the central void to serve as a wicking barrier. 3.3 grams of loose nits were then placed directly in the void over the wicking barrier.

The nits were made of bleached kraft eucalyptus fibers which had been mechanically curled and disperged to form small dense flocs about 1 mm in diameter. The nits were prepared by taking 20 grams of dry eucalyptus pulp that had been previously disperged in the moist state (about 30% consistency) in a Maule disperger, then further moistening the pulp to a consistency of about 20% and beating the fibers in a 4.7-liter (5-quart) Hobart mixer for 1.5 hours to create dense nits. The moist nits were then spread out on a surface and air dried. FIG. 15 is a micrograph from a scanning electron microscope (SEM) showing a characteristic nit from this batch. The nit is substantially ovoid in shape and is substantially free of loose fibers projecting from the surface of the nit that could entangle with other nits. In some degree of contrast, FIG. 16 shows a form of a nit having projecting fibers rising from the surface of the nit.

The dry, loose nits were placed over the wicking barrier film inside the void of the outer absorbent member and covered with the a 20-gsm spunbond polypropylene topsheet, which served to hold the nits in place and function as the upper half of an encasement, while the wicking barrier served as the lower half of the encasement. The topsheet was provided with contact adhesive on the side toward the absorbent core, permitting it to join to the horizontal component of the wicking barrier and form a seal to hold the nits in place. The topsheet had also been treated with 0.3% by weight of a surfactant comprising 45 wt. % polyethoxlated hydrogenated ethoxylated castor oil and 55 wt. % sorbitan monooleate, available from ICI Americas (Wilmington, Del.).

After the topsheet was attached, the entire article was die cut with a dumbbell-shaped die having dimensions greater than the outer absorbent member (24.4 cm long, 8 cm wide at the transverse centerline) to provide a rim of backsheet material and cover material around the outer absorbent member in an absorbent article having good integrity provided in part by the contact adhesive on the polymeric film.

A loop of the colored barrier material was visible through the translucent topsheet (the horizontal component of the pink wicking barrier).

The central absorbent member comprising nits was conformable, flexible, and had a comfortable, soft feel.

Example 8

Sanitary napkins were assembled generally according to Example 7, except that the nits were first encased in an encasement comprising a 20-gsm spunbond polypropylene web. Experimental use tests with menstruating subjects were conducted using nits that were treated with debonder as well as nits not treated with debonder. Based on visual appearance and leakage of the used products, the absorbent articles comprising nits treated with debonder provided better intake and fluid handling performance.

While not wishing to be bound by any particular theory, it is believed that the improvement in absorption of menses is due to the addition of debonder to the eucalyptus nits process which creates a positively charged surface on the eucalyptus fibers. Red blood cells are negatively charged, and the positively charged surface on the eucalyptus nits is believed to attract and retain the negatively charged components in blood. A typical cationic debonder would be a quaternary ammonium salt of a fatty acid. As is well known to those who process wood pulp fibers, an aqueous solution of a debonder will spontaneously cover a cellulose surface. In the case of a cationic debonder, the cellulose surface will then become positively charged and will more effectively adsorb negatively charged red blood cells and blood proteins. The absorption of proteins and cells is believed to reduce the viscosity and viscoelasticity of the remaining fluid, thus improving intake and distribution of the fluid throughout the absorbent core by wicking forces.

In a layered or gradient product design, the positively charged eucalyptus nits can be placed on top of a superabsorbent material that is adhered to or held against the bottom of the absorbent structure. This layering provides an upper layer of hydrophilic, charged material which increases the removal of red blood cells and other negatively charged components of blood by the eucalyptus nits. The superabsorbent on the bottom is then more efficient at pulling in the residual water due to this filtering of the red blood cells by the eucalyptus nits. This reduction of hematocrit before the superabsorbent layer reduces gel blocking and increases the superabsorbent's swelling capability.

Example 9

Nits exposed to two distinct disperging operations were prepared by taking two 100 g portions of the dry, debonder-free Maule-produced eucalyptus nits of Example 4, and remoistening each portion with tap water to a consistency of 20%. One portion was then sprayed during stirring with 3 g of "5% Silicone Mold Release," product 3045 of Crown Industrial Products, Hebron, Ill. (a copyright date of 1969 appears on the spray can), a product comprising chlorinated solvents with 5% silicone. The spray application gave an estimated silicone add-on of 0.15%. The two portions of nits were then separately disperged for 1.5 hours. The silicone-treated nits were disperged in a KitchenAid Classic mixer, model K45SS (St. Joseph, Mich.), at the lowest speed, "stir." The moistened nits without silicone were disperged in a 4.7-liter (5-quart) Hobart mixer, Model N-50 of Hobart Canada (North York, Ontario, Canada). Disperging in both cases was performed for 1.5 hours. (Both the KitchenAid and Hobart mixers appear to be essentially the same devices with similar rotating speeds and rotors.) The nits from both fractions were then dried for about 2.5 hours at 105° C.

Following treatment, both fractions had improved flowability relative to the nits of Example 4. The silicone treated nits, however, had several different properties. The particle size distribution was finer that that of the fraction without silicone, which had formed a large number of multiparticle clumps. Sieving gave the results in Table 13. The presence of silicone during the second dispersing step appears to have promoted a new particle size distribution, with the silicone-treated fraction having about half the mass of large nits (particles over 850 microns) compared to the fraction without silicone.

TABLE 13

Sieve Analysis for Twice Disperged Nits

| Screen Number | Particle Size, microns | With Silicone | Without Silicone |
|---|---|---|---|
| 20 | >850 | 35.10 | 67.73 |
| 30 | 600–850 | 33.70 | 18.39 |
| 50 | 300–600 | 30.91 | 13.55 |
| Pan | <300 | 0.29 | 0.33 |

In spite of the clumps and larger particles in the fraction without silicone, it had better flowability (evidenced by simple handling and pouring of the material within a plastic bag) than the original Maule-produced nits. But the silicone-treated fraction had very few clumps and very little tendency to coalesce, but flowed readily, similar to sand when held in the hands. The angle of repose for the silicone treated fraction was measured at 57°. The fraction without the silicone displayed a slightly lower angle of repose, 51°, but the nits bridged the funnel twice during measurement and required pushing to urge them out of the funnel. Given the low mass of the particles, these angles of repose below 60° are believed to be good evidence of flowability or of a lack of strong cohesive forces between the particles. Without limitation, it is believed that the second dispersing step improved flowability by adding more energy to the nits to create dense, compacted structure, by providing new shear conditions that could bring loose fibers into back into contact with the nits, and by allowing hydrogen bonds to form between loose fibers and their parent nits. Further, without wishing to be bound by theory, it is believed that the addition of silicone helped prevent clumping and may have allowed for better break-up of nits during disperging to yield smaller particle sizes, while also enhancing lubricity between dry nits. Other lubricants and debonders are expected to have a similar effect in promoting good particle size distribution during disperging, whether in a first or second dispersing step.

Examples 10–16

By way of illustration, a variety of feminine care products can be prepared from the nits produced in any of the above Examples. In Example 10, a pre-cut oval pouch made from polyolefin spunbond webs can be filled with nits and optionally with odor-control compounds such as zeolites and sealed around the edges ultrasonically or thermally. The pouch can be attached to an underlying absorbent layer such as coform, airlaid or a fluff batt. A spunbond cover is placed over the pouch and attached with adhesive to form a sanitary napkin.

In Example 11, a pre-cut oval pouch can be filled with a layer of superabsorbent on the bottom, with adhesive on the lower inner surface of the pouch helping to hold the superabsorbent particles, with nits are placed on top of the superabsorbent. The pouch is attached to an absorbent layer such as coform, airlaid or a fluff batt. A spunbond cover is placed over the pouch and attached with adhesive. A section of an activated carbon fabric may also be attached to the coform for odor control.

In Example 12, a liquid-pervious pouch is filled with superabsorbent and nits which are mixed together and the pouch is sealed around all edges. The pouch is attached to an absorbent layer such as coform, airlaid or a fluff batt. A spunbond cover is placed over the pouch and attached with adhesive.

In Example 13, a layer of nits is sandwiched between a layer of low basis weight coform or airlaid (less than 120 gsm) and a spunbond cover and is sealed with heat around the edges.

In Example 14, a pantiliner is formed from a layer of nits comprising eucalyptus fibers that is sandwiched between a layer of low basis weight coform or airlaid (less than 120 gsm) and a backsheet. A spunbond cover is placed over the absorbent and the pantiliner is sealed with heat around the edges.

In Example 15, a tampon is filled with nits with or without superabsorbent and a nonwoven cover stock is wrapped around the nits for containment.

In Example 16, a tampon is filled in the center with nits with or without superabsorbent and a layer of airlaid or fluff batt is wrapped around the nits and a cover stock material is attached to the airlaid or fluff batt.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article comprising a pouch filled at least in part with free-flowing cellulosic nits, the nits comprising papermaking fibers and a nit conditioner effective to improve free flow of the nits as compared to the nits without the nit conditioner, wherein the free-flowing cellulosic nits have a Flowability Coefficient of about 2 or greater.

2. The absorbent article of claim 1, wherein the nit conditioner comprises a chemical additive selected from a debonder, a dispersant, a lubricant, and a surfactant.

3. The absorbent article of claim 2, wherein the chemical additive is a debonder.

4. The absorbent article of claim 3, wherein the debonder comprises a cationic polymer.

5. The absorbent article of claim 2, wherein the chemical additive is hydrophilic.

6. The absorbent article of claim 2, wherein the chemical additive is hydrophobic.

7. The absorbent article of claim 1, wherein the nit conditioner comprises a silicone compound.

8. The absorbent article of claim 7, wherein the silicone compound is amphoteric.

9. The absorbent article of claim 1, wherein the nit conditioner comprises an oil or a wax.

10. The absorbent article of claim 1, wherein the nit conditioner has a mass of about 0.1% or greater of the dry mass of the nits.

11. The absorbent article of claim 1, wherein the nit conditioner comprises a surfactant selected from anionic and nonionic surfactants.

12. The absorbent article of claim 1, wherein the nits have an angle of repose of about 70° or less.

13. The absorbent article of claim 1, wherein the nits comprise about 50% or greater by weight of eucalyptus fibers.

14. The absorbent article of claim 1, wherein at least 90% by weight of the nits have a particle size range from 100 microns to 800 microns as determined by sieve analysis.

15. The absorbent article of claim 1, wherein the nits are substantially free of particles greater than 850 microns.

16. The absorbent article of claim 1, further comprising superabsorbent particles within the pouch.

17. The absorbent article of claim 1, wherein the pouch has a width of less than about 3 cm.

18. An absorbent article for use on the body of a wearer, the absorbent article having a longitudinal axis, a transverse axis, two longitudinal sides, a target zone and a body side, comprising:
    a) a liquid impervious backsheet;
    b) a liquid pervious topsheet attached to the backsheet;
    c) a conformable intake member comprising a pouch containing free-flowing particles;
    d) an outer shaping member laterally surrounding the pouch; and
    e) a wicking barrier between at least a portion of the pouch and the outer shaping member,
        wherein the free-flowing particles have a Water Retention Value of about 1.5 g/g or greater and a Flowability Coefficient of about 2 or greater.

19. The absorbent article of claim 18, wherein the pouch has a width of less than about 5 cm and a length of about 10 cm or greater.

20. The absorbent article of claim 18, wherein the free-flowing particles comprise hardwood nits.

21. The absorbent article of claim 18, wherein the free-flowing particles comprise one of polymeric beads, hollow spheres, and mineral particles.

22. The absorbent article of claim 18, wherein the free-flowing particles comprise at least about 30% nits by weight and no more than about 30% mineral matter by weight.

23. The absorbent article of claim 18, wherein the free-flowing particles are substantially free of clay.

24. The absorbent article of claim 18, wherein at least 25% by mass of the free-flowing particles have a particle size above 300 microns.

25. The absorbent article of claim 18, wherein the free-flowing particles have a mean particle size between about 300 microns and about 600 microns.

26. The absorbent article of claim 18, wherein the pouch further comprises an odor control agent.

27. The absorbent article of claim 18, wherein the free-flowing particles further comprise one of an odor-control agent, an anti-microbial agent, and a surfactant.

28. The absorbent article of claim 18, wherein the free-flowing particles further comprise an enzyme.

29. The absorbent article of claim 18, further comprising superabsorbent particles within the pouch.

30. The absorbent article of claim 18, wherein the free-flowing particles comprise cellulosic fibers and one of a debonder, a lubricant, a silicone compound, and a surfactant.

31. The absorbent article of claim 18, wherein the free-flowing particles comprise cellulosic fibers treated with a quaternary amine debonder agent.

32. The absorbent article of claim 18, wherein the free-flowing particles comprise cellulosic nits with added hydrophobic matter on at least a portion of the surface of the nits.

33. The absorbent article of claim 18, wherein the free-flowing particles comprise cellulosic nits treated with 0.02% to 4% by weight of added hydrophobic matter, based on the total weight of the free-flowing particles and added hydrophobic matter.

34. The absorbent article of claim 18, wherein the wicking barrier is a polymeric film.

35. An absorbent article comprising a pouch filled at least in part with free-flowing cellulosic nits, the nits comprising papermaking fibers and a nit conditioner effective to improve free flow of the nits as compared to the nits without the nit conditioner, wherein the nits have an AUL value of about 10 grams/gram or greater and a Centrifuge Retention Capacity value of about 1.5 or greater.

36. An absorbent article comprising a pouch filled at least in part with free-flowing cellulosic nits, the nits comprising papermaking fibers and a nit conditioner effective to improve free flow of the nits as compared to the nits without the nit conditioner,
    wherein the nit conditioner comprises a chemical additive and wherein the nits have been prepared in a predetermined manner and wherein the nits have a substantially higher absorbent capacity than nits prepared in a manner identical to the predetermined manner but without the addition of the chemical additive, and wherein the chemical additive is substantially nonabsorbent.

37. An absorbent article comprising a pouch filled at least in part with cellulosic nits, the nits comprising papermaking fibers and a nit conditioner, wherein the nits have an AUL value of about 10 grams/gram or greater.

38. An absorbent article comprising a pouch filled at least in part with cellulosic nits, the nits comprising papermaking fibers and a nit conditioner, wherein the nits have a Centrifuge Retention Capacity value of about 1.5 or greater.

39. An absorbent article for use on the body of a wearer, the absorbent article having a longitudinal axis, a transverse axis, two longitudinal sides, a target zone and a body side, the absorbent article comprising:
    a) a liquid impervious backsheet;
    b) a liquid pervious topsheet attached to the backsheet;
    c) a conformable intake member comprising a pouch containing free-flowing particles;
    d) an outer shaping member laterally surrounding the pouch; and
    e) a wicking barrier between at least a portion of the pouch and the outer shaping member,
        wherein the free-flowing particles have a Flowability Coefficient of about 2 or greater.

40. The absorbent article of claim 39, wherein the pouch has a width of less than about 5 cm and a length of about 10 cm or greater.

41. The absorbent article of claim 39, wherein the free-flowing particles comprise hardwood nits.

42. The absorbent article of claim 39, wherein the free-flowing particles comprise one of polymeric beads, hollow spheres, and mineral particles.

43. The absorbent article of claim 39, wherein the free-flowing particles comprise at least about 30% nits by weight and no more than about 30% mineral matter by weight.

44. The absorbent article of claim 39, wherein the free-flowing particles are substantially free of clay.

45. The absorbent article of claim 39, wherein at least 25% by mass of the free-flowing particles have a particle size above 300 microns.

46. The absorbent article of claim 39, wherein the free-flowing particles have a mean particle size between about 300 microns and about 600 microns.

47. The absorbent article of claim 39, wherein the free-flowing particles have a Water Retention Value of about 1.5 g/g or greater.

48. The absorbent article of claim 39, wherein the pouch further comprises an odor control agent.

49. The absorbent article of claim 39, wherein the free-flowing particles further comprise one of an odor-control agent, an anti-microbial agent, and a surfactant.

50. The absorbent article of claim 39, wherein the free-flowing particles further comprise an enzyme.

51. The absorbent article of claim 39, further comprising superabsorbent particles within the pouch.

52. The absorbent article of claim 39, wherein the free-flowing particles comprise cellulosic fibers and one of a debonder, a lubricant, a silicone compound, and a surfactant.

53. The absorbent article of claim 39, wherein the free-flowing particles comprise cellulosic fibers treated with a quaternary amine debonder agent.

54. The absorbent article of claim 39, wherein the free-flowing particles comprise cellulosic nits with added hydrophobic matter on at least a portion of the surface of the nits.

55. The absorbent article of claim 39, wherein the free-flowing particles comprise cellulosic nits treated with 0.02% to 4% by weight of added hydrophobic matter.

56. The absorbent article of claim 39, wherein the wicking barrier is a polymeric film.

* * * * *